US012734030B2

(12) United States Patent
Morriss et al.

(10) Patent No.: US 12,734,030 B2
(45) Date of Patent: Sep. 15, 2026

(54) PROSTHETIC HEART VALVE DEVICES AND ASSOCIATED SYSTEMS AND METHODS

(71) Applicant: Twelve, Inc., Redwood City, CA (US)

(72) Inventors: John Morriss, Emerald Hills, CA (US); Hanson S. Gifford, III, Woodside, CA (US)

(73) Assignee: Twelve, Inc., Redwood City, CA (US)

( * ) Notice: Subject to any disclaimer, the term of this patent is extended or adjusted under 35 U.S.C. 154(b) by 678 days.

(21) Appl. No.: 18/346,246

(22) Filed: Jul. 2, 2023

(65) Prior Publication Data

US 2024/0000563 A1 Jan. 4, 2024

Related U.S. Application Data

(63) Continuation of application No. 16/999,883, filed on Aug. 21, 2020, now Pat. No. 11,712,334, which is a (Continued)

(51) Int. Cl.
*A61F 2/24* (2006.01)

(52) U.S. Cl.
CPC .......... *A61F 2/2418* (2013.01); *A61F 2/2403* (2013.01); *A61F 2/2409* (2013.01); *A61F 2/2445* (2013.01); *A61F 2/2457* (2013.01); *A61F 2/246* (2013.01); *A61F 2/2466* (2013.01); *A61F 2220/0008* (2013.01); *A61F 2220/0016* (2013.01); *A61F 2220/005* (2013.01); *A61F 2220/0058* (2013.01);
(Continued)

(58) Field of Classification Search
CPC .... A61F 2/2418; A61F 2/2403; A61F 2/2409; A61F 2/246
See application file for complete search history.

(56) References Cited

U.S. PATENT DOCUMENTS 3,526,219 A 9/1970 Balamuth
3,565,062 A 2/1971 Kuris
(Continued)

FOREIGN PATENT DOCUMENTS

CN 1440261 9/2003
CN 1905846 1/2007
(Continued)

OTHER PUBLICATIONS

US 9,265,606 B2, 02/2016, Buchbinder et al. (withdrawn)
(Continued)

*Primary Examiner* — Brian A Dukert
(74) *Attorney, Agent, or Firm* — Medler Ferro Woodhouse & Mills PLLC

(57) ABSTRACT

Prosthetic heart valve devices for percutaneous replacement of native heart valves and associated systems and method are disclosed herein. A prosthetic heart valve device configured in accordance with a particular embodiment of the present technology can include an expandable support having an outer surface and configured for placement between leaflets of the native valve. The device can also include a plurality of asymmetrically arranged arms coupled to the expandable support and configured to receive the leaflets of the native valve between the arms and the outer surface. In some embodiments, the arms can include tip portions for engaging a subannular surface of the native valve.

19 Claims, 47 Drawing Sheets

Related U.S. Application Data continuation of application No. 16/020,851, filed on Jun. 27, 2018, now Pat. No. 10,751,173, which is a continuation of application No. 15/415,091, filed on Jan. 25, 2017, now Pat. No. 10,034,750, which is a continuation of application No. 15/146,750, filed on May 4, 2016, now Pat. No. 9,585,751, which is a continuation of application No. 14/807,788, filed on Jul. 23, 2015, now Pat. No. 9,579,196, which is a continuation of application No. 13/949,098, filed on Jul. 23, 2013, now Pat. No. 9,125,740, which is a continuation of application No. PCT/US2012/043636, filed on Jun. 21, 2012.

(60) Provisional application No. 61/499,632, filed on Jun. 21, 2011.

(52) U.S. Cl.
CPC ................ *A61F 2230/0006* (2013.01); *A61F 2230/0008* (2013.01); *A61F 2230/0015* (2013.01); *A61F 2230/0054* (2013.01); *A61F 2230/0067* (2013.01); *A61F 2230/0069* (2013.01); *A61F 2250/0037* (2013.01); *A61F 2250/0069* (2013.01)

(56) References Cited

U.S. PATENT DOCUMENTS 3,589,363 A 6/1971 Banko
3,667,474 A 6/1972 Lapkin et al.
3,823,717 A 7/1974 Pohlman et al.
3,861,391 A 1/1975 Antonevich et al.
3,896,811 A 7/1975 Storz
4,042,979 A 8/1977 Angell
4,188,952 A 2/1980 Loschilov et al.
4,388,735 A 6/1983 Ionescu et al.
4,423,525 A 1/1984 Vallana et al.
4,431,006 A 2/1984 Trimmer et al.
4,441,216 A 4/1984 Ionescu et al.
4,445,509 A 5/1984 Auth
4,484,579 A 11/1984 Meno et al.
4,490,859 A 1/1985 Black et al.
4,587,958 A 5/1986 Noguchi et al.
4,589,419 A 5/1986 Laughlin et al.
4,602,911 A 7/1986 Ahmadi et al.
4,629,459 A 12/1986 Ionescu et al.
4,646,736 A 3/1987 Auth
4,653,577 A 3/1987 Noda
4,666,442 A 5/1987 Arru et al.
4,679,556 A 7/1987 Lubock et al.
4,692,139 A 9/1987 Stiles
4,747,821 A 5/1988 Kensey et al.
4,750,902 A 6/1988 Wuchinich et al.
4,758,151 A 7/1988 Arru et al.
4,777,951 A 10/1988 Cribier et al.
4,787,388 A 11/1988 Hofmann
4,796,629 A 1/1989 Grayzel
4,808,153 A 2/1989 Parisi
4,819,751 A 4/1989 Shimada et al.
4,841,977 A 6/1989 Griffith et al.
4,870,953 A 10/1989 DonMicheal et al.
4,878,495 A 11/1989 Grayzel
4,892,540 A 1/1990 Vallana
4,898,575 A 2/1990 Fischell et al.
4,902,954 A 2/1990 Oshima et al.
4,909,252 A 3/1990 Goldberger
4,919,133 A 4/1990 Chiang
4,920,954 A 5/1990 Alliger et al.
4,936,281 A 6/1990 Stasz
4,960,411 A 10/1990 Buchbinder
4,986,830 A 1/1991 Owens et al.
4,990,134 A 2/1991 Auth
5,002,567 A 3/1991 Rona et al.
5,058,570 A 10/1991 Idemoto et al.
5,069,664 A 12/1991 Guess et al.
5,076,276 A 12/1991 Sakurai et al.
5,084,151 A 1/1992 Vallana et al.
5,104,406 A 4/1992 Curcio et al.
5,106,302 A 4/1992 Farzin-nia et al.
5,248,296 A 9/1993 Alliger
5,267,954 A 12/1993 Nita
5,269,291 A 12/1993 Carter
5,295,958 A 3/1994 Shturman
5,304,115 A 4/1994 Pflueger et al.
5,314,407 A 5/1994 Auth et al.
5,318,014 A 6/1994 Carter
5,332,402 A 7/1994 Teitelbaum
5,344,426 A 9/1994 Lau et al.
5,352,199 A 10/1994 Tower
5,356,418 A 10/1994 Shturman
5,370,684 A 12/1994 Vallana et al.
5,387,247 A 2/1995 Vallana et al.
5,397,293 A 3/1995 Alliger et al.
5,411,025 A 5/1995 Webster, Jr.
5,411,552 A 5/1995 Andersen et al.
5,443,446 A 8/1995 Shturman
5,449,373 A 9/1995 Pinchasik et al.
5,489,297 A 2/1996 Duran
5,584,879 A 12/1996 Reimold et al.
5,609,151 A 3/1997 Mulier et al.
5,626,603 A 5/1997 Venturelli et al.
5,656,036 A 8/1997 Palmaz
5,662,671 A 9/1997 Barbut et al.
5,681,336 A 10/1997 Clement et al.
5,695,507 A 12/1997 Auth et al.
5,713,953 A 2/1998 Vallana et al.
5,725,494 A 3/1998 Brisken
5,782,931 A 7/1998 Yang et al.
5,817,101 A 10/1998 Fiedler
5,827,229 A 10/1998 Auth et al.
5,827,321 A 10/1998 Roubin et al.
5,840,081 A 11/1998 Andersen et al.
5,853,422 A 12/1998 Huebsch et al.
5,855,601 A 1/1999 Bessler et al.
5,868,781 A 2/1999 Killion
5,873,811 A 2/1999 Wang et al.
5,873,812 A 2/1999 Ciana et al.
5,904,679 A 5/1999 Clayman
5,910,129 A 6/1999 Koblish et al.
5,957,882 A 9/1999 Nita et al.
5,972,004 A 10/1999 Williamson, IV et al.
5,989,208 A 11/1999 Nita
5,989,280 A 11/1999 Euteneuer et al.
6,047,700 A 4/2000 Eggers et al.
6,056,759 A 5/2000 Fiedler
6,085,754 A 7/2000 Alferness et al.
6,113,608 A 9/2000 Monroe et al.
RE36,939 E 10/2000 Tachibana et al.
6,129,734 A 10/2000 Shturman et al.
6,132,444 A 10/2000 Shturman et al.
6,168,579 B1 1/2001 Tsugita
6,217,595 B1 4/2001 Shturman et al.
6,254,635 B1 7/2001 Schroeder et al.
6,295,712 B1 10/2001 Shturman et al.
6,306,414 B1 10/2001 Koike
6,321,109 B2 11/2001 Ben-haim et al.
6,402,679 B1 6/2002 Mortier et al.
6,423,032 B2 7/2002 Parodi
6,425,916 B1 7/2002 Garrison et al.
6,440,164 B1 8/2002 DiMatteo et al.
6,454,737 B1 9/2002 Nita et al.
6,454,757 B1 9/2002 Nita et al.
6,454,799 B1 9/2002 Schreck
6,458,153 B1 10/2002 Bailey et al.
6,461,382 B1 10/2002 Cao
6,494,890 B1 12/2002 Shturman et al.
6,494,891 B1 12/2002 Cornish et al.
6,505,080 B1 1/2003 Sutton
6,530,952 B2 3/2003 Vesely
6,540,782 B1 4/2003 Snyders
6,562,067 B2 5/2003 Mathis
6,565,588 B1 5/2003 Clement et al.

(56) References Cited

U.S. PATENT DOCUMENTS 6,569,196 B1 5/2003 Vesely
6,579,308 B1 6/2003 Jansen et al.
6,582,462 B1 6/2003 Andersen et al.
6,595,912 B2 7/2003 Lau et al.
6,605,109 B2 8/2003 Fiedler
6,616,689 B1 9/2003 Ainsworth et al.
6,623,452 B2 9/2003 Chien et al.
6,638,288 B1 10/2003 Shturman et al.
6,648,854 B1 11/2003 Patterson et al.
6,689,086 B1 2/2004 Nita et al.
6,702,748 B1 3/2004 Nita et al.
6,730,121 B2 5/2004 Ortiz et al.
6,746,463 B1 6/2004 Schwartz
6,811,801 B2 11/2004 Nguyen et al.
6,818,001 B2 11/2004 Wulfman et al.
6,843,797 B2 1/2005 Nash et al.
6,852,118 B2 2/2005 Shturman et al.
6,855,123 B2 2/2005 Nita
6,869,439 B2 3/2005 White et al.
6,951,571 B1 10/2005 Srivastava
6,986,775 B2 1/2006 Morales et al.
7,018,404 B2 3/2006 Holmberg et al.
7,052,487 B2 5/2006 Cohn et al.
7,077,861 B2 7/2006 Spence
7,125,420 B2 10/2006 Rourke et al.
7,186,264 B2 3/2007 Liddicoat et al.
7,220,277 B2 5/2007 Arru et al.
7,261,732 B2 8/2007 Justino
7,296,577 B2 11/2007 Lashinski et al.
7,381,218 B2 6/2008 Schreck
7,404,824 B1 7/2008 Webler et al.
7,442,204 B2 10/2008 Schwammenthal et al.
7,473,275 B2 1/2009 Marquez
7,510,575 B2 3/2009 Spenser et al.
7,585,321 B2 9/2009 Cribier
7,588,582 B2 9/2009 Starksen et al.
7,621,948 B2 11/2009 Herrmann et al.
7,708,775 B2 5/2010 Rowe et al.
7,748,389 B2 7/2010 Salahieh et al.
7,753,922 B2 7/2010 Starksen
7,753,949 B2 7/2010 Lamphere et al.
7,803,168 B2 9/2010 Gifford et al.
7,857,845 B2 12/2010 Stacchino et al.
7,896,915 B2 3/2011 Guyenot et al.
7,942,928 B2 5/2011 Webler et al.
7,993,392 B2 8/2011 Righini et al.
8,002,826 B2 8/2011 Seguin
8,006,535 B2 8/2011 Righini et al.
8,034,103 B2 10/2011 Burriesci et al.
8,052,750 B2 11/2011 Tuval et al.
8,057,539 B2 11/2011 Ghione et al.
8,062,355 B2 11/2011 Figulla et al.
8,070,799 B2 12/2011 Righini et al.
8,109,996 B2 2/2012 Stacchino et al.
8,114,154 B2 2/2012 Righini et al.
8,252,051 B2 8/2012 Chau et al.
8,353,953 B2 1/2013 Giannetti et al.
8,398,704 B2 3/2013 Straubinger et al.
8,403,981 B2 3/2013 Forster et al.
8,403,982 B2 3/2013 Giannetti et al.
8,403,983 B2 3/2013 Quadri et al.
8,414,643 B2 4/2013 Tuval et al.
8,414,644 B2 4/2013 Quadri et al.
8,449,599 B2 5/2013 Chau et al.
8,470,024 B2 6/2013 Ghione et al.
8,475,521 B2 7/2013 Suri et al.
8,486,137 B2 7/2013 Suri et al.
8,496,671 B1 7/2013 Hausen
8,512,252 B2 8/2013 Ludomirsky et al.
8,512,397 B2 8/2013 Rolando et al.
8,518,107 B2 8/2013 Tsukashima et al.
8,523,883 B2 9/2013 Saadat
8,532,352 B2 9/2013 Ionasec et al.
8,539,662 B2 9/2013 Stacchino et al.
8,540,767 B2 9/2013 Zhang
8,540,768 B2 9/2013 Stacchino et al.
8,545,551 B2 10/2013 Loulmet
8,551,161 B2 10/2013 Dolan
8,579,788 B2 11/2013 Orejola
8,579,964 B2 11/2013 Lane et al.
8,585,755 B2 11/2013 Chau et al.
8,597,347 B2 12/2013 Maurer et al.
8,597,348 B2 12/2013 Rowe et al.
8,608,796 B2 12/2013 Matheny
8,608,797 B2 12/2013 Gross et al.
8,623,077 B2 1/2014 Cohn
8,628,566 B2 1/2014 Eberhardt et al.
8,632,585 B2 1/2014 Seguin et al.
8,632,586 B2 1/2014 Spenser et al.
8,634,935 B2 1/2014 Gaudiani
8,640,521 B2 2/2014 Righini et al.
8,647,254 B2 2/2014 Callas et al.
8,652,203 B2 2/2014 Quadri et al.
8,652,204 B2 2/2014 Quill et al.
8,657,872 B2 2/2014 Seguin
8,672,998 B2 3/2014 Lichtenstein et al.
8,673,001 B2 3/2014 Cartledge et al.
8,679,176 B2 3/2014 Matheny
8,685,086 B2 4/2014 Navia et al.
8,688,234 B2 4/2014 Zhu et al.
8,690,858 B2 4/2014 Machold et al.
8,709,074 B2 4/2014 Solem et al.
8,712,133 B2 4/2014 Guhring et al.
8,715,160 B2 5/2014 Raman et al.
8,715,207 B2 5/2014 Righini et al.
8,721,665 B2 5/2014 Oz et al.
8,721,718 B2 5/2014 Kassab
8,740,918 B2 6/2014 Seguin
8,747,460 B2 6/2014 Tuval et al.
8,758,431 B2 6/2014 Orlov et al.
8,758,432 B2 6/2014 Solem
8,771,292 B2 7/2014 Allen et al.
8,771,345 B2 7/2014 Tuval et al.
8,771,346 B2 7/2014 Tuval et al.
8,777,991 B2 7/2014 Zarbatany et al.
8,778,016 B2 7/2014 Janovsky et al.
8,781,580 B2 7/2014 Hedberg et al.
8,784,482 B2 7/2014 Rahdert et al.
8,792,699 B2 7/2014 Guetter et al.
8,795,356 B2 8/2014 Quadri et al.
8,801,779 B2 8/2014 Seguin et al.
8,808,356 B2 8/2014 Braido et al.
8,808,366 B2 8/2014 Braido et al.
8,808,367 B2 8/2014 Suri et al.
8,812,431 B2 8/2014 Voigt et al.
8,828,043 B2 9/2014 Chambers
8,834,563 B2 9/2014 Righini
8,840,661 B2 9/2014 Manasse
8,845,717 B2 9/2014 Khairkhahan et al.
8,845,723 B2 9/2014 Spence et al.
8,852,213 B2 10/2014 Gammie et al.
8,852,272 B2 10/2014 Gross et al.
8,858,622 B2 10/2014 Machold et al.
8,859,514 B2 10/2014 Crooke et al.
8,859,724 B2 10/2014 Meier et al.
8,864,822 B2 10/2014 Spence et al.
8,870,936 B2 10/2014 Rowe
8,870,948 B1 10/2014 Erzberger et al.
8,870,949 B2 10/2014 Rowe
8,894,702 B2 11/2014 Quadri et al.
8,900,214 B2 12/2014 Nance et al.
8,900,295 B2 12/2014 Migliazza et al.
8,920,411 B2 12/2014 Gelbart et al.
8,920,492 B2 12/2014 Stacchino et al.
8,926,694 B2 1/2015 Costello
8,932,348 B2 1/2015 Solem et al.
8,936,027 B2 1/2015 Santamore et al.
8,951,285 B2 2/2015 Sugimoto et al.
8,961,597 B2 2/2015 Subramanian et al.
8,968,393 B2 3/2015 Rothstein
8,968,395 B2 3/2015 Hauser et al.
8,974,445 B2 3/2015 Warnking et al.
8,979,922 B2 3/2015 Jayasinghe et al.
8,979,923 B2 3/2015 Spence et al.

(56) References Cited

U.S. PATENT DOCUMENTS 8,986,370 B2 3/2015 Annest
8,986,376 B2 3/2015 Solem
8,992,604 B2 3/2015 Gross et al.
9,011,522 B2 4/2015 Annest
9,011,523 B2 4/2015 Seguin
9,017,399 B2 4/2015 Gross et al.
9,023,098 B2 5/2015 Kuehn
9,023,100 B2 5/2015 Quadri et al.
9,034,032 B2 5/2015 McLean et al.
9,034,033 B2 5/2015 McLean et al.
9,039,757 B2 5/2015 McLean et al.
9,050,188 B2 6/2015 Schweich, Jr. et al.
9,056,008 B2 6/2015 Righini et al.
9,066,800 B2 6/2015 Clague et al.
9,084,676 B2 7/2015 Chau et al.
9,095,433 B2 8/2015 Lutter et al.
9,114,010 B2 8/2015 Gaschino et al.
9,119,713 B2 9/2015 Board et al.
9,125,740 B2 9/2015 Morriss et al.
9,132,009 B2 9/2015 Hacohen et al.
9,138,312 B2 9/2015 Tuval et al.
9,138,313 B2 9/2015 McGuckinm, Jr. et al.
9,138,314 B2 9/2015 Rolando et al.
9,149,207 B2 10/2015 Sauter et al.
9,161,836 B2 10/2015 Rolando et al.
9,168,105 B2 10/2015 Giannetti et al.
9,180,005 B1 11/2015 Lashinski et al.
9,186,249 B2 11/2015 Rolando et al.
9,192,466 B2 11/2015 Kovalsky et al.
9,192,471 B2 11/2015 Bolling
9,204,819 B2 12/2015 Grunwald et al.
9,232,942 B2 1/2016 Seguin et al.
9,232,999 B2 1/2016 Maurer et al.
9,241,790 B2 1/2016 Lane et al.
9,248,014 B2 2/2016 Lane et al.
9,248,017 B2 2/2016 Rolando et al.
9,254,192 B2 2/2016 Lutter et al.
9,271,833 B2 3/2016 Kim et al.
9,289,289 B2 3/2016 Rolando et al.
9,289,291 B2 3/2016 Gorman, III et al.
9,289,297 B2 3/2016 Wilson et al.
9,295,547 B2 3/2016 Costello et al.
9,295,552 B2 3/2016 McLean et al.
9,301,836 B2 4/2016 Buchbinder et al.
9,308,087 B2 4/2016 Lane et al.
9,326,850 B2 5/2016 Venkatasubramanian
9,339,207 B2 5/2016 Grunwald et al.
9,339,378 B2 5/2016 Quadri et al.
9,339,379 B2 5/2016 Quadri et al.
9,339,380 B2 5/2016 Quadri et al.
9,339,382 B2 5/2016 Tabor et al.
9,358,105 B2 6/2016 Marchisio et al.
9,358,108 B2 6/2016 Bortlein et al.
9,387,075 B2 7/2016 Bortlein et al.
9,387,078 B2 7/2016 Gross et al.
9,393,111 B2 7/2016 Ma et al.
9,421,094 B2 8/2016 Schweich, Jr. et al.
9,433,574 B2 9/2016 Martin et al.
9,480,559 B2 11/2016 Vidlund et al.
9,486,313 B2 11/2016 Stacchino et al.
9,504,835 B2 11/2016 Graindorge
9,572,662 B2 2/2017 Morriss et al.
9,579,196 B2 2/2017 Morriss et al.
9,585,751 B2 3/2017 Morriss et al.
9,629,719 B2 4/2017 Rothstein et al.
9,655,722 B2 5/2017 Morriss et al.
9,675,454 B2 6/2017 Vidlund et al.
9,681,951 B2 6/2017 Ratz et al.
9,687,342 B2 6/2017 Figulla et al.
9,687,343 B2 6/2017 Bortlein et al.
9,693,859 B2 7/2017 Braido et al.
9,693,862 B2 7/2017 Campbell et al.
9,694,121 B2 7/2017 Alexander et al.
9,700,409 B2 7/2017 Braido et al.
9,700,411 B2 7/2017 Klima et al.
9,700,413 B2 7/2017 Ruyra Baliarda et al.
9,730,791 B2 8/2017 Ratz et al.
9,730,794 B2 8/2017 Carpentier et al.
9,750,605 B2 9/2017 Ganesan et al.
9,750,606 B2 9/2017 Ganesan et al.
9,750,607 B2 9/2017 Ganesan et al.
9,763,657 B2 9/2017 Hacohen et al.
9,763,658 B2 9/2017 Eigler et al.
9,763,780 B2 9/2017 Morriss et al.
9,763,782 B2 9/2017 Solem et al.
9,770,328 B2 9/2017 Macoviak et al.
9,788,931 B2 10/2017 Giordano et al.
9,801,717 B2 10/2017 Edquist et al.
9,827,092 B2 11/2017 Vidlund et al.
9,827,101 B2 11/2017 Solem et al.
9,833,313 B2 12/2017 Board et al.
9,833,315 B2 12/2017 Vidlund et al.
9,839,511 B2 12/2017 Ma et al.
9,844,435 B2 12/2017 Eidenschink
9,848,880 B2 12/2017 Coleman et al.
9,848,981 B2 12/2017 Suri et al.
9,848,983 B2 12/2017 Lashinski et al.
9,861,477 B2 1/2018 Backus et al.
9,861,480 B2 1/2018 Zakai et al.
9,867,695 B2 1/2018 Stacchino et al.
9,895,223 B2 2/2018 Stacchino et al.
9,895,225 B2 2/2018 Rolando et al.
9,901,443 B2 2/2018 Morriss et al.
9,918,841 B2 3/2018 Righini et al.
9,974,647 B2 5/2018 Ganesan et al.
10,016,271 B2 7/2018 Morriss et al.
10,028,827 B2 7/2018 Morriss et al.
10,034,750 B2 7/2018 Morriss et al.
10,052,204 B2 8/2018 McLean et al.
10,058,313 B2 8/2018 Manasse
10,065,032 B2 9/2018 Ollivier
10,098,733 B2 10/2018 Righini
10,117,741 B2 11/2018 Schweich, Jr. et al.
10,143,550 B2 12/2018 Achiluzzi
10,213,301 B2 2/2019 Ganesan et al.
10,245,141 B2 4/2019 Ghione et al.
10,265,166 B2 4/2019 Schweich, Jr. et al.
10,285,810 B2 5/2019 Schweich, Jr. et al.
10,299,917 B2 5/2019 Morriss et al.
10,299,927 B2 5/2019 McLean et al.
10,335,278 B2 7/2019 McLean et al.
10,449,039 B2 10/2019 Ganesan et al.
2001/0021872 A1 9/2001 Bailey et al.
2001/0049492 A1 12/2001 Frazier et al.
2002/0007219 A1 1/2002 Merrill et al.
2002/0013571 A1 1/2002 Goldfarb et al.
2002/0055774 A1 5/2002 Liddicoat
2002/0072792 A1 6/2002 Burgermeister et al.
2002/0077627 A1 6/2002 Johnson et al.
2002/0082637 A1 6/2002 Lumauig
2002/0099439 A1 7/2002 Schwartz et al.
2002/0138138 A1 9/2002 Yang
2002/0151970 A1 10/2002 Garrison et al.
2002/0173841 A1 11/2002 Ortiz et al.
2002/0188350 A1 12/2002 Arru et al.
2003/0120340 A1 6/2003 Liska et al.
2003/0139689 A1 7/2003 Shturman et al.
2004/0006358 A1 1/2004 Wulfman et al.
2004/0039412 A1 2/2004 Isshiki et al.
2004/0044350 A1 3/2004 Martin et al.
2004/0057955 A1 3/2004 O'Brien et al.
2004/0082910 A1 4/2004 Constantz et al.
2004/0092858 A1 5/2004 Wilson et al.
2004/0092962 A1 5/2004 Thornton et al.
2004/0092989 A1 5/2004 Wilson et al.
2004/0106989 A1 6/2004 Wilson et al.
2004/0117009 A1 6/2004 Cali et al.
2004/0122510 A1 6/2004 Sarac
2004/0127979 A1 7/2004 Wilson et al.
2004/0127982 A1 7/2004 Machold et al.
2004/0186558 A1 9/2004 Pavcnik et al.
2004/0199191 A1 10/2004 Schwartz
2004/0230117 A1 11/2004 Tosaya et al.
2004/0230212 A1 11/2004 Wulfman

(56) References Cited

U.S. PATENT DOCUMENTS

2004/0230213 A1 11/2004 Wulfman
2004/0243162 A1 12/2004 Wulfman
2005/0007219 A1 1/2005 Ma et al.
2005/0075662 A1 4/2005 Pedersen et al.
2005/0075720 A1 4/2005 Nguyen et al.
2005/0075727 A1 4/2005 Wheatley
2005/0096647 A1 5/2005 Steinke et al.
2005/0107661 A1 5/2005 Lau et al.
2005/0137682 A1 6/2005 Justino
2005/0137690 A1 6/2005 Salahieh et al.
2005/0137691 A1 6/2005 Salahieh et al.
2005/0137695 A1 6/2005 Salahieh et al.
2005/0137697 A1 6/2005 Salahieh et al.
2005/0137698 A1 6/2005 Salahieh et al.
2005/0137700 A1 6/2005 Spence et al.
2005/0137701 A1 6/2005 Salahieh et al.
2005/0137702 A1 6/2005 Haug et al.
2005/0228477 A1 10/2005 Grainger et al.
2005/0267523 A1 12/2005 Devellian et al.
2005/0273135 A1 12/2005 Chanduszko et al.
2006/0058872 A1 3/2006 Salahieh et al.
2006/0106456 A9 5/2006 Machold et al.
2006/0149360 A1 7/2006 Schwammenthal et al.
2006/0167543 A1 7/2006 Bailey et al.
2006/0195183 A1 8/2006 Navia et al.
2006/0253191 A1 11/2006 Salahieh et al.
2006/0287719 A1 12/2006 Rowe et al.
2007/0016288 A1 1/2007 Gurskis et al.
2007/0056346 A1 3/2007 Spencer et al.
2007/0061010 A1 3/2007 Hauser et al.
2007/0073391 A1 3/2007 Bourang et al.
2007/0078302 A1 4/2007 Ortiz et al.
2007/0088431 A1 4/2007 Bourang et al.
2007/0142906 A1 6/2007 Figulla et al.
2007/0162107 A1 7/2007 Haug et al.
2007/0173932 A1 7/2007 Cali et al.
2007/0213813 A1 9/2007 Von Segesser et al.
2008/0071369 A1 3/2008 Tuval et al.
2008/0082164 A1 4/2008 Friedman
2008/0082166 A1 4/2008 Styrc et al.
2008/0103586 A1 5/2008 Styrc et al.
2008/0140189 A1 6/2008 Nguyen et al.
2008/0147181 A1 6/2008 Ghione et al.
2008/0208332 A1 8/2008 Lamphere et al.
2008/0221672 A1 9/2008 Lamphere et al.
2008/0234728 A1 9/2008 Starksen et al.
2008/0243245 A1 10/2008 Thambar et al.
2008/0243246 A1 10/2008 Ryan et al.
2008/0255678 A1 10/2008 Cully et al.
2008/0262603 A1 10/2008 Giaquinta et al.
2009/0054969 A1 2/2009 Salahieh et al.
2009/0076586 A1 3/2009 Hauser et al.
2009/0076598 A1 3/2009 Salahieh et al.
2009/0093670 A1 4/2009 Annest et al.
2009/0105794 A1 4/2009 Ziamo et al.
2009/0157174 A1 6/2009 Yoganathan et al.
2009/0164006 A1 6/2009 Seguin et al.
2009/0171456 A1 7/2009 Kveen et al.
2009/0198315 A1 8/2009 Boudjemline
2009/0216312 A1 8/2009 Straubinger et al.
2009/0240320 A1 9/2009 Tuval et al.
2009/0259292 A1 10/2009 Bonhoeffer
2009/0259306 A1 10/2009 Rowe
2009/0264997 A1 10/2009 Salahieh et al.
2009/0276040 A1 11/2009 Rowe et al.
2009/0281609 A1 11/2009 Benichou et al.
2009/0281618 A1 11/2009 Hill et al.
2009/0292350 A1 11/2009 Eberhardt et al.
2009/0306768 A1 12/2009 Quadri
2009/0319037 A1 12/2009 Rowe et al.
2009/0319038 A1 12/2009 Gurskis et al.
2010/0016958 A1 1/2010 St. Goar et al.
2010/0023115 A1 1/2010 Robaina et al.
2010/0023117 A1 1/2010 Yoganathan et al.
2010/0030061 A1 2/2010 Canfield et al.
2010/0030330 A1 2/2010 Bobo et al.
2010/0049313 A1 2/2010 Alon et al.
2010/0076376 A1 3/2010 Manasse et al.
2010/0076548 A1 3/2010 Konno
2010/0082094 A1 4/2010 Quadri et al.
2010/0094411 A1 4/2010 Tuval et al.
2010/0121436 A1 5/2010 Tuval et al.
2010/0152840 A1 6/2010 Seguin et al.
2010/0185275 A1 7/2010 Richter et al.
2010/0217382 A1 8/2010 Chau et al.
2010/0249915 A1 9/2010 Zhang
2010/0249923 A1 9/2010 Alkhatib et al.
2010/0298929 A1 11/2010 Thornton et al.
2010/0298931 A1 11/2010 Quadri et al.
2010/0312333 A1 12/2010 Navia et al.
2010/0324554 A1 12/2010 Gifford et al.
2011/0004296 A1 1/2011 Lutter et al.
2011/0015722 A1 1/2011 Hauser et al.
2011/0022166 A1 1/2011 Dahlgren et al.
2011/0029071 A1 2/2011 Zlotnick et al.
2011/0029072 A1 2/2011 Gabbay
2011/0040374 A1 2/2011 Goetz et al.
2011/0040375 A1 2/2011 Letac et al.
2011/0066231 A1 3/2011 Cartledge et al.
2011/0066233 A1 3/2011 Thornton et al.
2011/0098800 A1 4/2011 Braido et al.
2011/0112632 A1 5/2011 Chau et al.
2011/0137397 A1 6/2011 Chau et al.
2011/0137409 A1 6/2011 Yang et al.
2011/0137410 A1 6/2011 Hacohen
2011/0153008 A1 6/2011 Marchand et al.
2011/0172784 A1 7/2011 Richter et al.
2011/0184512 A1 7/2011 Webler et al.
2011/0208293 A1 8/2011 Tabor
2011/0224785 A1 9/2011 Hacohen
2011/0319988 A1 12/2011 Schankereli et al.
2012/0022639 A1 1/2012 Hacohen et al.
2012/0035703 A1 2/2012 Lutter et al.
2012/0035713 A1 2/2012 Lutter et al.
2012/0053680 A1 3/2012 Bolling et al.
2012/0053682 A1 3/2012 Kovalsky et al.
2012/0078347 A1 3/2012 Braido et al.
2012/0078360 A1 3/2012 Rafiee
2012/0101571 A1 4/2012 Thambar et al.
2012/0165930 A1 6/2012 Gifford, III et al.
2012/0179239 A1 7/2012 Quadri
2012/0179244 A1 7/2012 Schankereli et al.
2012/0203336 A1 8/2012 Annest
2012/0283824 A1 11/2012 Lutter et al.
2012/0303048 A1 11/2012 Manasse
2013/0123915 A1 5/2013 Giannetti et al.
2013/0172978 A1 7/2013 Vidlund et al.
2013/0190860 A1 7/2013 Sundt, III
2013/0190861 A1 7/2013 Chau et al.
2013/0197354 A1 8/2013 Maschke et al.
2013/0197630 A1 8/2013 Azarnoush
2013/0204356 A1 8/2013 Dwork et al.
2013/0204358 A1 8/2013 Matheny
2013/0226289 A1 8/2013 Shaolian et al.
2013/0226290 A1 8/2013 Yellin et al.
2013/0231735 A1 9/2013 Deem et al.
2013/0238089 A1 9/2013 Lichtenstein et al.
2013/0244927 A1 9/2013 Lal et al.
2013/0253641 A1 9/2013 Lattouf
2013/0253642 A1 9/2013 Brecker
2013/0253643 A1 9/2013 Rolando et al.
2013/0259337 A1 10/2013 Guhring et al.
2013/0261737 A1 10/2013 Costello
2013/0261738 A1 10/2013 Calgue et al.
2013/0261739 A1 10/2013 Kuehn
2013/0261741 A1 10/2013 Accola
2013/0268066 A1 10/2013 Rowe
2013/0274870 A1 10/2013 Lombardi et al.
2013/0282059 A1 10/2013 Ketai et al.
2013/0282060 A1 10/2013 Tuval
2013/0282110 A1 10/2013 Schweich, Jr. et al.
2013/0289642 A1 10/2013 Hedberg et al.
2013/0289717 A1 10/2013 Solem
2013/0289718 A1 10/2013 Tsukashima et al.

(56) References Cited

U.S. PATENT DOCUMENTS

2013/0296851 A1 11/2013 Boronyak et al.
2013/0296989 A1 11/2013 Slavin
2013/0296999 A1 11/2013 Burriesci et al.
2013/0304180 A1 11/2013 Green et al.
2013/0304181 A1 11/2013 Green et al.
2013/0304197 A1 11/2013 Buchbinder et al.
2013/0304198 A1 11/2013 Solem
2013/0304200 A1 11/2013 McLean et al.
2013/0309292 A1 11/2013 Andersen
2013/0310436 A1 11/2013 Lowes et al.
2013/0310925 A1 11/2013 Eliasen et al.
2013/0310928 A1 11/2013 Morriss et al.
2013/0317603 A1 11/2013 McLean et al.
2013/0325110 A1 12/2013 Khalil et al.
2013/0325114 A1 12/2013 McLean et al.
2013/0331864 A1 12/2013 Jelich et al.
2013/0338684 A1 12/2013 Hausen
2013/0338763 A1 12/2013 Rowe et al.
2013/0338766 A1 12/2013 Hastings et al.
2013/0345797 A1 12/2013 Dahlgren et al.
2013/0345803 A1 12/2013 Bergheim, III
2014/0005778 A1 1/2014 Buchbinder et al.
2014/0018906 A1 1/2014 Rafiee
2014/0018913 A1 1/2014 Cartledge et al.
2014/0023261 A1 1/2014 Watanabe et al.
2014/0025164 A1 1/2014 Montorfano et al.
2014/0031928 A1 1/2014 Murphy et al.
2014/0046219 A1 2/2014 Sauter et al.
2014/0046436 A1 2/2014 Kheradvar
2014/0052237 A1 2/2014 Lane et al.
2014/0052240 A1 2/2014 Zhang
2014/0056906 A1 2/2014 Yue et al.
2014/0066895 A1 3/2014 Kipperman
2014/0067048 A1 3/2014 Chau et al.
2014/0067052 A1 3/2014 Chau et al.
2014/0067054 A1 3/2014 Chau et al.
2014/0088071 A1 3/2014 Nakai et al.
2014/0088680 A1 3/2014 Costello et al.
2014/0088693 A1 3/2014 Seguin et al.
2014/0088695 A1 3/2014 Figulla et al.
2014/0088696 A1 3/2014 Figulla et al.
2014/0094906 A1 4/2014 Spence et al.
2014/0107775 A1 4/2014 Hjelle et al.
2014/0114404 A1 4/2014 Gammie et al.
2014/0114407 A1 4/2014 Rajamannan
2014/0121763 A1 5/2014 Duffy et al.
2014/0128965 A1 5/2014 Rafiee
2014/0135913 A1 5/2014 Lichtenstein et al.
2014/0163652 A1 6/2014 Witzel et al.
2014/0163668 A1 6/2014 Rafiee
2014/0172076 A1 6/2014 Jonsson et al.
2014/0172084 A1 6/2014 Callas et al.
2014/0172085 A1 6/2014 Quadri et al.
2014/0172086 A1 6/2014 Quadri et al.
2014/0179993 A1 6/2014 Alexander et al.
2014/0180401 A1 6/2014 Quill et al.
2014/0188108 A1 7/2014 Goodine et al.
2014/0188215 A1 7/2014 Hlavka et al.
2014/0194920 A1 7/2014 Krahbichler
2014/0194976 A1 7/2014 Starksen et al.
2014/0200397 A1 7/2014 Raman et al.
2014/0200649 A1 7/2014 Essinger et al.
2014/0200657 A1 7/2014 Maurer et al.
2014/0200662 A1 7/2014 Eftel et al.
2014/0207011 A1 7/2014 Righini et al.
2014/0214159 A1 7/2014 Vidlund et al.
2014/0219524 A1 8/2014 Takeguchi et al.
2014/0222040 A1 8/2014 Park et al.
2014/0222138 A1 8/2014 Machold et al.
2014/0228942 A1 8/2014 Krahbichler
2014/0228946 A1 8/2014 Chau et al.
2014/0242086 A1 8/2014 Lal et al.
2014/0243860 A1 8/2014 Morris et al.
2014/0243954 A1 8/2014 Shannon
2014/0243964 A1 8/2014 Venkatasubramanian
2014/0249621 A1 9/2014 Eidenschink
2014/0257101 A1 9/2014 Gaudiani
2014/0257466 A1 9/2014 Board et al.
2014/0257467 A1 9/2014 Lane et al.
2014/0257473 A1 9/2014 Rajamannan
2014/0257475 A1 9/2014 Gross et al.
2014/0275757 A1 9/2014 Goodwin et al.
2014/0276395 A1 9/2014 Wilson et al.
2014/0276609 A1 9/2014 Magee et al.
2014/0276782 A1 9/2014 Paskar
2014/0276971 A1 9/2014 Kovach
2014/0277119 A1 9/2014 Akpinar
2014/0277390 A1 9/2014 Ratz et al.
2014/0277404 A1 9/2014 Wilson et al.
2014/0277405 A1 9/2014 Wilson et al.
2014/0277406 A1 9/2014 Arcidi
2014/0277407 A1 9/2014 Dale et al.
2014/0277408 A1 9/2014 Folan
2014/0277409 A1 9/2014 Bortlein et al.
2014/0277410 A1 9/2014 Bortlein et al.
2014/0277411 A1 9/2014 Bortlein et al.
2014/0277412 A1 9/2014 Bortlein et al.
2014/0277420 A1 9/2014 Migliazza et al.
2014/0277422 A1 9/2014 Ratz et al.
2014/0288480 A1 9/2014 Zimmerman et al.
2014/0296878 A1 10/2014 Oz et al.
2014/0296969 A1 10/2014 Tegels et al.
2014/0296970 A1 10/2014 Ekvall et al.
2014/0296971 A1 10/2014 Tegels et al.
2014/0296975 A1 10/2014 Tegels et al.
2014/0303719 A1 10/2014 Cox et al.
2014/0303721 A1 10/2014 Fung et al.
2014/0309727 A1 10/2014 Lamelas et al.
2014/0309730 A1 10/2014 Alon et al.
2014/0309731 A1 10/2014 Quadri et al.
2014/0309732 A1 10/2014 Solem
2014/0316516 A1 10/2014 Vidlund et al.
2014/0323448 A1 10/2014 Kim et al.
2014/0324164 A1 10/2014 Gross et al.
2014/0330111 A1 11/2014 Lichtenstein et al.
2014/0358222 A1 12/2014 Gorman, III et al.
2014/0358224 A1 12/2014 Tegels et al.
2014/0364944 A1 12/2014 Lutter et al.
2014/0371843 A1 12/2014 Wilson et al.
2014/0371844 A1 12/2014 Dale et al.
2014/0371846 A1 12/2014 Wilson et al.
2014/0378464 A1 12/2014 Oslob et al.
2014/0378491 A1 12/2014 Oslob et al.
2014/0379074 A1 12/2014 Spence et al.
2014/0379076 A1 12/2014 Vidlund et al.
2015/0004165 A1 1/2015 Vue et al.
2015/0005874 A1 1/2015 Vidlund et al.
2015/0005875 A1 1/2015 Tuval et al.
2015/0012069 A1 1/2015 Puskas
2015/0018353 A1 1/2015 Kim et al.
2015/0018940 A1 1/2015 Quill et al.
2015/0025623 A1 1/2015 Granada et al.
2015/0032127 A1 1/2015 Gammie et al.
2015/0032204 A1 1/2015 Johansson
2015/0045878 A1 2/2015 Rowe
2015/0057738 A1 2/2015 Hepke et al.
2015/0066138 A1 3/2015 Alexander et al.
2015/0066140 A1 3/2015 Quadri et al.
2015/0094802 A1 4/2015 Buchbinder et al.
2015/0094803 A1 4/2015 Navia
2015/0100116 A1 4/2015 Mohl et al.
2015/0112427 A1 4/2015 Schweich, Jr. et al.
2015/0112429 A1 4/2015 Khairkhahan et al.
2015/0112433 A1 4/2015 Schweich, Jr. et al.
2015/0119978 A1 4/2015 Tegels et al.
2015/0119981 A1 4/2015 Khairkhahan et al.
2015/0119982 A1 4/2015 Quill et al.
2015/0127091 A1 5/2015 Cecere et al.
2015/0127096 A1 5/2015 Rowe et al.
2015/0142101 A1 5/2015 Coleman et al.
2015/0142103 A1 5/2015 Vidlund
2015/0142105 A1 5/2015 Bolling et al.
2015/0150678 A1 6/2015 Brecker
2015/0157458 A1 6/2015 Thambar et al.

(56) References Cited

U.S. PATENT DOCUMENTS

2015/0157459 A1 6/2015 Macoviak et al.
2015/0164637 A1 6/2015 Khairkhahan et al.
2015/0164641 A1 6/2015 Annest
2015/0173897 A1 6/2015 Raanani et al.
2015/0173898 A1 6/2015 Drasler et al.
2015/0173900 A1 6/2015 Hauser et al.
2015/0190229 A1 7/2015 Seguin
2015/0196390 A1 7/2015 Ma et al.
2015/0196393 A1 7/2015 Vidlund et al.
2015/0202043 A1 7/2015 Zakai et al.
2015/0209137 A1 7/2015 Quadri et al.
2015/0209139 A1 7/2015 Granada et al.
2015/0216655 A1 8/2015 Lane et al.
2015/0216661 A1 8/2015 Hacohen et al.
2015/0223802 A1 8/2015 Tegzes
2015/0223934 A1 8/2015 Vidlund et al.
2015/0223935 A1 8/2015 Subramanian et al.
2015/0230920 A1 8/2015 Alfieri et al.
2015/0230921 A1 8/2015 Chau et al.
2015/0238312 A1 8/2015 Lashinski
2015/0238313 A1 8/2015 Spence et al.
2015/0250590 A1 9/2015 Gries et al.
2015/0257877 A1 9/2015 Hernandez
2015/0257878 A1 9/2015 Lane et al.
2015/0257879 A1 9/2015 Bortlein et al.
2015/0257881 A1 9/2015 Bortlein et al.
2015/0257882 A1 9/2015 Bortlein et al.
2015/0272737 A1 10/2015 Dale et al.
2015/0305861 A1 10/2015 Annest
2015/0305864 A1 10/2015 Quadri et al.
2015/0313739 A1 11/2015 Hummen et al.
2015/0320553 A1 11/2015 Chau et al.
2015/0327999 A1 11/2015 Board et al.
2015/0328000 A1 11/2015 Ratz et al.
2015/0342733 A1 12/2015 Alkhatib et al.
2015/0342737 A1 12/2015 Biancucci et al.
2015/0351906 A1 12/2015 Hammer et al.
2015/0351908 A1 12/2015 Keranen et al.
2015/0359628 A1 12/2015 Keranen
2015/0359629 A1 12/2015 Ganesan et al.
2015/0359631 A1 12/2015 Sheahan et al.
2015/0366666 A1 12/2015 Khairkhahan et al.
2015/0374495 A1 12/2015 Ruyra Baliarda et al.
2016/0000983 A1 1/2016 Mohl et al.
2016/0015513 A1 1/2016 Lashinski et al.
2016/0015514 A1 1/2016 Lashinski et al.
2016/0015515 A1 1/2016 Lashinski et al.
2016/0015543 A1 1/2016 Perouse et al.
2016/0030171 A1 2/2016 Quijano et al.
2016/0038246 A1 2/2016 Wang et al.
2016/0038280 A1 2/2016 Morriss et al.
2016/0038283 A1 2/2016 Divekar et al.
2016/0038286 A1 2/2016 Yellin et al.
2016/0074160 A1 3/2016 Christianson et al.
2016/0106539 A1 4/2016 Buchbinder et al.
2016/0113764 A1 4/2016 Sheahan et al.
2016/0113765 A1 4/2016 Ganesan et al.
2016/0113766 A1 4/2016 Ganesan et al.
2016/0113768 A1 4/2016 Ganesan et al.
2016/0120643 A1 5/2016 Kupumbati
2016/0143730 A1 5/2016 Kheradvar
2016/0151154 A1 6/2016 Gorman, III et al.
2016/0151156 A1 6/2016 Seguin et al.
2016/0151552 A1 6/2016 Solem
2016/0157999 A1 6/2016 Lane et al.
2016/0158000 A1 6/2016 Granada et al.
2016/0158001 A1 6/2016 Wallace et al.
2016/0158002 A1 6/2016 Wallace et al.
2016/0158003 A1 6/2016 Wallace et al.
2016/0158415 A1 6/2016 Strasly et al.
2016/0184095 A1 6/2016 Spence et al.
2016/0206280 A1 7/2016 Vidlund et al.
2016/0206424 A1 7/2016 Al-jilaihawi et al.
2016/0262881 A1 9/2016 Schankereli et al.
2016/0317290 A1 11/2016 Chau et al.
2017/0079790 A1 3/2017 Vidlund et al.
2017/0100248 A1 4/2017 Tegels et al.
2017/0100250 A1 4/2017 Marsot et al.
2017/0119526 A1 5/2017 Luong et al.
2017/0128198 A1 5/2017 Cartledge et al.
2017/0128205 A1 5/2017 Tamir et al.
2017/0128206 A1 5/2017 Rafiee et al.
2017/0128208 A1 5/2017 Christianson et al.
2017/0156860 A1 6/2017 Lashinski
2017/0165054 A1 6/2017 Benson et al.
2017/0165055 A1 6/2017 Hauser et al.
2017/0165064 A1 6/2017 Nyulli et al.
2017/0172737 A1 6/2017 Kuetting et al.
2017/0181851 A1 6/2017 Annest
2017/0189177 A1 7/2017 Schweich, Jr. et al.
2017/0189179 A1 7/2017 Ratz et al.
2017/0189180 A1 7/2017 Alkhatib
2017/0189181 A1 7/2017 Alkhatib et al.
2017/0196688 A1 7/2017 Christianson et al.
2017/0231762 A1 8/2017 Quadri et al.
2017/0231763 A1 8/2017 Yellin et al.
2017/0258585 A1 9/2017 Marquez et al.
2017/0266001 A1 9/2017 Vidlund et al.
2017/0281345 A1 10/2017 Yang et al.
2017/0290659 A1 10/2017 Ulmer et al.
2017/0296338 A1 10/2017 Cambell et al.
2017/0296339 A1 10/2017 Thambar et al.
2017/0319333 A1 11/2017 Tegels et al.
2017/0325842 A1 11/2017 Siegel
2017/0325941 A1 11/2017 Wallace et al.
2017/0325945 A1 11/2017 Dale et al.
2017/0325948 A1 11/2017 Wallace et al.
2017/0325949 A1 11/2017 Rodgers et al.
2017/0325953 A1 11/2017 Klima et al.
2017/0325954 A1 11/2017 Perszyk
2017/0333186 A1 11/2017 Spargias
2017/0333188 A1 11/2017 Carpentier et al.
2017/0340440 A1 11/2017 Ratz et al.
2017/0348097 A1 12/2017 Taft et al.
2017/0348098 A1 12/2017 Rowe et al.
2017/0348100 A1 12/2017 Lane et al.
2017/0354496 A1 12/2017 Quadri et al.
2017/0354497 A1 12/2017 Quadri et al.
2017/0354499 A1 12/2017 Granada et al.
2017/0360426 A1 12/2017 Hacohen et al.
2017/0360549 A1 12/2017 Lashinski et al.
2017/0360558 A1 12/2017 Ma
2017/0360585 A1 12/2017 White
2017/0361065 A1 12/2017 Legaspi et al.
2018/0014931 A1 1/2018 Morriss et al.
2018/0116843 A1 5/2018 Schreck et al.
2018/0161585 A1 6/2018 Ollivier
2018/0214263 A1 8/2018 Rolando et al.
2018/0221147 A1 8/2018 Ganesan et al.
2018/0235753 A1 8/2018 Ganesan et al.
2018/0311037 A1 11/2018 Morriss et al.
2018/0338832 A1 11/2018 Ganesan et al.
2019/0000618 A1 1/2019 Schweich, Jr. et al.
2019/0029814 A1 1/2019 Schweich, Jr. et al.
2019/0142581 A1 5/2019 Maiso et al.
2019/0183641 A1 6/2019 Ganesan et al.
2019/0192292 A1 6/2019 Schweich, Jr. et al.
2019/0321171 A1 10/2019 Morriss et al.

FOREIGN PATENT DOCUMENTS

CN 1961845 5/2007
CN 1993090 7/2007
CN 101076290 11/2007
CN 101291637 10/2008
CN 101374477 2/2009
CN 101484093 7/2009
CN 101636128 1/2010
CN 101742975 6/2010
CN 101919753 12/2010
CN 101951857 1/2011
CN 102014796 4/2011
CN 102083393 6/2011
CN 102119013 7/2011

(56) References Cited

FOREIGN PATENT DOCUMENTS

| | | | |
|---|---|---|---|
| CN | 103491900 | | 1/2014 |
| DE | 19605042 | | 1/1998 |
| DE | 102006052564 | | 12/2007 |
| EP | 0186104 | | 7/1986 |
| EP | 0224080 | B1 | 7/1992 |
| EP | 1512383 | | 3/2005 |
| EP | 1088529 | B1 | 6/2005 |
| EP | 1545371 | | 6/2005 |
| EP | 1551274 | | 7/2005 |
| EP | 1629794 | | 3/2006 |
| EP | 1646332 | | 4/2006 |
| EP | 1702247 | | 9/2006 |
| EP | 1734903 | | 12/2006 |
| EP | 1891914 | | 2/2008 |
| EP | 1967164 | A2 | 9/2008 |
| EP | 2026280 | | 2/2009 |
| EP | 2033581 | A1 | 3/2009 |
| EP | 2037829 | | 3/2009 |
| EP | 2081519 | | 7/2009 |
| EP | 2111190 | | 10/2009 |
| EP | 2142143 | | 1/2010 |
| EP | 2167742 | | 3/2010 |
| EP | 2203124 | | 7/2010 |
| EP | 2014257 | B1 | 9/2010 |
| EP | 2248486 | A2 | 11/2010 |
| EP | 2278944 | | 2/2011 |
| EP | 2033597 | B1 | 3/2011 |
| EP | 2306821 | | 4/2011 |
| EP | 2327429 | | 6/2011 |
| EP | 2165651 | B1 | 8/2011 |
| EP | 1719476 | B1 | 11/2011 |
| EP | 2399527 | A1 | 12/2011 |
| EP | 2400924 | | 1/2012 |
| EP | 2400926 | | 1/2012 |
| EP | 2410947 | | 2/2012 |
| EP | 2419050 | | 2/2012 |
| EP | 2399527 | A8 | 3/2012 |
| EP | 2444031 | | 4/2012 |
| EP | 2488126 | | 8/2012 |
| EP | 2509538 | | 10/2012 |
| EP | 2522307 | | 11/2012 |
| EP | 2549955 | | 1/2013 |
| EP | 2549956 | | 1/2013 |
| EP | 2566416 | | 3/2013 |
| EP | 2586492 | | 5/2013 |
| EP | 2618784 | | 7/2013 |
| EP | 2623068 | | 8/2013 |
| EP | 2626012 | | 8/2013 |
| EP | 2626012 | A2 | 8/2013 |
| EP | 2626013 | | 8/2013 |
| EP | 2629699 | | 8/2013 |
| EP | 2633457 | | 9/2013 |
| EP | 2637659 | | 9/2013 |
| EP | 2641569 | | 9/2013 |
| EP | 2644158 | | 10/2013 |
| EP | 2654624 | | 10/2013 |
| EP | 2656794 | | 10/2013 |
| EP | 2656795 | | 10/2013 |
| EP | 2656796 | | 10/2013 |
| EP | 2667823 | | 12/2013 |
| EP | 2670358 | | 12/2013 |
| EP | 2676640 | | 12/2013 |
| EP | 2688041 | | 1/2014 |
| EP | 2693984 | | 2/2014 |
| EP | 2695586 | | 2/2014 |
| EP | 2697721 | | 2/2014 |
| EP | 2713953 | | 4/2014 |
| EP | 2714068 | | 4/2014 |
| EP | 2723272 | | 4/2014 |
| EP | 2723273 | | 4/2014 |
| EP | 2723277 | | 4/2014 |
| EP | 2739214 | | 6/2014 |
| EP | 2741711 | | 6/2014 |
| EP | 2750630 | | 7/2014 |
| EP | 2750631 | | 7/2014 |
| EP | 2755562 | | 7/2014 |
| EP | 2755602 | | 7/2014 |
| EP | 2757962 | | 7/2014 |
| EP | 2777616 | | 9/2014 |
| EP | 2777617 | | 9/2014 |
| EP | 2203124 | B1 | 10/2014 |
| EP | 2782523 | | 10/2014 |
| EP | 2785282 | | 10/2014 |
| EP | 2786817 | | 10/2014 |
| EP | 2790609 | | 10/2014 |
| EP | 2793751 | | 10/2014 |
| EP | 2229921 | B1 | 11/2014 |
| EP | 2797915 | | 11/2014 |
| EP | 2800063 | | 11/2014 |
| EP | 2809263 | | 12/2014 |
| EP | 2810620 | | 12/2014 |
| EP | 2811939 | | 12/2014 |
| EP | 2814428 | | 12/2014 |
| EP | 2814429 | | 12/2014 |
| EP | 2819617 | | 1/2015 |
| EP | 2819618 | | 1/2015 |
| EP | 2819619 | | 1/2015 |
| EP | 2822473 | | 1/2015 |
| EP | 2416739 | | 2/2015 |
| EP | 2717803 | | 2/2015 |
| EP | 2833836 | | 2/2015 |
| EP | 2838475 | | 2/2015 |
| EP | 2839815 | | 2/2015 |
| EP | 2844190 | | 3/2015 |
| EP | 2849680 | | 3/2015 |
| EP | 2849681 | | 3/2015 |
| EP | 2693984 | B1 | 4/2015 |
| EP | 2852354 | | 4/2015 |
| EP | 2854719 | | 4/2015 |
| EP | 2861186 | A2 | 4/2015 |
| EP | 2870933 | | 5/2015 |
| EP | 2873011 | | 5/2015 |
| EP | 2875797 | | 5/2015 |
| EP | 2760375 | | 6/2015 |
| EP | 2882374 | | 6/2015 |
| EP | 2886082 | | 6/2015 |
| EP | 2886083 | | 6/2015 |
| EP | 2886084 | | 6/2015 |
| EP | 2895111 | | 7/2015 |
| EP | 2250976 | B1 | 8/2015 |
| EP | 2901966 | | 8/2015 |
| EP | 2907479 | | 8/2015 |
| EP | 2945572 | | 11/2015 |
| EP | 2948094 | | 12/2015 |
| EP | 2948102 | | 12/2015 |
| EP | 2964152 | | 1/2016 |
| EP | 2967859 | | 1/2016 |
| EP | 2967860 | | 1/2016 |
| EP | 2967866 | | 1/2016 |
| EP | 2968847 | | 1/2016 |
| EP | 2981208 | | 2/2016 |
| EP | 2982336 | | 2/2016 |
| EP | 2999433 | | 3/2016 |
| EP | 3003187 | | 4/2016 |
| EP | 3003219 | | 4/2016 |
| EP | 3003220 | | 4/2016 |
| EP | 3010447 | | 4/2016 |
| EP | 3013281 | | 5/2016 |
| EP | 3017792 | | 5/2016 |
| EP | 3021792 | | 5/2016 |
| EP | 3023117 | | 5/2016 |
| EP | 3027143 | | 6/2016 |
| EP | 3033048 | | 6/2016 |
| EP | 3037064 | | 6/2016 |
| EP | 2797915 | B1 | 7/2016 |
| EP | 3050541 | A1 | 8/2016 |
| EP | 3079633 | | 10/2016 |
| EP | 2717803 | B1 | 11/2016 |
| EP | 3229736 | | 11/2016 |
| EP | 3102152 | A1 | 12/2016 |
| EP | 2470119 | | 5/2017 |
| EP | 2999436 | | 5/2017 |
| EP | 3184081 | | 6/2017 |
| EP | 3191027 | | 7/2017 |

(56) References Cited

FOREIGN PATENT DOCUMENTS

| | | |
|---|---|---|
| EP | 2611389 | 8/2017 |
| EP | 3082656 | 8/2017 |
| EP | 3206628 | 8/2017 |
| EP | 2010103 | 9/2017 |
| EP | 2811939 B1 | 9/2017 |
| EP | 3223751 | 10/2017 |
| EP | 3027144 | 11/2017 |
| EP | 3110368 | 11/2017 |
| EP | 3110369 | 11/2017 |
| EP | 3132773 | 11/2017 |
| EP | 3245980 | 11/2017 |
| EP | 3250154 | 12/2017 |
| EP | 3256074 | 12/2017 |
| EP | 3256077 | 12/2017 |
| EP | 3258883 | 12/2017 |
| EP | 3270825 | 1/2018 |
| EP | 3273910 | 1/2018 |
| EP | 2822473 B1 | 8/2018 |
| EP | 3398560 | 11/2018 |
| JP | H06504516 | 5/1994 |
| JP | H06505416 | 5/1994 |
| JP | H10258124 | 9/1998 |
| JP | 2002509756 | 4/2002 |
| JP | 2005280917 | 10/2005 |
| JP | 2008528117 | 7/2008 |
| JP | 2008541863 | 11/2008 |
| JP | 2009195712 | 9/2009 |
| JP | 2010518947 | 6/2010 |
| JP | 2012500665 | 1/2012 |
| JP | 5219518 | 6/2013 |
| WO | WO1992017118 | 10/1992 |
| WO | WO1995016407 | 6/1995 |
| WO | WO1999004730 | 2/1999 |
| WO | WO1999039648 | 8/1999 |
| WO | WO1999049799 | 10/1999 |
| WO | WO2001006959 | 2/2001 |
| WO | WO2001010343 | 2/2001 |
| WO | WO2002003892 | 1/2002 |
| WO | WO2002028421 | 4/2002 |
| WO | WO2002039908 | 5/2002 |
| WO | WO2002049543 | 6/2002 |
| WO | WO2003043685 | 5/2003 |
| WO | WO2004084746 | 10/2004 |
| WO | WO2004093728 | 11/2004 |
| WO | WO2004096097 | 11/2004 |
| WO | WO2004112657 | 12/2004 |
| WO | WO2005002466 | 1/2005 |
| WO | WO2005007219 | 1/2005 |
| WO | WO2005009285 | 2/2005 |
| WO | WO2005009506 | 2/2005 |
| WO | WO2005087140 | 9/2005 |
| WO | WO2006041877 | 4/2006 |
| WO | WO2006063199 | 6/2006 |
| WO | WO2007008371 | 1/2007 |
| WO | WO2007053243 | 5/2007 |
| WO | WO2007067820 | 6/2007 |
| WO | WO2007071436 | 6/2007 |
| WO | WO2008022077 | 2/2008 |
| WO | WO2008028569 | 3/2008 |
| WO | WO2008035337 | 3/2008 |
| WO | WO2008103497 | 8/2008 |
| WO | WO2008103722 | 8/2008 |
| WO | WO2008125153 | 10/2008 |
| WO | WO2008129405 | 10/2008 |
| WO | WO2009045338 | 4/2009 |
| WO | WO2009091509 | 7/2009 |
| WO | WO2009106545 | 9/2009 |
| WO | WO2010006627 | 1/2010 |
| WO | WO2010008549 | 1/2010 |
| WO | WO2010017041 | 2/2010 |
| WO | WO2010057262 | 5/2010 |
| WO | WO2010080594 | 7/2010 |
| WO | WO2010098857 | 9/2010 |
| WO | WO2010099032 | 9/2010 |
| WO | WO2010117680 | 10/2010 |
| WO | WO2010121076 | 10/2010 |
| WO | WO2011025945 | 3/2011 |
| WO | WO2011025981 | 3/2011 |
| WO | WO2011047168 | 4/2011 |
| WO | WO2011051043 | 5/2011 |
| WO | WO2011057087 | 5/2011 |
| WO | WO2011072084 | 6/2011 |
| WO | WO2011106137 | 9/2011 |
| WO | WO2011106544 | 9/2011 |
| WO | WO2011111047 | 9/2011 |
| WO | WO2011137531 | 11/2011 |
| WO | WO2011139747 | 11/2011 |
| WO | WO2011163275 | 12/2011 |
| WO | WO2012011018 | 1/2012 |
| WO | WO2012011108 | 1/2012 |
| WO | WO2012027487 | 3/2012 |
| WO | WO2012035279 | 3/2012 |
| WO | WO2012040655 | 3/2012 |
| WO | WO2012047644 | 4/2012 |
| WO | WO2012052718 | 4/2012 |
| WO | WO2012055498 | 5/2012 |
| WO | WO2012087842 | 6/2012 |
| WO | WO2012095159 | 7/2012 |
| WO | WO2012095455 | 7/2012 |
| WO | WO2012102928 | 8/2012 |
| WO | WO2012106602 | 8/2012 |
| WO | WO2012118508 | 9/2012 |
| WO | WO2012118816 | 9/2012 |
| WO | WO2012118894 | 9/2012 |
| WO | WO2012177942 | 12/2012 |
| WO | WO2013021374 | 2/2013 |
| WO | WO2013021375 | 2/2013 |
| WO | WO2013028387 | 2/2013 |
| WO | WO2013059743 | 4/2013 |
| WO | WO2013059747 | 4/2013 |
| WO | WO2013082454 | 6/2013 |
| WO | WO2013101830 | 7/2013 |
| WO | WO2013114214 | 8/2013 |
| WO | WO2013120082 | 8/2013 |
| WO | WO2013120181 | 8/2013 |
| WO | WO2013123059 | 8/2013 |
| WO | WO2013128432 | 9/2013 |
| WO | WO2013130641 | 9/2013 |
| WO | WO2013131925 | 9/2013 |
| WO | WO2013140318 | 9/2013 |
| WO | WO2013148017 | 10/2013 |
| WO | WO2013148018 | 10/2013 |
| WO | WO2013148019 | 10/2013 |
| WO | WO2013150512 | 10/2013 |
| WO | WO2013152161 | 10/2013 |
| WO | WO2013158613 | 10/2013 |
| WO | WO2013169448 | 11/2013 |
| WO | WO2013175468 | 11/2013 |
| WO | WO2013176583 | 11/2013 |
| WO | WO2013177684 | 12/2013 |
| WO | WO2013188077 | 12/2013 |
| WO | WO2013192107 | 12/2013 |
| WO | WO2014036113 | 3/2014 |
| WO | WO2014043527 | 3/2014 |
| WO | WO2014047111 | 3/2014 |
| WO | WO2014047325 | 3/2014 |
| WO | WO2014055981 | 4/2014 |
| WO | WO2014059432 | 4/2014 |
| WO | WO2014064694 | 5/2014 |
| WO | WO2014066365 | 5/2014 |
| WO | WO2014089424 | 6/2014 |
| WO | WO2014093861 | 6/2014 |
| WO | WO2014110169 | 7/2014 |
| WO | WO2014111918 | 7/2014 |
| WO | WO2014114794 | 7/2014 |
| WO | WO2014114795 | 7/2014 |
| WO | WO2014114796 | 7/2014 |
| WO | WO2014114798 | 7/2014 |
| WO | WO2014116502 | 7/2014 |
| WO | WO2014121280 | 8/2014 |
| WO | WO2014128705 | 8/2014 |
| WO | WO2014134277 | 9/2014 |
| WO | WO2014138194 | 9/2014 |
| WO | WO2014138284 | 9/2014 |

(56) References Cited

FOREIGN PATENT DOCUMENTS

| | | |
|---|---|---|
| WO | WO2014138482 | 9/2014 |
| WO | WO2014138868 | 9/2014 |
| WO | WO2014144100 | 9/2014 |
| WO | WO2014144937 | 9/2014 |
| WO | WO2014145338 | 9/2014 |
| WO | WO2014147336 | 9/2014 |
| WO | WO2014152306 | 9/2014 |
| WO | WO2014152375 | 9/2014 |
| WO | WO2014152503 | 9/2014 |
| WO | WO2014153544 | 9/2014 |
| WO | WO2014158617 | 10/2014 |
| WO | WO2014162181 | 10/2014 |
| WO | WO2014162306 | 10/2014 |
| WO | WO2014163705 | 10/2014 |
| WO | WO2014168655 | 10/2014 |
| WO | WO2014179391 | 11/2014 |
| WO | WO2014181336 | 11/2014 |
| WO | WO2014189974 | 11/2014 |
| WO | WO2014191994 | 12/2014 |
| WO | WO2014193951 | 12/2014 |
| WO | WO2014194178 | 12/2014 |
| WO | WO2014197924 | 12/2014 |
| WO | WO2014200764 | 12/2014 |
| WO | WO2014201384 | 12/2014 |
| WO | WO2014201452 | 12/2014 |
| WO | WO2014205064 | 12/2014 |
| WO | WO2014205223 | 12/2014 |
| WO | WO2014205234 | 12/2014 |
| WO | WO2014207699 | 12/2014 |
| WO | WO2014210124 | 12/2014 |
| WO | WO2014210299 | 12/2014 |
| WO | WO2015003183 | 1/2015 |
| WO | WO2015006575 | 1/2015 |
| WO | WO2015009503 | 1/2015 |
| WO | WO2015013238 | 1/2015 |
| WO | WO2015020971 | 2/2015 |
| WO | WO2015028986 | 3/2015 |
| WO | WO2015031898 | 3/2015 |
| WO | WO2015051430 | 4/2015 |
| WO | WO2015052663 | 4/2015 |
| WO | WO2015057407 | 4/2015 |
| WO | WO2015057735 | 4/2015 |
| WO | WO2015057995 | 4/2015 |
| WO | WO2015061378 | 4/2015 |
| WO | WO2015061431 | 4/2015 |
| WO | WO2015061463 | 4/2015 |
| WO | WO2015061533 | 4/2015 |
| WO | WO2015075128 | 5/2015 |
| WO | WO2015081775 | 6/2015 |
| WO | WO2015089334 | 6/2015 |
| WO | WO2015092554 | 6/2015 |
| WO | WO2015118464 | 8/2015 |
| WO | WO2015120122 | 8/2015 |
| WO | WO2015125024 | 8/2015 |
| WO | WO2015127264 | 8/2015 |
| WO | WO2015127283 | 8/2015 |
| WO | WO2015191604 | 8/2015 |
| WO | WO2015191839 | 8/2015 |
| WO | WO2015195823 | 8/2015 |
| WO | WO2016011185 | 8/2015 |
| WO | WO2015128739 | 9/2015 |
| WO | WO2015128741 | 9/2015 |
| WO | WO2015128747 | 9/2015 |
| WO | WO2015132667 | 9/2015 |
| WO | WO2015132668 | 9/2015 |
| WO | WO2015135050 | 9/2015 |
| WO | WO2015142648 | 9/2015 |
| WO | WO2015142834 | 9/2015 |
| WO | WO2016020918 | 9/2015 |
| WO | WO2016027272 | 9/2015 |
| WO | WO2016059533 | 9/2015 |
| WO | WO2016065158 | 9/2015 |
| WO | WO2016073741 | 9/2015 |
| WO | WO2016083551 | 9/2015 |
| WO | WO2016093877 | 9/2015 |
| WO | WO2015145241 | 10/2015 |
| WO | WO2015148241 | 10/2015 |
| WO | WO2015171190 | 11/2015 |
| WO | WO2015171743 | 11/2015 |
| WO | WO2015179181 | 11/2015 |
| WO | WO2015184452 | 12/2015 |
| WO | WO2016097337 | 6/2016 |
| WO | WO2016108181 | 7/2016 |
| WO | WO2016130524 | 8/2016 |
| WO | WO2016133950 | 8/2016 |
| WO | WO2016150806 | 9/2016 |
| WO | WO2016201024 | 12/2016 |
| WO | WO2016209970 | 12/2016 |
| WO | WO2017011697 | 1/2017 |
| WO | WO2017062640 | 4/2017 |
| WO | WO2017087701 | 5/2017 |
| WO | WO2017096157 | 6/2017 |
| WO | WO2017100927 | 6/2017 |
| WO | WO2017101232 | 6/2017 |
| WO | WO2017117388 | 7/2017 |
| WO | WO2017127939 | 8/2017 |
| WO | WO2017136287 | 8/2017 |
| WO | WO2017136596 | 8/2017 |
| WO | WO2017165810 | 9/2017 |
| WO | WO2017173331 | 10/2017 |
| WO | WO2017192960 | 11/2017 |
| WO | WO2017196511 | 11/2017 |
| WO | WO2017196909 | 11/2017 |
| WO | WO2017196977 | 11/2017 |
| WO | WO2017197064 | 11/2017 |
| WO | WO2017197065 | 11/2017 |
| WO | WO2017189040 | 12/2017 |
| WO | WO2017218671 | 12/2017 |
| WO | WO2018017886 | 1/2018 |
| WO | WO2018167536 | 9/2018 |
| WO | WO2019069145 | 4/2019 |
| WO | WO2019209927 | 10/2019 |

OTHER PUBLICATIONS

Extended European Search Report, EP Application No. 21203988.7, dated Feb. 9, 2022.

"Optison (Perflutren Protein—Type A Microspheres for Injection, USP)." GE Healthcare. General Electric Company. 1997-2005. Retrieved from http://www.amershamhealth-us.com/optison/ on May 26, 2005, 11 pp.

Examination Report No. 1 from counterpart Australian Patent Application No. 2012272855, dated Jun. 16, 2016, 5 pp.

Response to Examination Report No. 1 from counterpart Australian Patent Application No. 2012272855, dated Jun. 16, 2016, filed Apr. 24, 2017, 35 pp.

Notice of Acceptance from counterpart Australian Patent Application No. 2012272855, dated Jun. 5, 2017, 4 pp.

Notice of Grant from counterpart Australian Patent Application No. 2012272855, dated Sep. 28, 2017, 1 pp.

Examination Report No. 1 from counterpart Australian Patent Application No. 2017228689, dated Jun. 7, 2018, 6 pp.

Response to Examination Report No. 1 from counterpart Australian Patent Application No. 2017228689, dated Jun. 7, 2018, filed Apr. 30, 2019, 40 pp.

Notice of Acceptance from counterpart Australian Patent Application No. 2017228689, dated May 23, 2019, 3 pp.

Examiner's Report from counterpart Canadian Patent Application No. 2840084, dated Jun. 20, 2018, 4 pp.

Response to Examiner's Report from counterpart Canadian Patent Application No. 2840084, dated Jun. 20, 2018, filed Dec. 20, 2018, 11 pp.

Notice of Allowance from counterpart Canadian Patent Application No. 2840084, dated Mar. 20, 2019, 1 pp.

First Office Action, and translation thereof, from counterpart Chinese Application No. 201280040748.3, dated Jun. 30, 2015, 14 pp.

Response to First Office Action, translation only, from counterpart Chinese Application No. 201280040748.3, dated Jun. 30, 2015, filed Jan. 7, 2016, 28 pp.

(56) References Cited

OTHER PUBLICATIONS

Communication pursuant to Rules 161(1) and 162 EPC from counterpart European Application No. 12802492.4, dated Feb. 20, 2014, 3 pp.
Response to Communication pursuant to Rules 161(1) and 162 EPC from counterpart European Application No. 12802492.4, dated Feb. 20, 2014, filed Aug. 26, 2014, 4 pp.
Communication pursuant to Rules 70(2) and 70a(2) EPC from counterpart European Application No. 12802492.4, dated Nov. 20, 2014, 7 pp.
Response to Communication pursuant to Rules 70(2) and 70a(2) EPC from counterpart European Application No. 12802492.4, dated Nov. 20, 2014, filed May 29, 2015, 9 pp.
Communication pursuant to Article 94(3) EPC from counterpart European Application No. 12802492.4, dated Jul. 6, 2017, 4 pp.
Response to Communication pursuant to Article 94(3) EPC from counterpart European Application No. 12802492.4, dated Jul. 6, 2017, filed Nov. 15, 2017, 18 pp.
Office action, and translation thereof, from counterpart Japanese Patent Application No. 2014-517188, dated Aug. 31, 2015, 7 pp.
Office action, and translation thereof, from counterpart Japanese Patent Application No. 2016-004528, dated Jul. 27, 2017, 12 pp.
Office action translation only thereof, from counterpart Japanese Patent Application No. 2017-217146, dated Jul. 3, 2018, 3 pp.
Office action, and translation thereof, from counterpart Japanese Patent Application No. 2017-217146, dated Feb. 28, 2019, 10 pp.
Office action, and translation thereof, from counterpart Japanese Patent Application No. 2017-217146, dated Oct. 29, 2019, 3 pp.
Prosecution History from U.S. Appl. No. 13/949,098, dated Nov. 26, 2013 through Jul. 17, 2015, 95 pp.
Prosecution History from U.S. Appl. No. 14/807,788, dated Dec. 9, 2015 through Oct. 25, 2016, 52 pp.
Prosecution History from U.S. Appl. No. 15/146,750, dated Jul. 1, 2016 through Oct. 24, 2016, 22 pp.
Prosecution History from U.S. Appl. No. 15/146,773, dated Jul. 5, 2016 through Oct. 19, 2016, 21 pp.
Prosecution History from U.S. Appl. No. 15/415,091, dated Nov. 17, 2017 through Mar. 30, 2018, 24 pp.
Prosecution History from U.S. Appl. No. 15/415,197, dated Nov. 17, 2017 through Mar. 30, 2018, 25 pp.
Bernard et al., "Aortic Valve Area Evolution After Percutaneous Aortic Valvuloplasty," European Heart Journal, Jul. 1990, vol. 11 (2), pp. 98-107.
BlueCross BlueShield of Northern Carolina Corporate Medical Policy "Balloon valvuloplasty, Percutaneous", (Jun. 1994).
Cimino et al., "Physics of Ultrasonic Surgery Using Tissue Fragmentation: Part I and Part II", Ultrasound in Medicine and Biologyl, Jun. 1996, vol. 22 (1), pp. 89-100, and pp. 101-117.
Cimino, "Ultrasonic Surgery: Power Quantification and Efficiency Optimization", Aesthetic Surgery Journal, Feb. 2001, pp. 233-241.
Cowell et al., "A Randomized Trial of Intensive Lipid-Lowering Therapy in Calcific Aortic Stenosis," NEJM, Jun. 2005, vol. 352 (23), pp. 2389-2397.
De Korte et al., "Characterization of Plaque Components and Vulnerability with Intravascular Ultrasound Elastography", Phys. Med. Biol., Feb. 2000, vol. 45, pp. 1465-1475.
European Search Report dated Mar. 13, 2015 for European Application. No. 05853460.3.
Feldman, "Restenosis Following Successful Balloon Valvuloplasty: Bone Formation in Aortic Valve Leaflets", Cathet Cardiovasc Diagn, May 1993, vol. 29 (1), pp. 1-7.
Fitzgerald et al., "Intravascular Sonotherapy Decreased Neointimal Hyperplasia After Stent Implantation in Swine", Circulation, Feb. 2001, vol. 103, pp. 1828-1831.
Freeman et al., "Ultrasonic Aortic Valve Decalcification: Serial Doppler Echocardiographic Follow Up", J Am Coll Cardiol., Sep. 1990, vol. 16 (3), pp. 623-630.
Greenleaf et al., "Selected Methods for Imaging Elastic Properties of Biological Tissues", Annu. Rev. Biomed. Eng., Apr. 2003, vol. 5, pp. 57-78.
Gunn et al., "New Developments in Therapeutic Ultrasound-Assisted Coronary Angioplasty", Curr Interv Cardiol Rep., Dec. 1990, vol. 1 (4), pp. 281-290.
Guzman et al., "Bioeffects Caused by Changes in Acoustic Cavitation Bubble Density and Cell Concentration: A Unified Explanation Based on Cell-to-Bubble Ratio and Blast Radius", Ultrasound in Med. & Biol., Mar. 2003, vol. 29 (8), pp. 1211-1222.
Hallgrimsson et al., "Chronic Non-Rheumatic Aortic Valvular Disease: a Population Study Based on Autopsies", J Chronic Dis., Jun. 1979, vol. 32 (5), pp. 355-363.
Isner et al., "Contrasting Histoarchitecture of Calcified Leaflets from Stenotic Bicuspid Versus Stenotic Tricuspid Aortic Valves", J Am Coll Cardiol., Apr. 1990, vol. 15 (5), p. 1104-1108.
Lung et al., "A Prospective Survey of Patients with Valvular Heart Disease in Europe: The Euro Heart Survey on Valvular Heart Disease", Euro Heart Journal, Mar. 2003, vol. 24, pp. 1231-1243.
Mcbride et al "Aortic Valve Decalcification", J Thorac Cardiovas-Surg, Jul. 1990, vol. 100, pp. 36-42.
Miller et al., "Lysis and Sonoporation of Epidermoid and Phagocytic Monolayer Cells by Diagnostic Ultrasound Activation of Contrast Agent Gas Bodies", Ultrasound in Med. & Biol., May 2007, vol. 27 (8), pp. 1107-1113.
Mohler, "Mechanisms of Aortic Valve Calcificaion", Am J Cardiol, Dec. 2004, vol. 94(11), pp. 1396-1402.
Otto et al., "Three-Year Outcome After Balloon Aortic Valvuloplasty. Insights into Prognosis of Valvular Aortic Stenosis", Circulation, Feb. 1994, vol. 89, pp. 642-650.
Passik et al., "Temporal Changes in the Causes of Aortic Stenosis: A Surgical Pathologic Study of 646 Cases", Mayo Clin Proc, Feb. 1987, vol. 62, pp. 19-123.
Quaden et al., "Percutaneous Aortic Valve Replacement: Resection Before Implantation", Eur J Cardiothorac Surg, Jan. 2005, vol. 27, pp. 836-840.
Riebman et al., "New Concepts in the Management of Patients with Aortic Valve Disease", Abstract, Valvular Heart Disease, JACC, Mar. 2004, p. 34A.
Rosenschein et al., "Percutaneous Transluminal Therapy of Occluded Saphenous Vein Grafts" Circulation, Jan. 1999, vol. 99, pp. 26-29.
Sakata et al., "Percutaneous Balloon Aortic Valvuloplasty: Antegrade Transseptal vs. Conventional Retrograde Transarterial Approach", Catheter Cardiovasc Interv., Mar. 2005, vol. 64 (3), pp. 314-321.
Sasaki et al., "Scanning Electron Microscopy and Fourier Transformed Infrared Spectroscopy Analysis of Bone Removal Using Er:YAG and CO2 Lasers", J Periodontol., Jun. 2002, vol. 73(6), pp. 643-652.
Search Report and Written Opinion dated Dec. 10, 2012 for PCT Application No. PCT/US2012/043636.
Search Report and Written Opinion dated Dec. 6, 2016 for PCT Application No. PCT/US2016/047831.
Search Report and Written Opinion dated Mar. 2, 2015 for PCT Application No. PCT/US2014/029549.
Search Report and Written Opinion dated May 1, 2012 for PCT Application No. PCT/US2011/065627.
Search Report and Written Opinion dated May 22, 2007 for PCT Application No. PCT/US2005/044543.
Search Report and Written Opinion dated Oct. 20, 2014 for PCT Application No. PCT/US2014/038849.
Search Report and Written Opinion dated Sep. 4, 2014 for PCT Application No. PCT/US2014/014704.
The CoreValve System Medtronic, 2012, 4 Pages.
Van Den Brand et al., "Histological Changes in the Aortic Valve after Balloon Dilation: Evidence for a Delayed Healing Process", Br Heart J, Jun. 1992, vol. 67, pp. 445-459.
Verdaasdonk et al., "The Mechanism of Action of the Ultrasonic Tissue Resectors Disclosed Using High-Speed and Thermal Imaging Techniques", SPIE, Jan. 1999, vol. 3594, pp. 221-231.
Voelker et al., "Inoperative Valvuloplasty in Calcific Aortic Stenosis: a Study Comparing the Mechanism of a Novel Expandable Device with Conventional Balloon Dilation", Am Heart J., Nov. 1991, vol. 122 (5), pp. 1327-1333.

(56) References Cited

OTHER PUBLICATIONS

Waller et al., "Catheter Balloon Valvuloplasty of Stenotic Aortic Valves. Part II: Balloon Valvuloplasty During Life Subsequent Tissue Examination", Clin Cardiol., Nov. 1991, vol. 14 (11), pp. 924-930.
Wang, "Balloon Aortic Valvuloplasty", Prog Cardiovasc Dis., Jul.-Aug. 1997, vol. 40 (1), pp. 27-36.
Wilson et al., "Elastography—The movement Begins", Phys. Med. Biol., Jun. 2000, vol. 45, pp. 1409-1421.
Yock et al., "Catheter-Based Ultrasound Thrombolysis", Circulation, Mar. 1997, vol. 95 (6), pp. 1411-1416.
International Search Report and Written Opinion dated Jul. 11, 2018 for PCT Application No. PCT/US2018/027990.
International Search Report and Written Opinion dated Jun. 28, 2018 for PCT Application No. PCT/US2018/027983.
International Search Report and Written Opinion dated Aug. 3, 2018 for PCT Application No. PCT/US2018035086.
International Search Report and Written Opinion dated Aug. 9, 2018 for PCT Application No. PCT/US2018/035081.
International Search Report and Written Opinion dated Sep. 4, 2018 for PCT Application No. PCT/US2018/027966, 17 pages.
International Search Report and Written Opinion dated Sep. 11, 2018 for PCT Application No. PCT/US2018/038847, 18 pages.
International Search Report and Written Opinion dated Jul. 3, 2018 for PCT Application No. PCT/US2018/031438, 14 pages.
International Search Report and Written Opinion dated Sep. 11, 2018 for PCT Application No. PCT/US2018/038841, 15 pages.
Notice of Reasons for Rejection dated Feb. 22, 2021 in Japanese Patent Application No. 2020-033472, with translation, 11 pages.
International Preliminary Report on Patentability from International Application No. PCT/US2012/043636, issued Dec. 23, 2013, 16 pp.
Communication Pursuant to Rules 161(1) and 162 EPC dated Feb. 20, 2014 from counterpart European Application No. 12802492.4, 3 pp.
Response to Communication pursuant to Rules 161(1) and 162 EPC dated Feb. 20, 2014, from counterpart European Application No. 12802492.4, filed Aug. 26, 2014, 4 pp.
Extended Search Report from counterpart European Application No. 12802492.4, dated Nov. 3, 2014, 6 pp.
Response to Extended Search Report dated Nov. 3, 2014, from counterpart European Application No. 12802492.4, filed May 29, 2015, 15 pp.
Examination Report from counterpart European Application No. 12802492.4, dated Jul. 6, 2017, 4 pp.
Response to Examination Report dated Jul. 6, 2017, from counterpart European Application No. 12802492.4, filed Nov. 15, 2017, 24 pp.

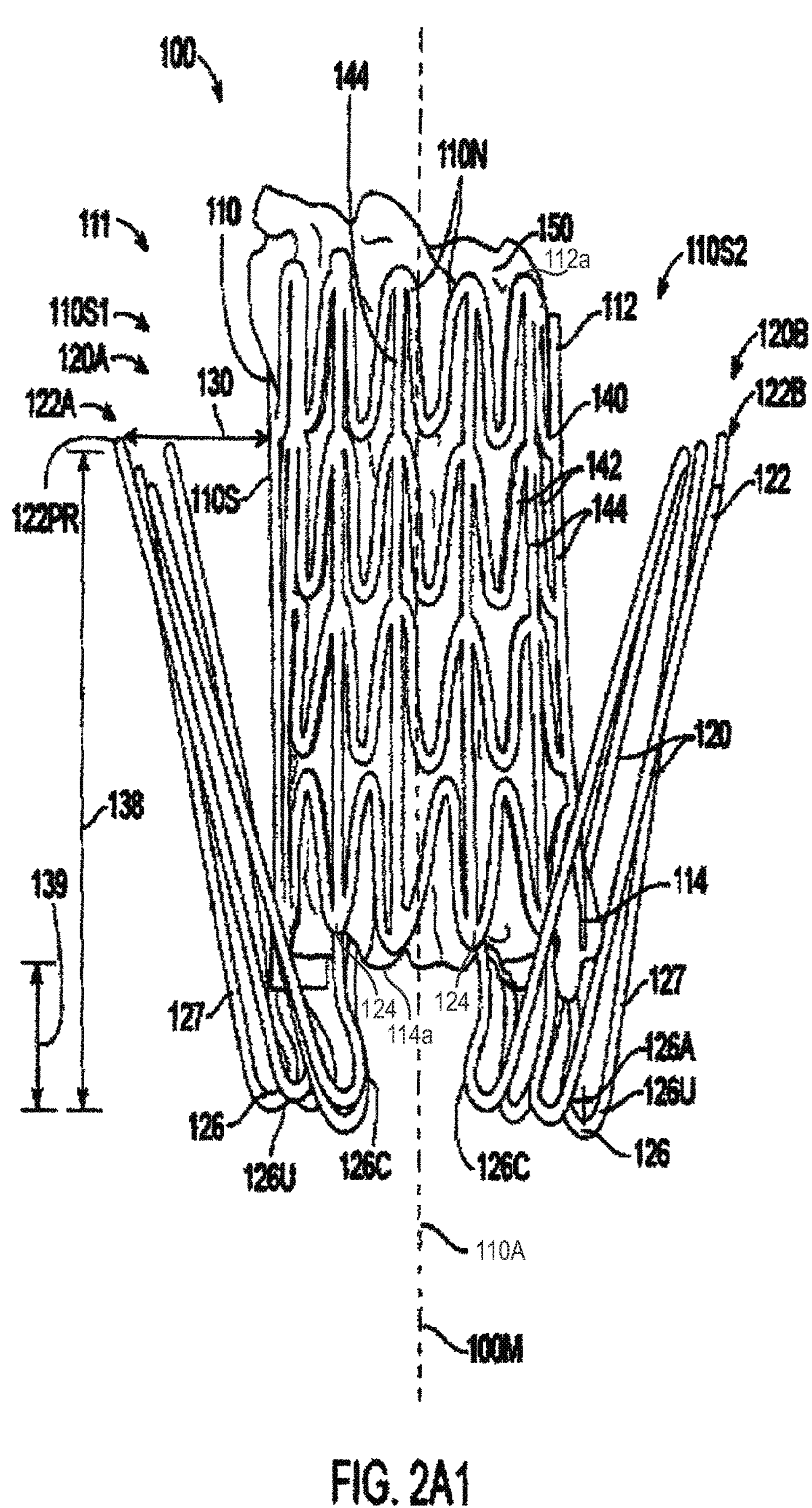
FIG. 2A1

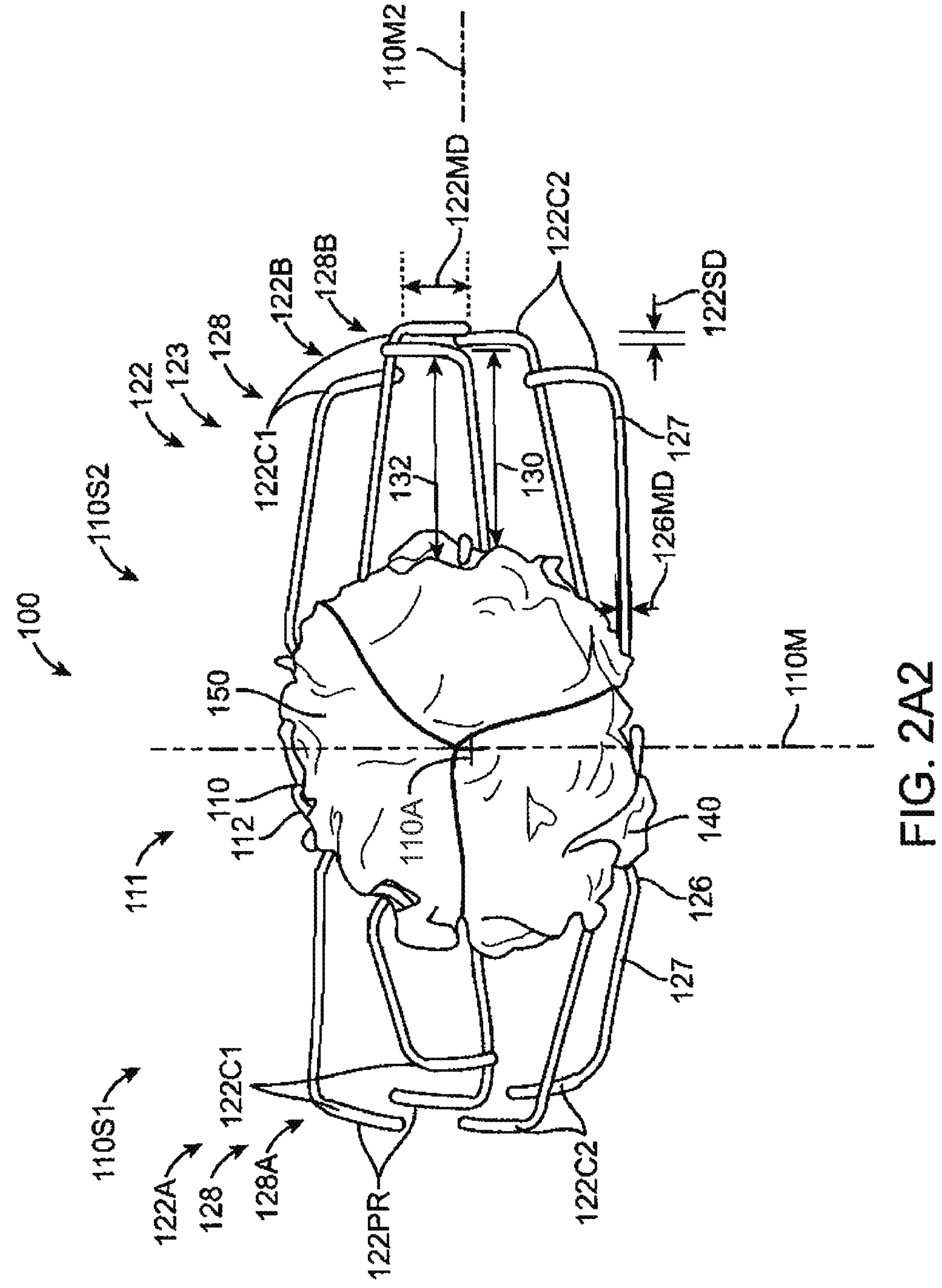
FIG. 2A2

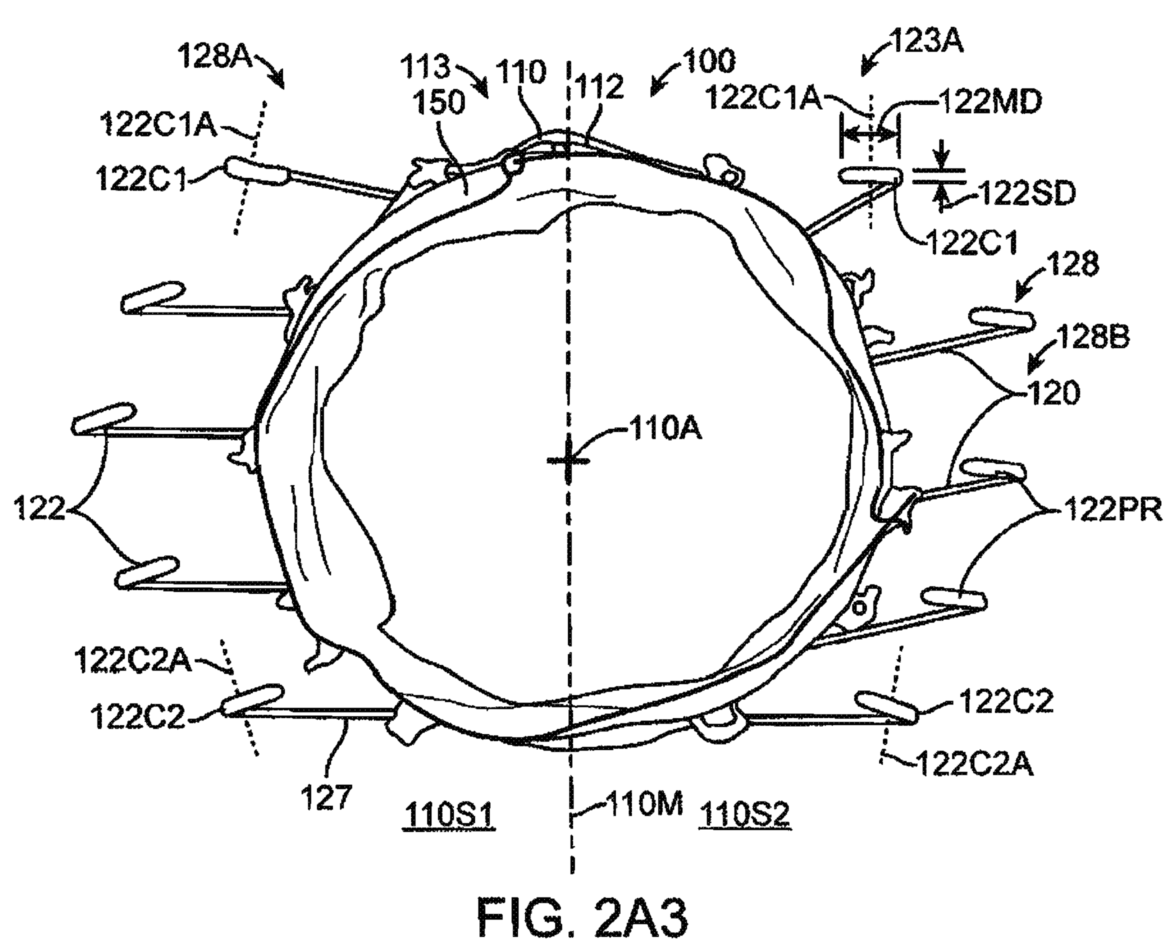
FIG. 2A3
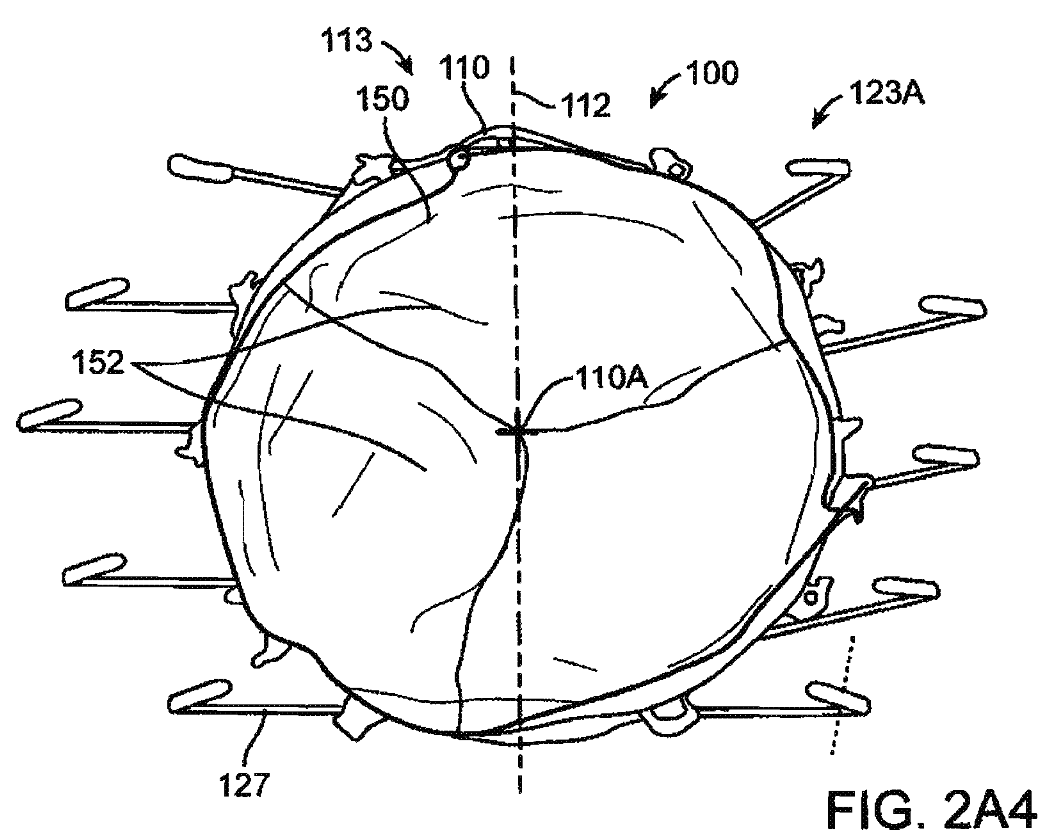
FIG. 2A4

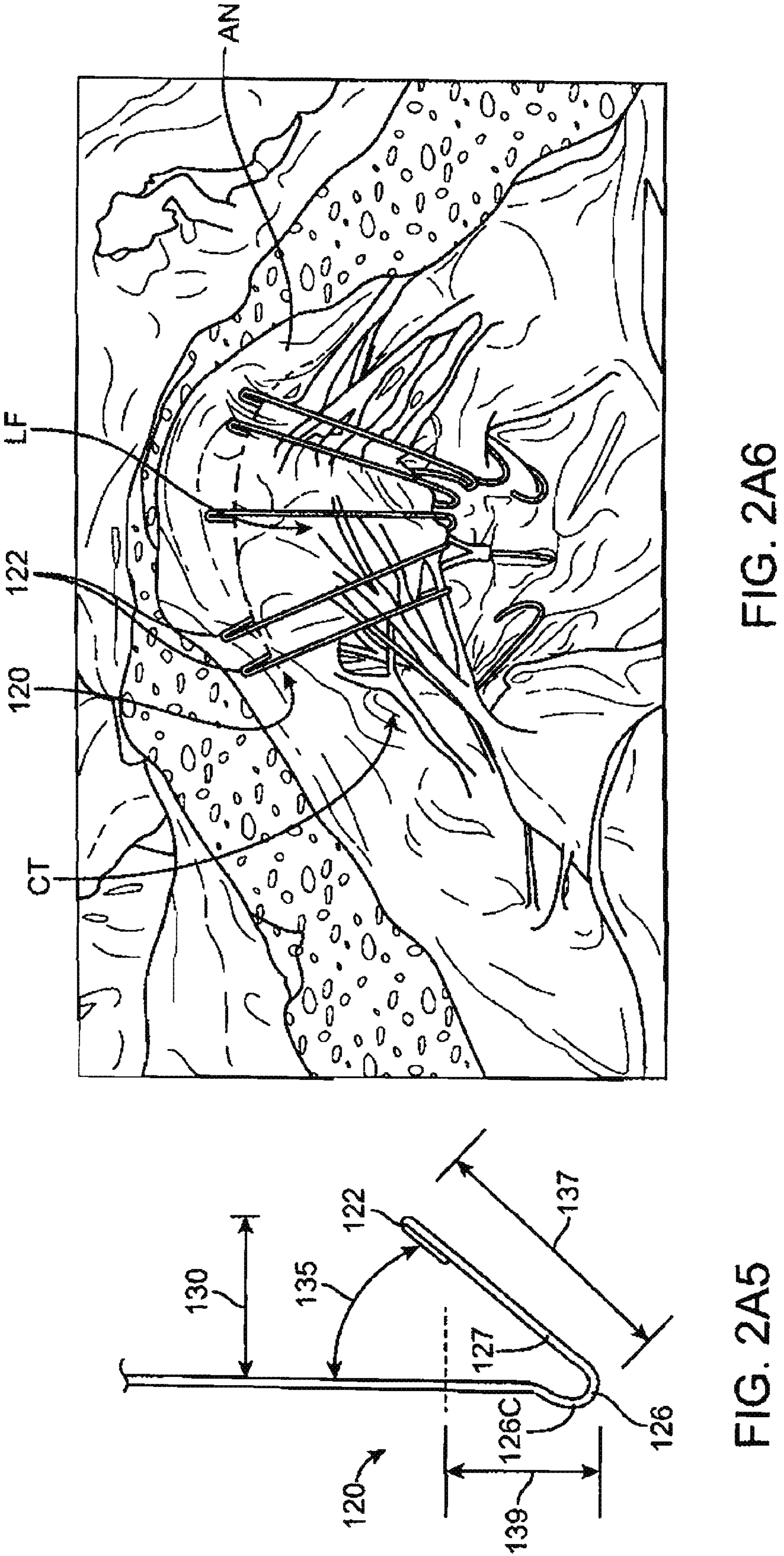
FIG. 2A6
FIG. 2A5

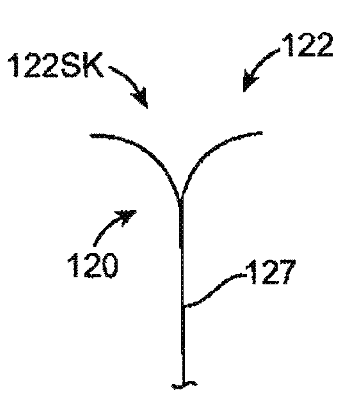
FIG. 2A7A
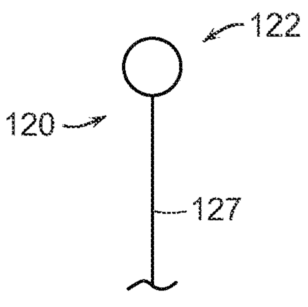
FIG. 2A7B
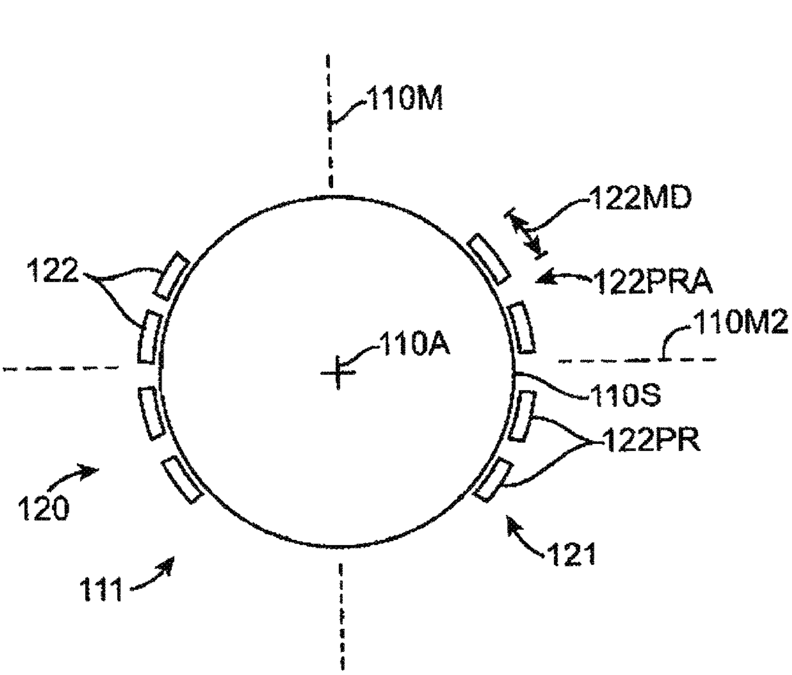
FIG. 2A8
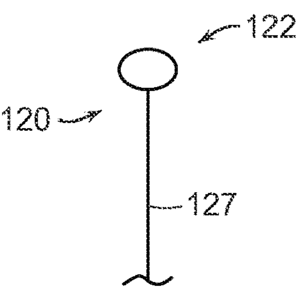
FIG. 2A7C
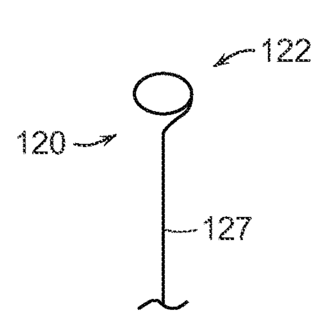
FIG. 2A7D
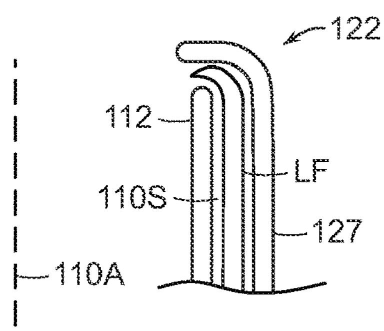
FIG. 2A7E

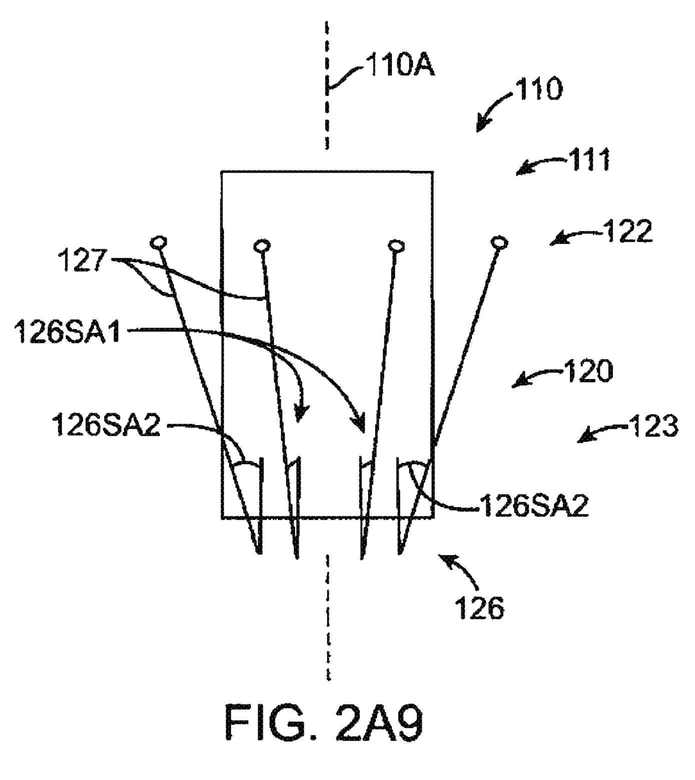
FIG. 2A9
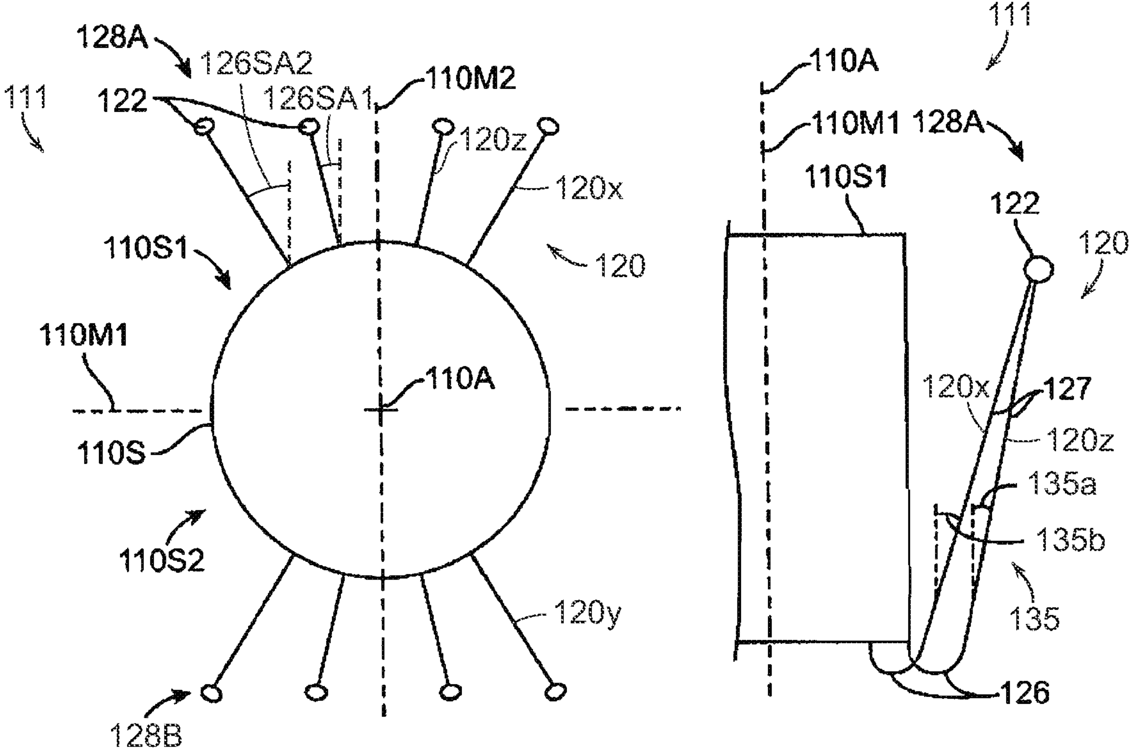
FIG. 2A10
FIG. 2A11

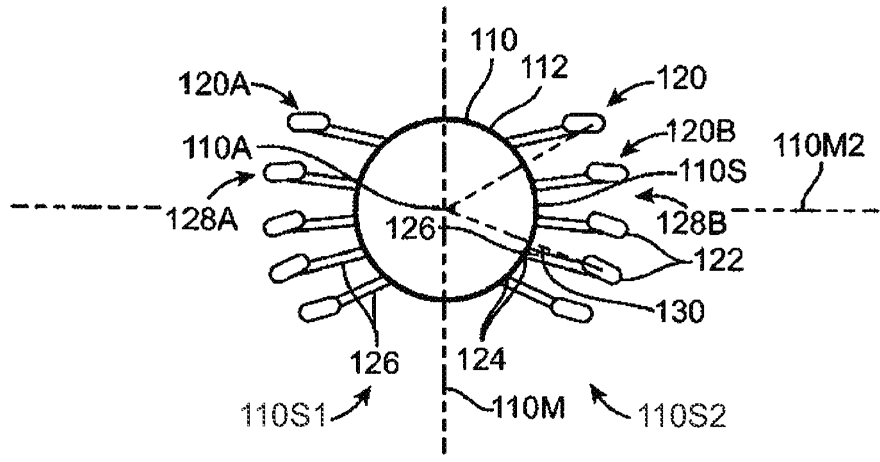
FIG. 2C1
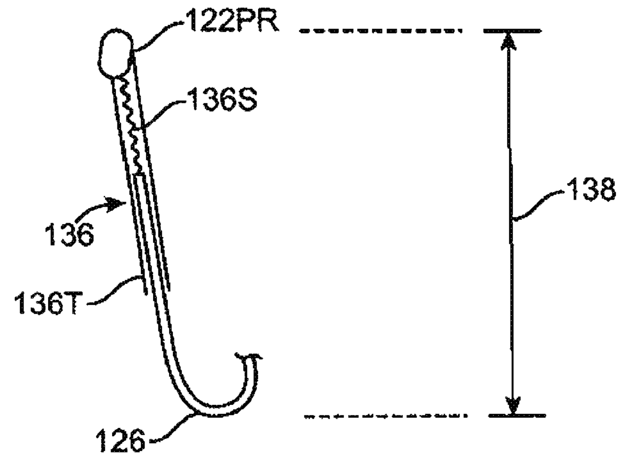
FIG. 2C2

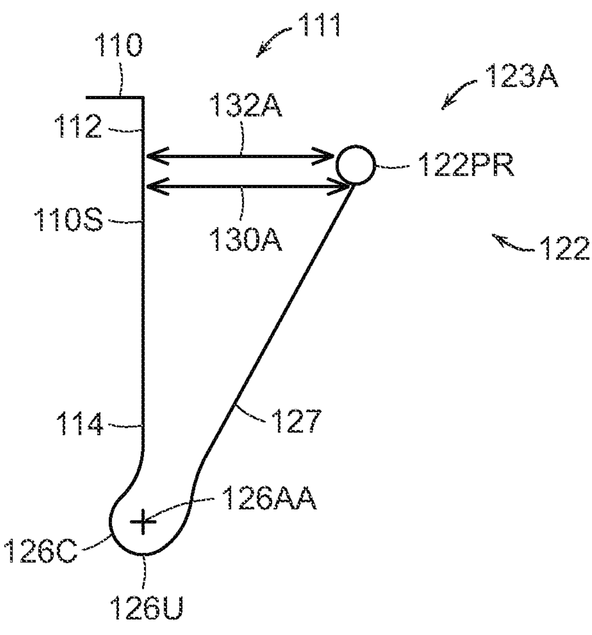
FIG. 2C3
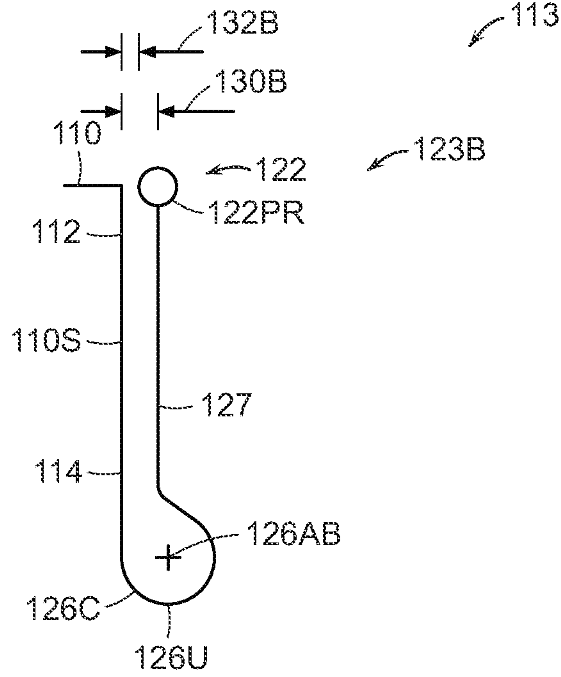
FIG. 2C4

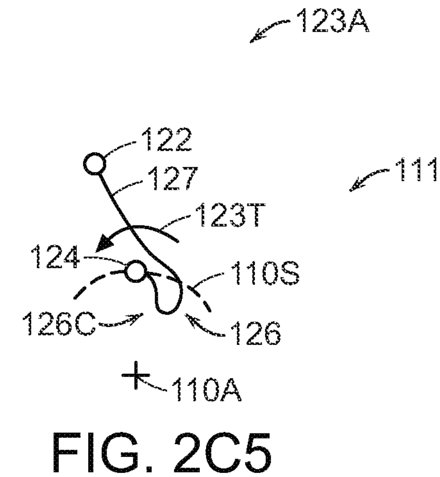
FIG. 2C5
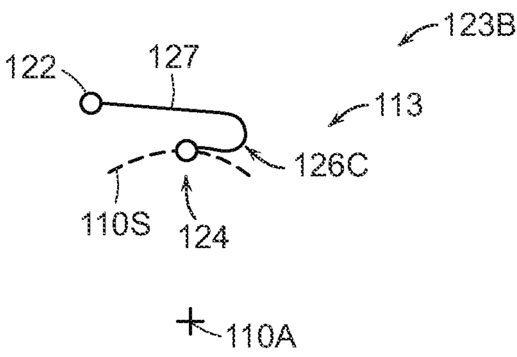
FIG. 2C6

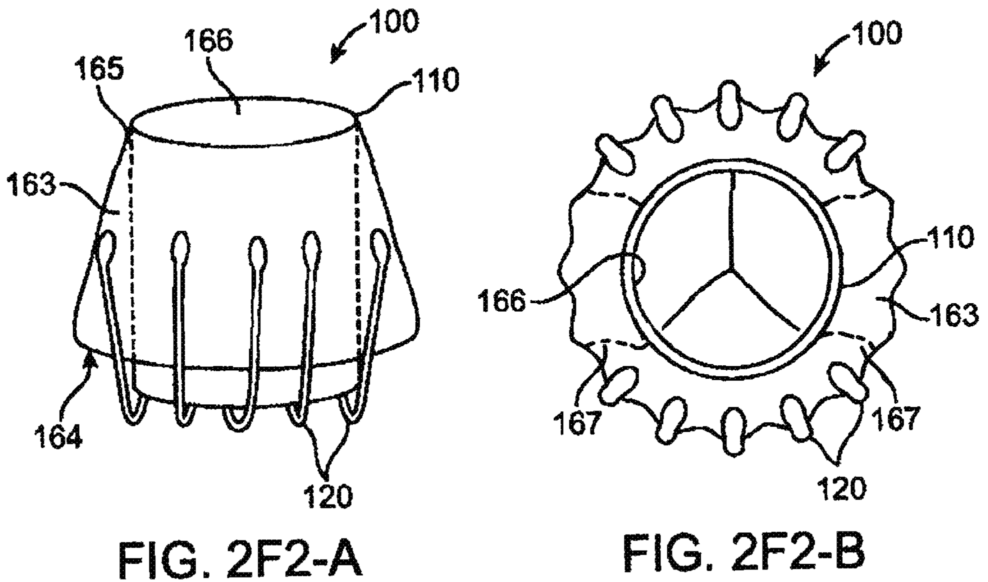
FIG. 2F2-A
FIG. 2F2-B

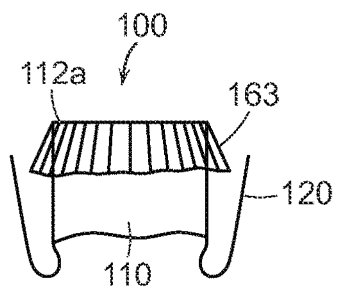
FIG. 2F3-A
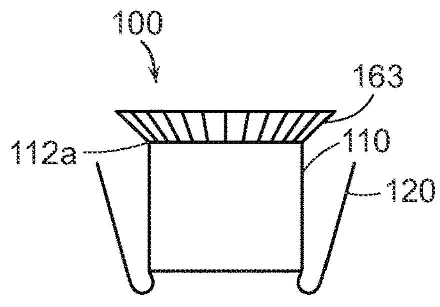
FIG. 2F3-B
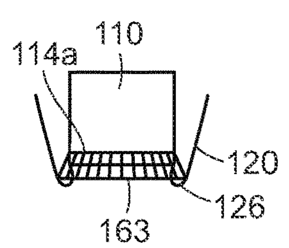
FIG. 2F4-A
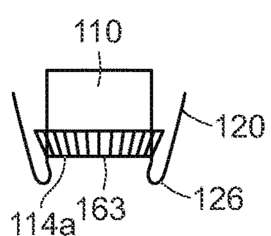
FIG. 2F4-B
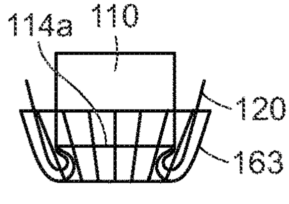
FIG. 2F4-C
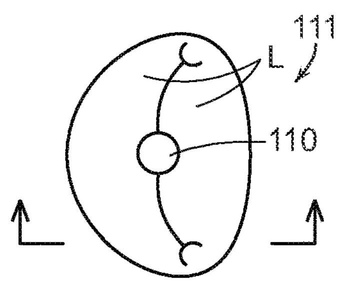
FIG. 2F5A
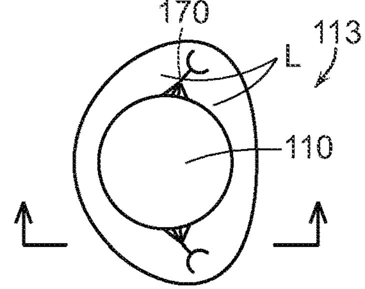
FIG. 2F5C
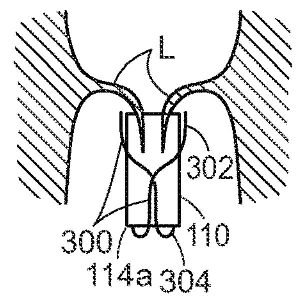
FIG. 2F5B
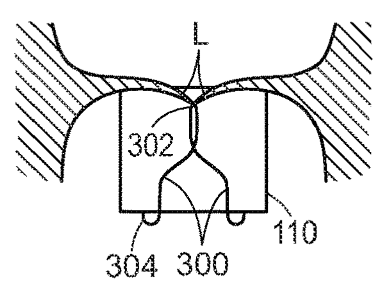
FIG. 2F5D

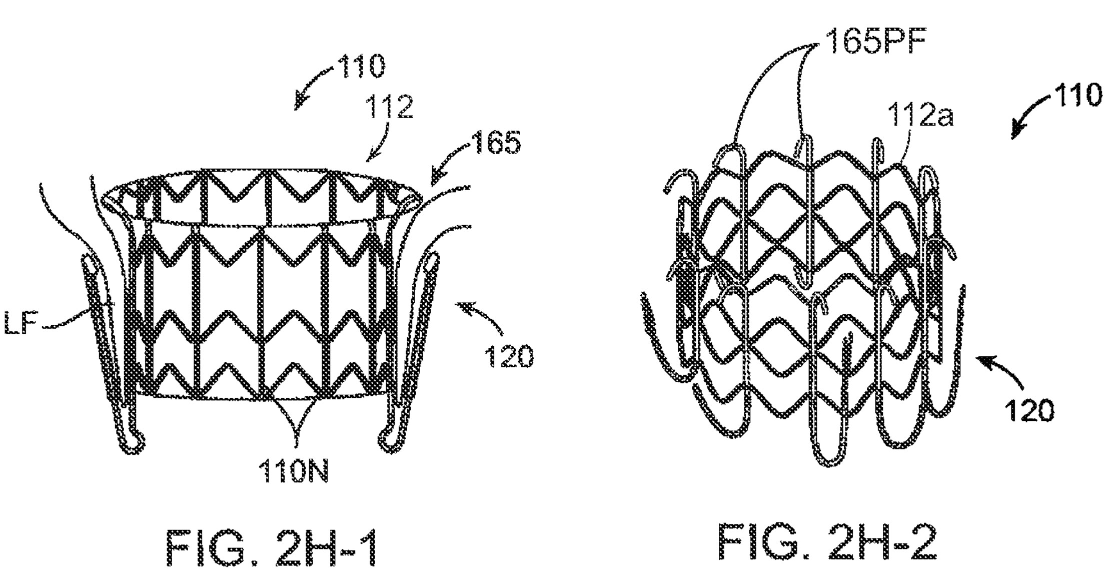
FIG. 2H-1
FIG. 2H-2
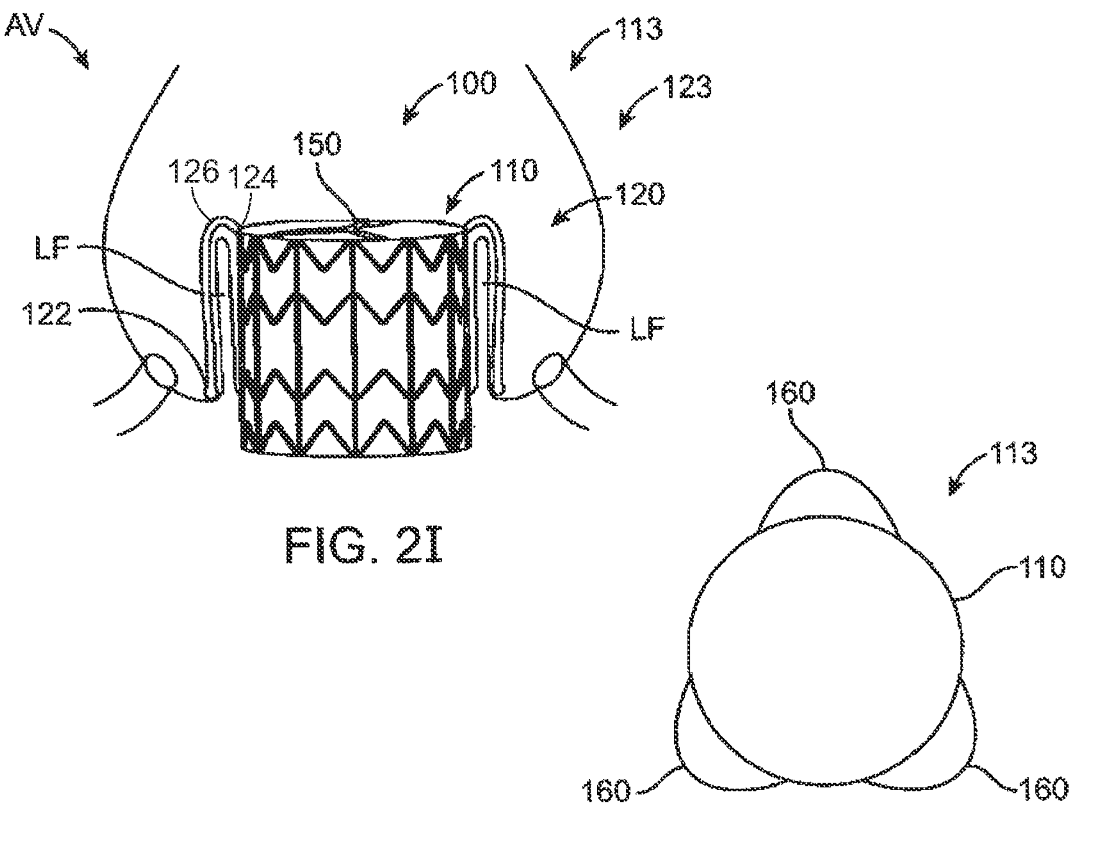
FIG. 2I
FIG. 2J 120
121
111
110
100

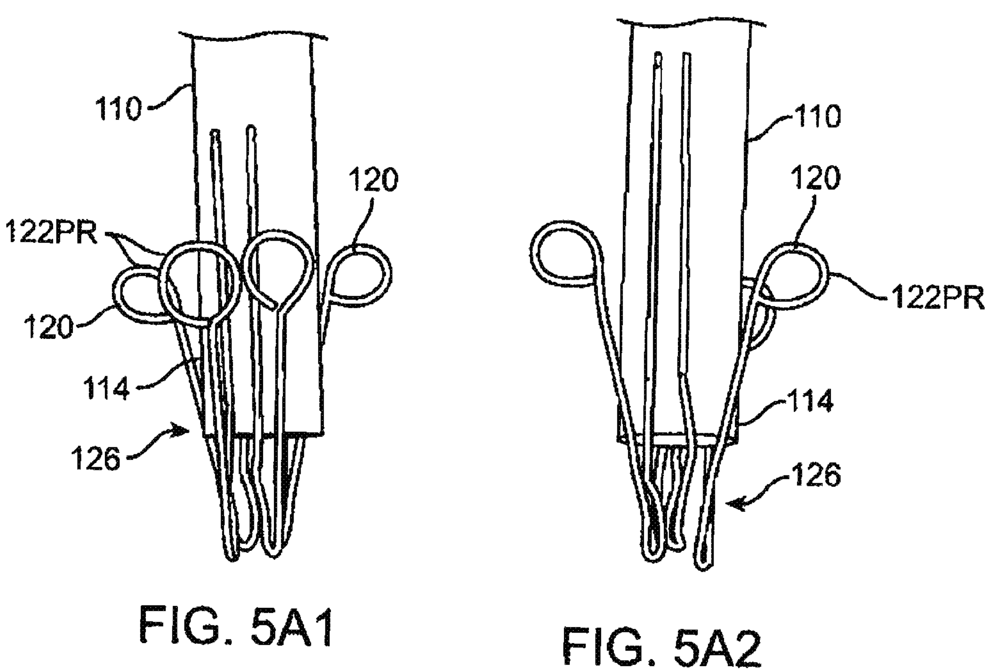
FIG. 5A1
FIG. 5A2
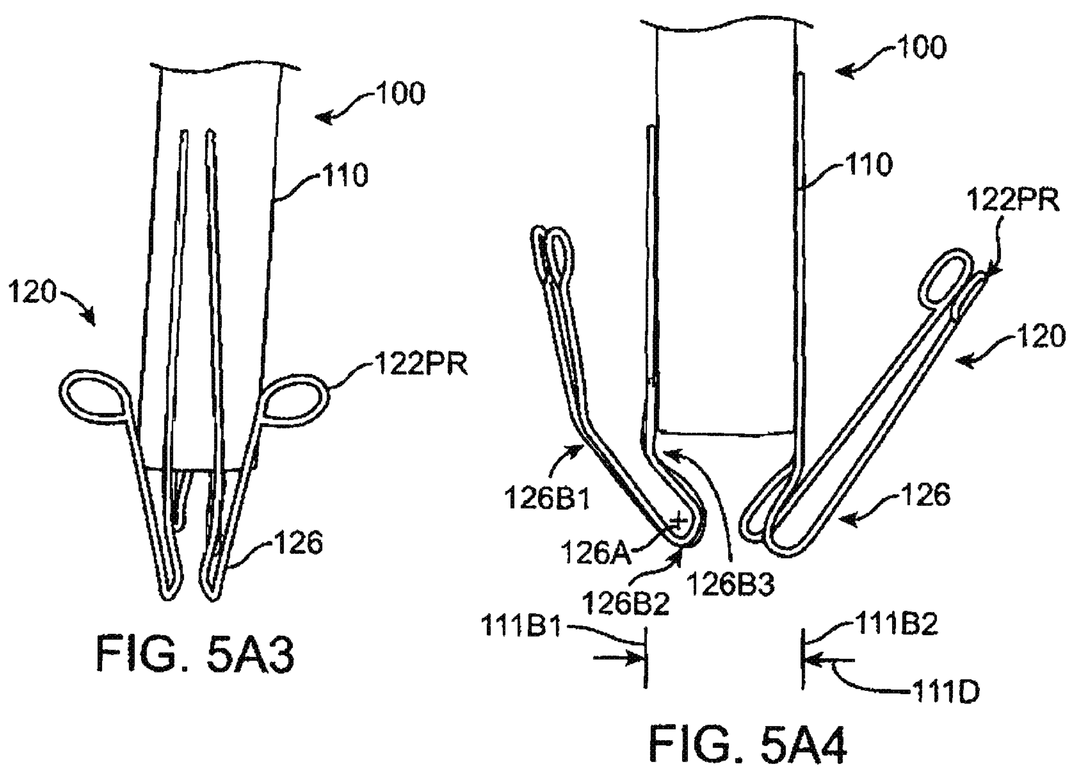
FIG. 5A3
FIG. 5A4

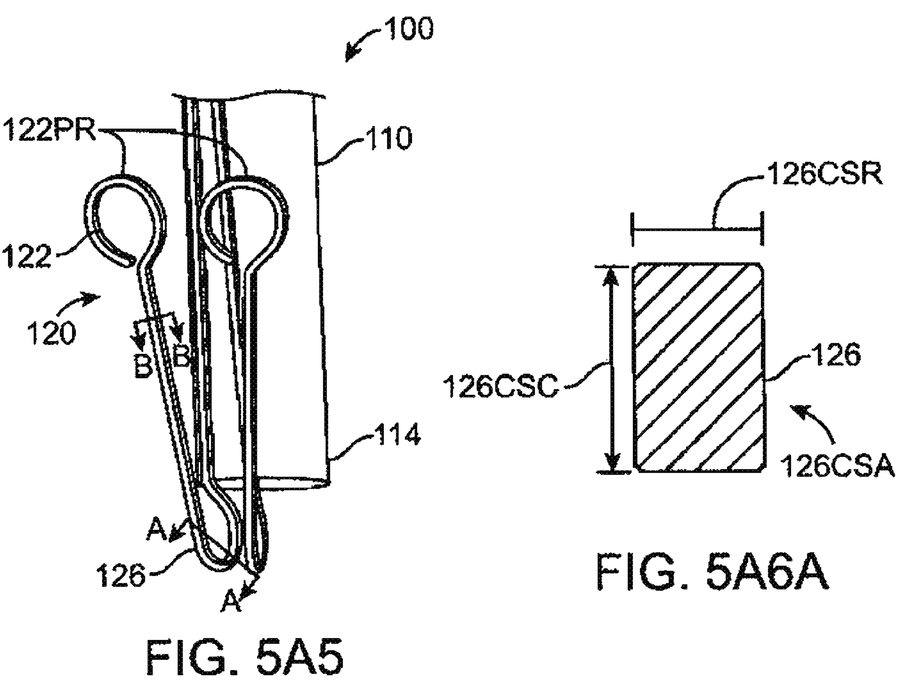
FIG. 5A5
FIG. 5A6A
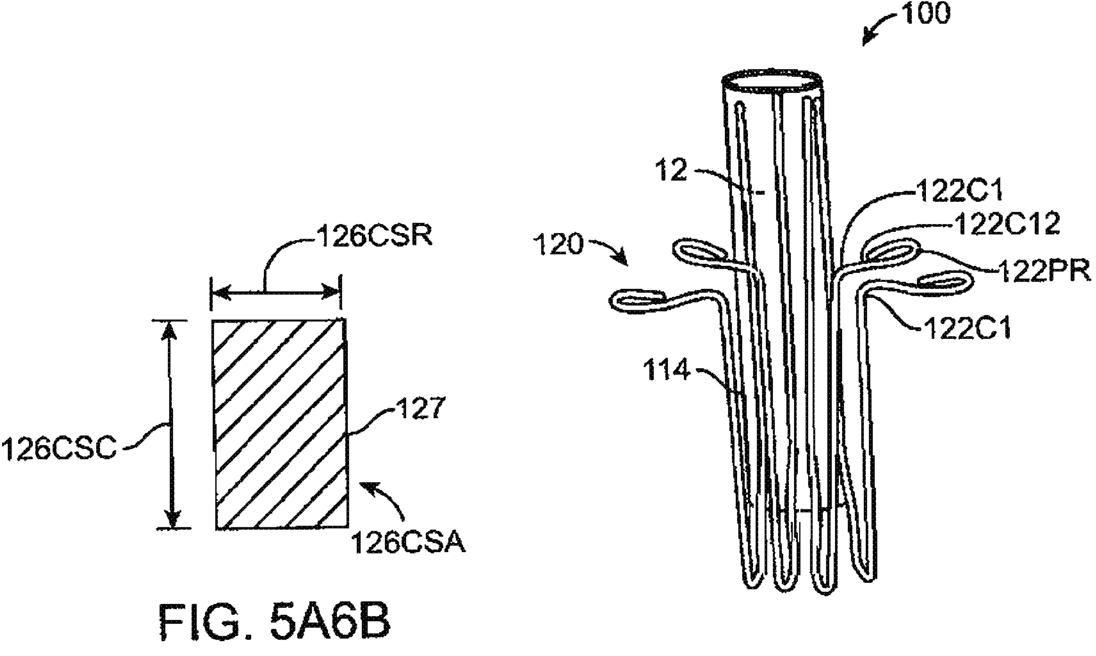
FIG. 5A6B
FIG. 5A7

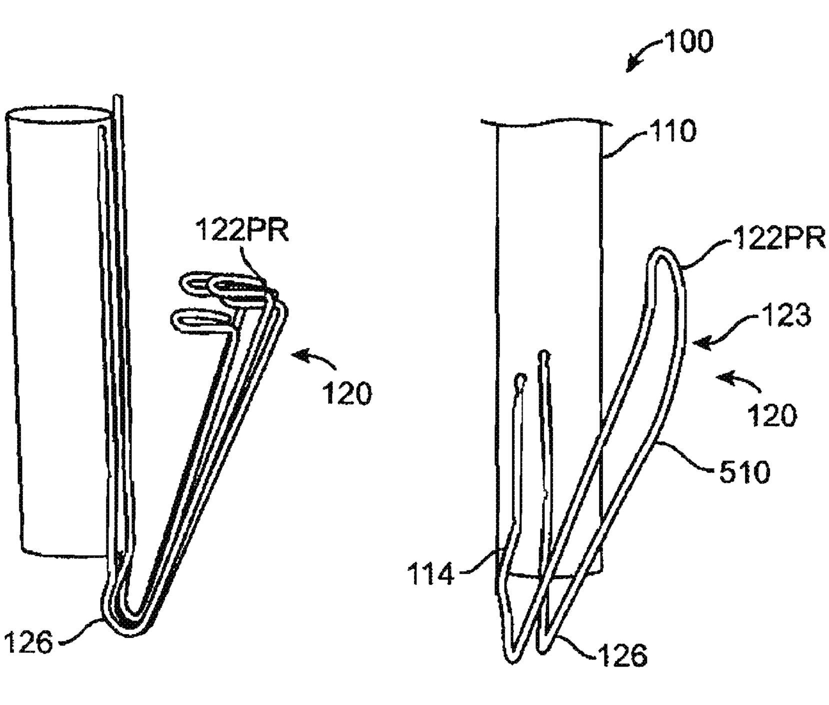
FIG. 5A8
FIG. 5A9
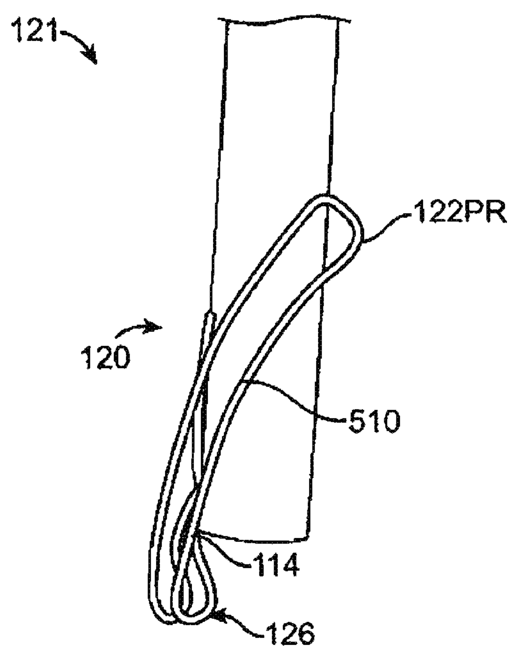
FIG. 5A10

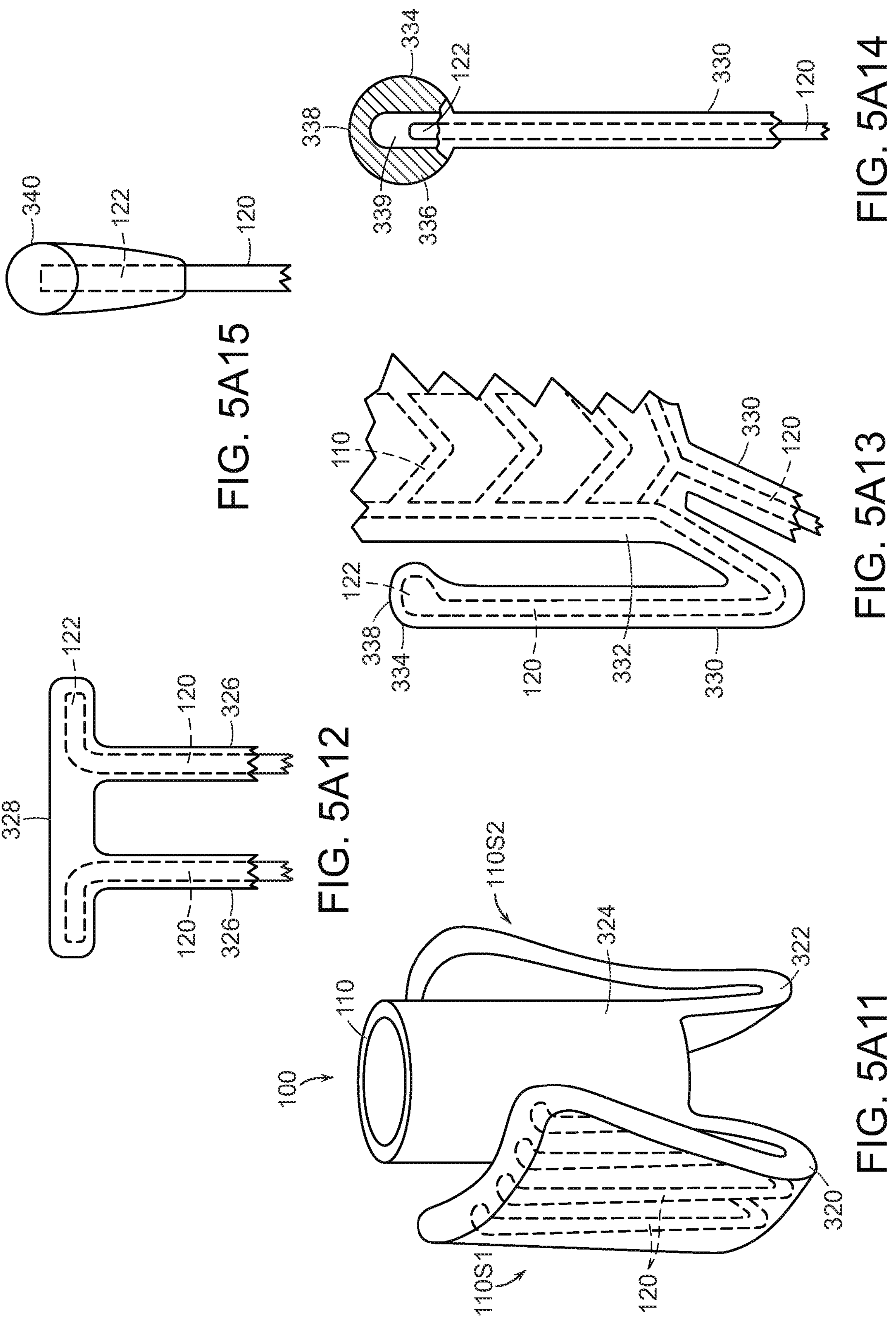
FIG. 5A14
FIG. 5A15
FIG. 5A13
FIG. 5A12
FIG. 5A11

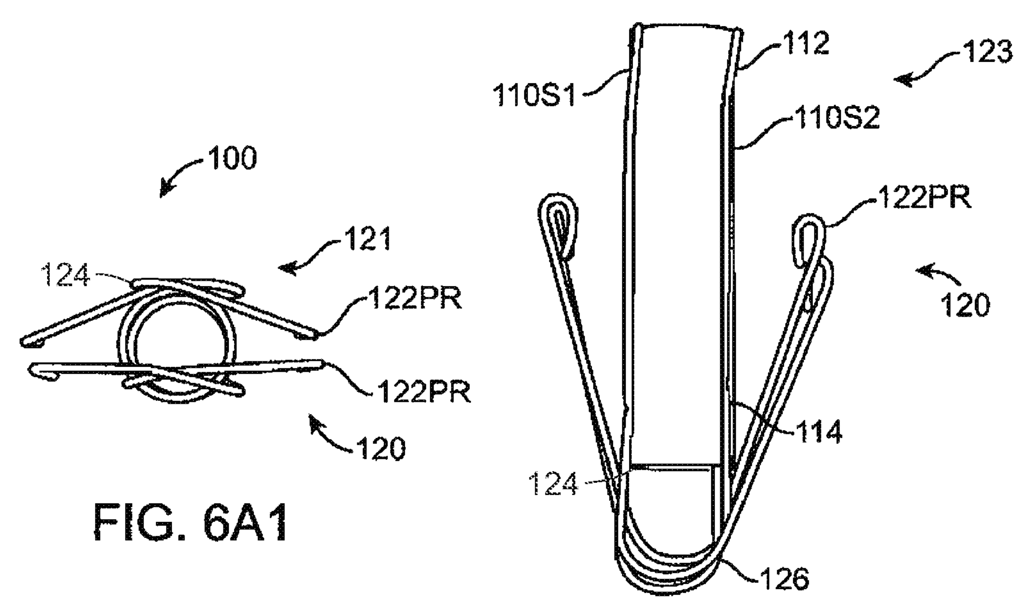
FIG. 6A1
FIG. 6A2
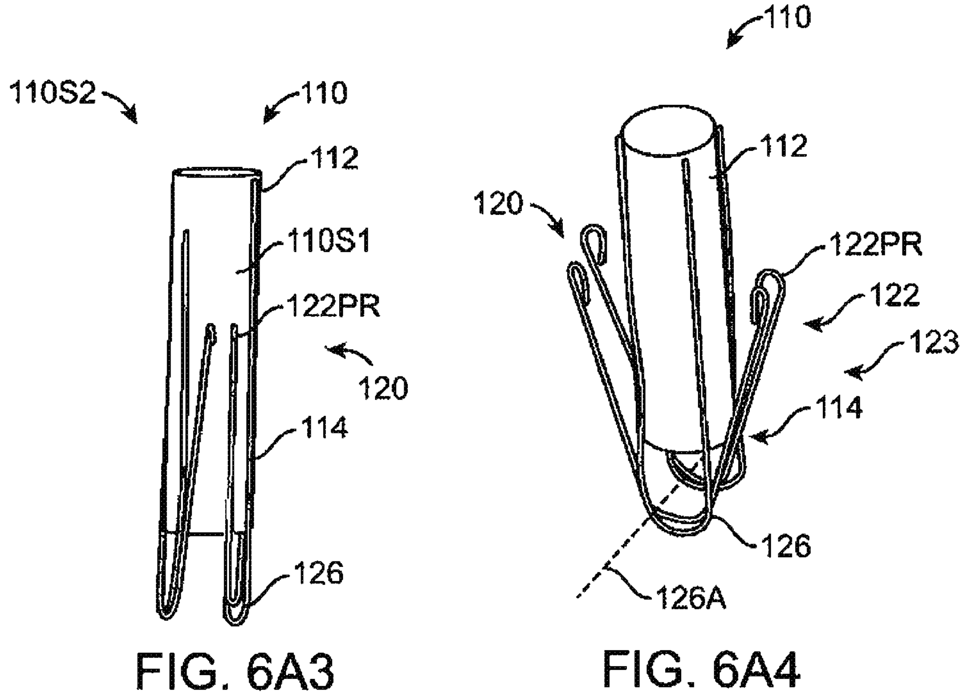
FIG. 6A3
FIG. 6A4

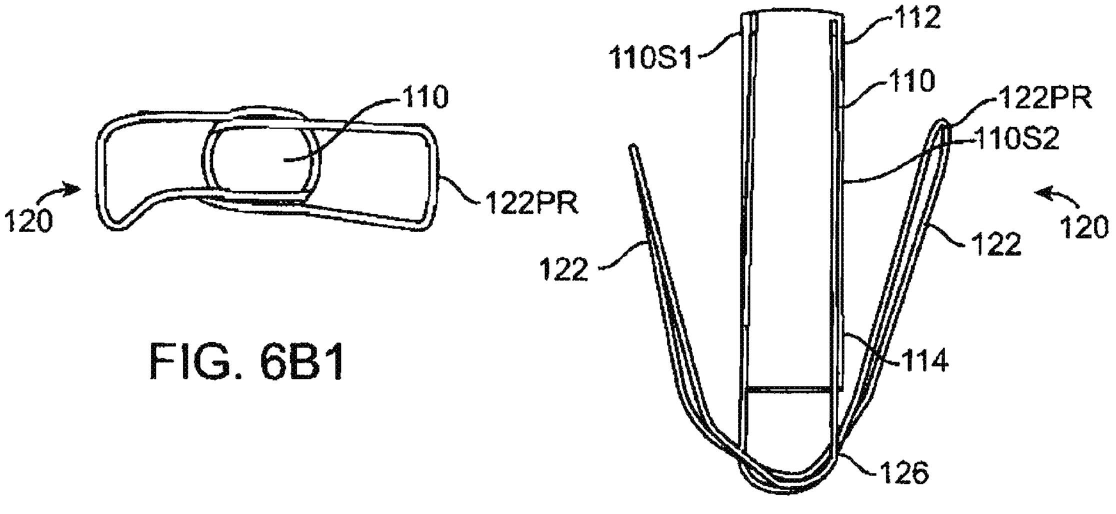
FIG. 6B1
FIG. 6B2
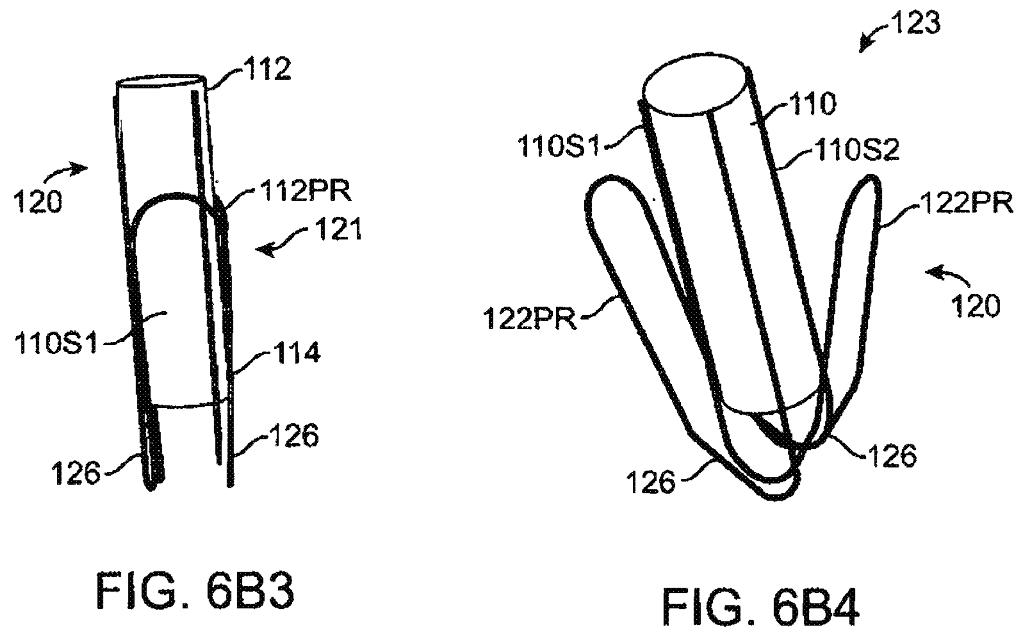
FIG. 6B3
FIG. 6B4

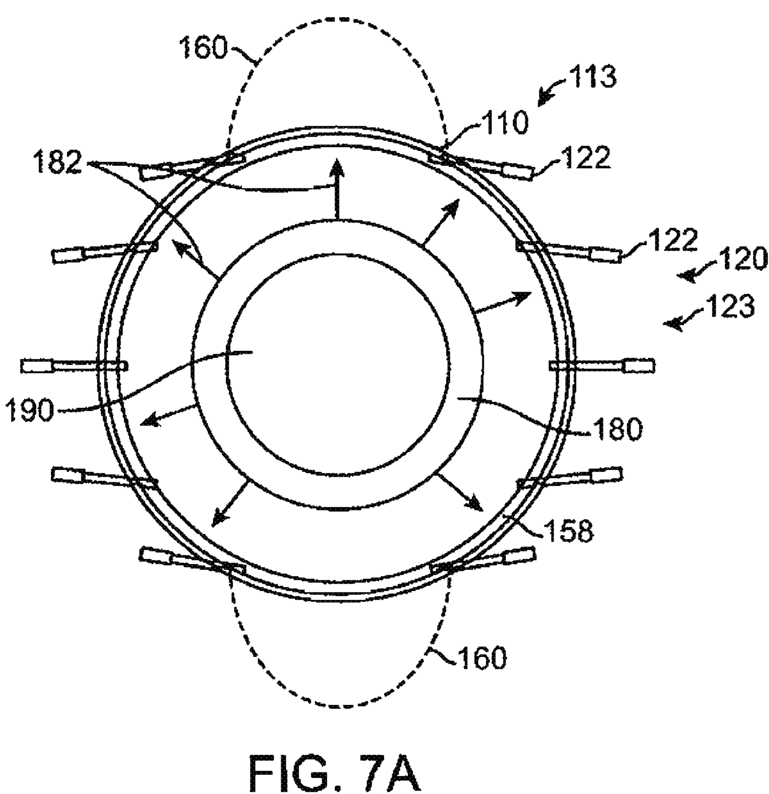
FIG. 7A
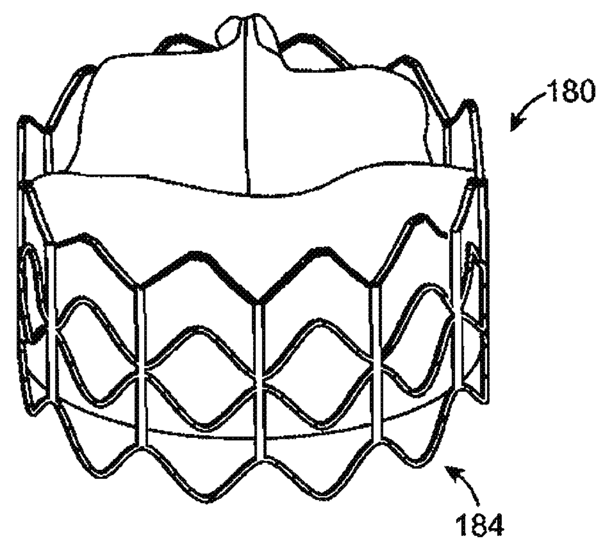
FIG. 7A1

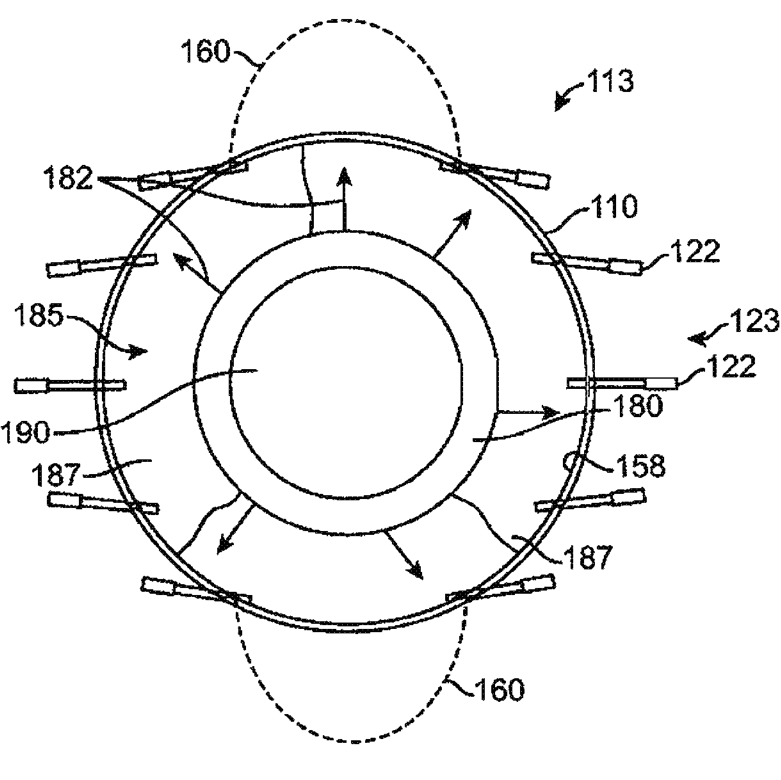
FIG. 7B
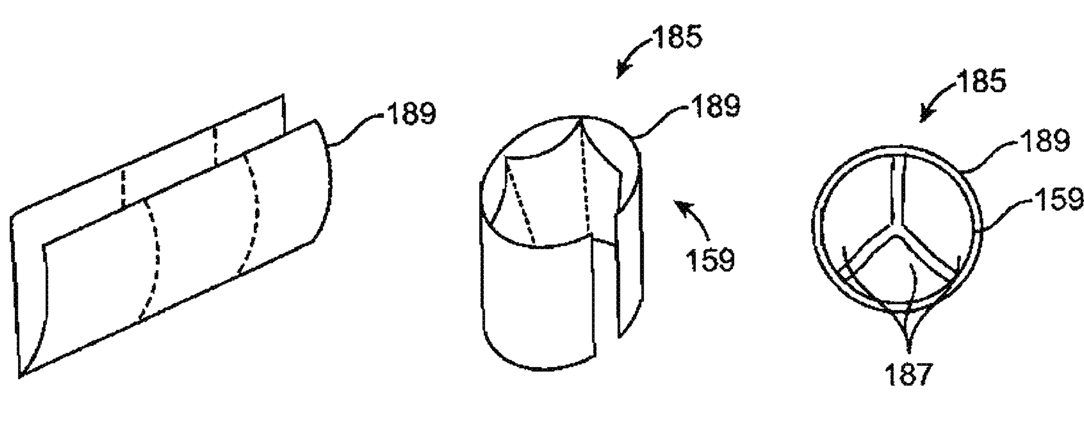
FIG. 7B1
FIG. 7B2
FIG. 7B3

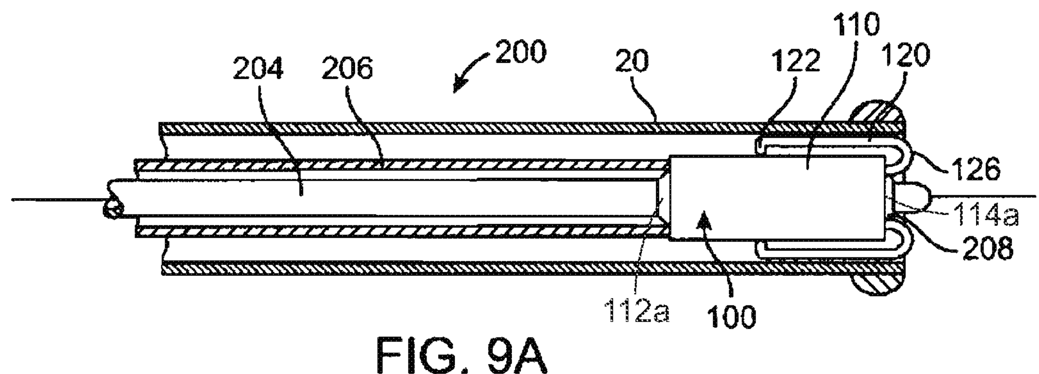
FIG. 9A
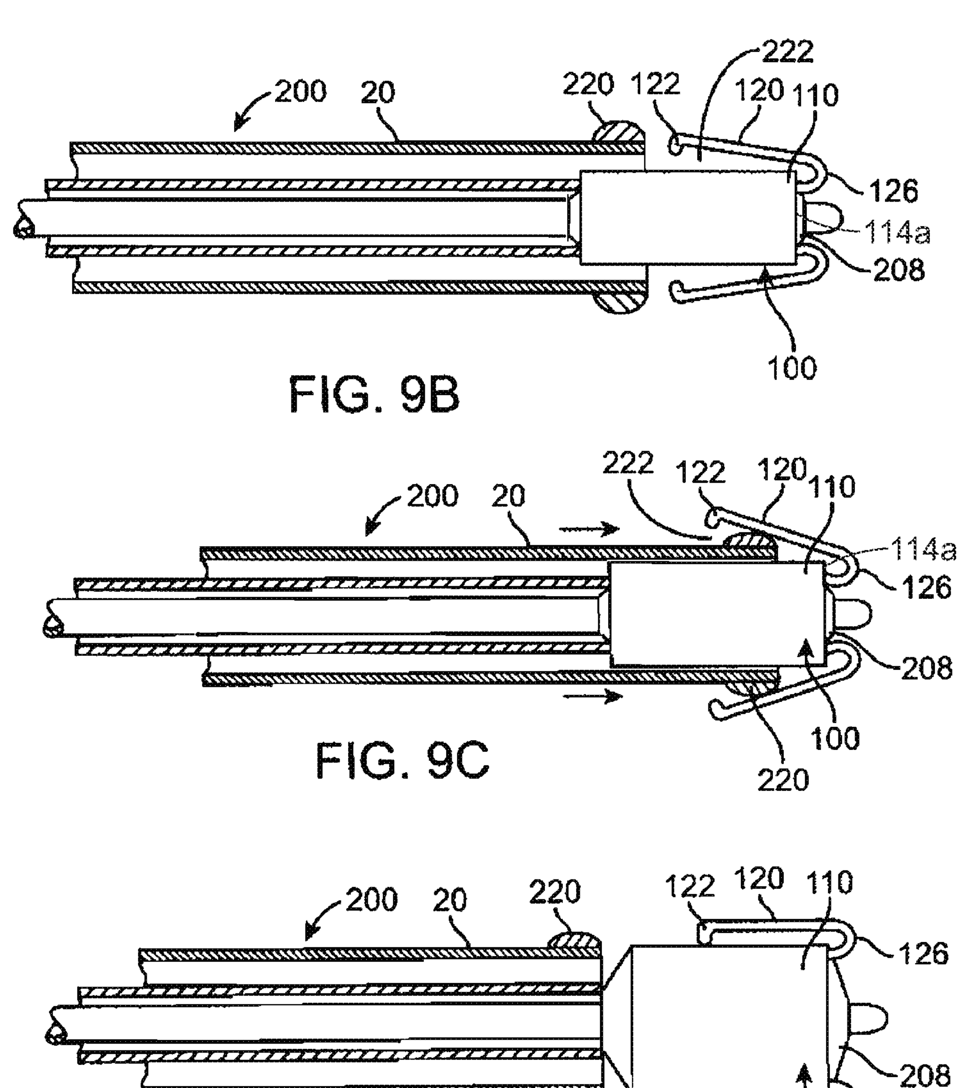
FIG. 9B
FIG. 9C
FIG. 9D

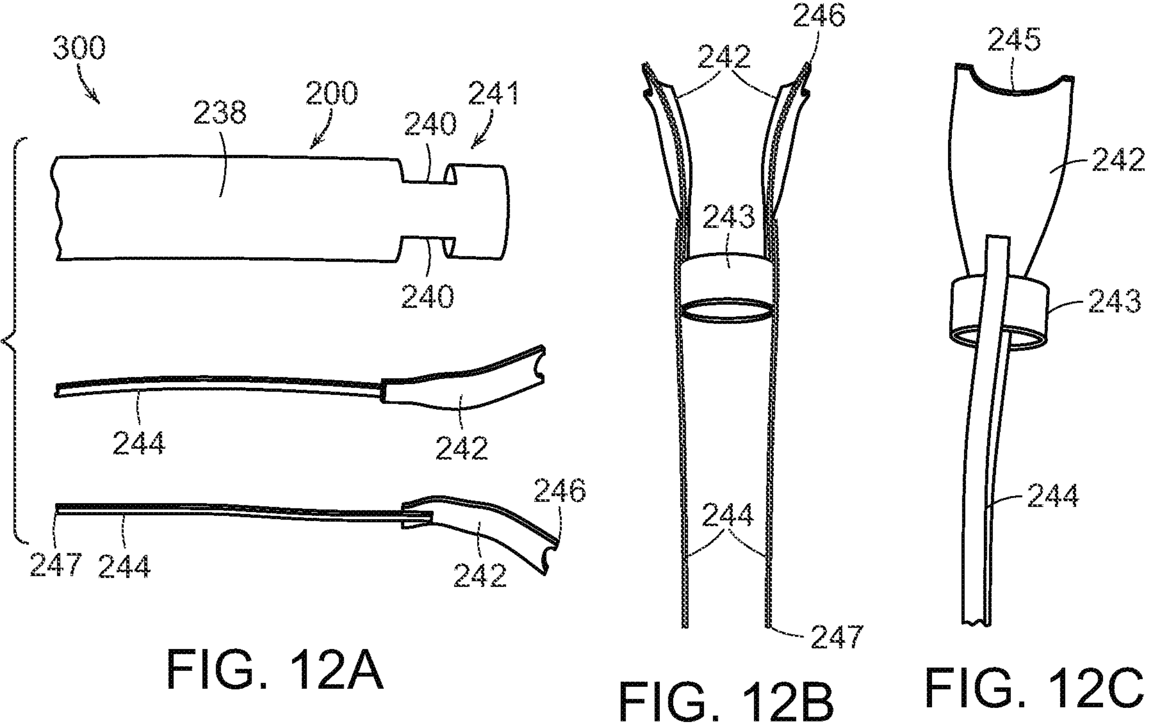
FIG. 12A
FIG. 12B
FIG. 12C
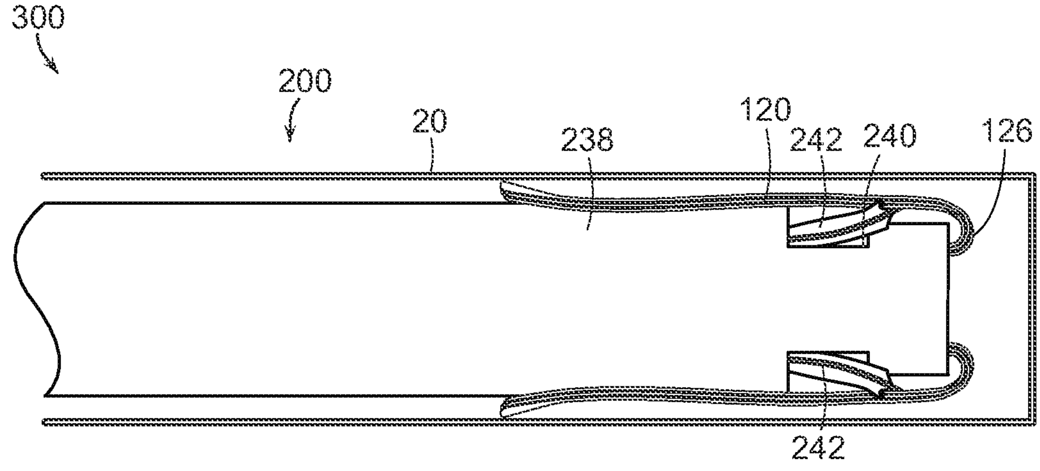
FIG. 12D

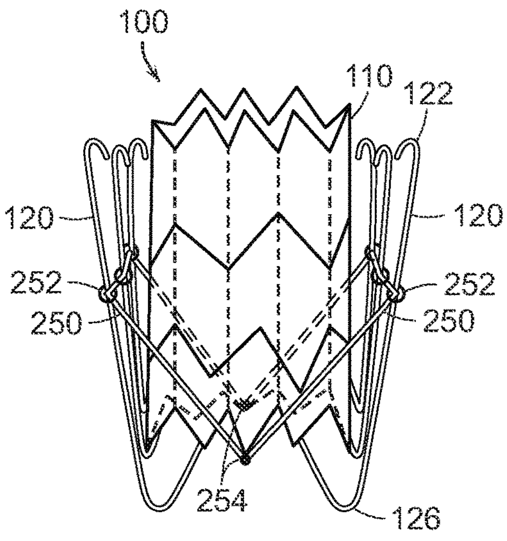
FIG. 13A
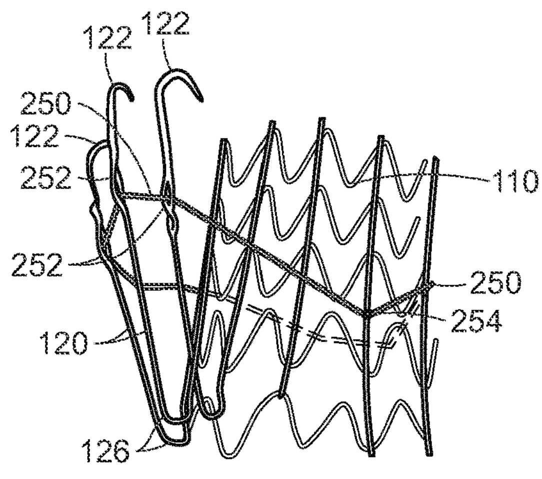
FIG. 13B
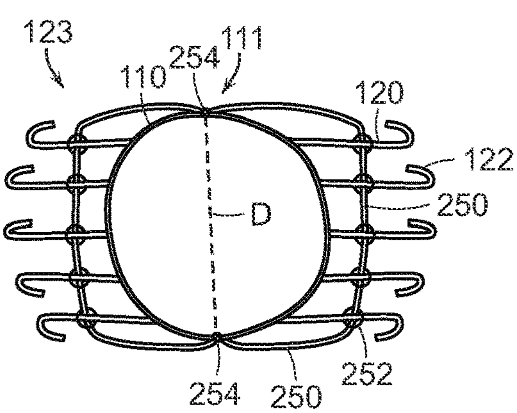
FIG. 13C
121
113
254
110
122
120
D
250
252
254
250
FIG. 13D
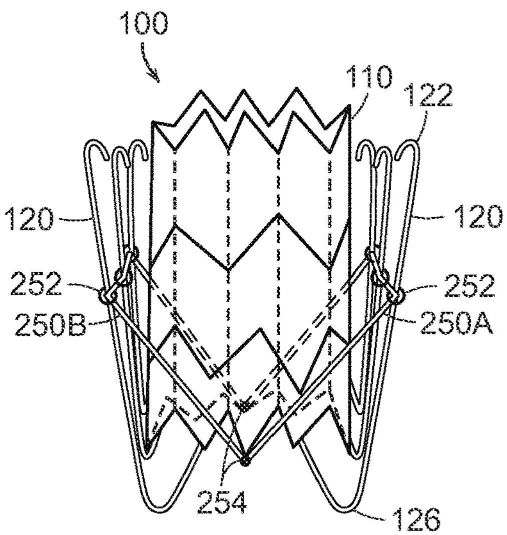
FIG. 14

PROSTHETIC HEART VALVE DEVICES AND ASSOCIATED SYSTEMS AND METHODS

CROSS-REFERENCES TO RELATED APPLICATIONS

The present application is a continuation of U.S. patent application Ser. No. 16/999,883, filed Aug. 21, 2020, which is a continuation of U.S. patent application Ser. No. 16/020,851, filed Jun. 27, 2018, now U.S. Pat. No. 10,751,173, which is a continuation of U.S. patent application Ser. No. 15/415,091, filed Jan. 25, 2017, now U.S. Pat. No. 10,034,750, which is a continuation of U.S. patent application Ser. No. 15/146,750, filed May 4, 2016, now U.S. Pat. No. 9,585,751, which is a continuation of U.S. patent application Ser. No. 14/807,788, filed Jul. 23, 2015, now U.S. Pat. No. 9,579,196, which is a continuation of U.S. patent application Ser. No. 13/949,098, filed Jul. 23, 2013, now U.S. Pat. No. 9,125,740, which is a continuation of International Application No. PCT/US2012/043636, filed Jun. 21, 2012, entitled "PROSTHETIC HEART VALVE DEVICES AND ASSOCIATED SYSTEMS AND METHODS," which claims priority to U.S. Provisional Patent Application No. 61/499,632, filed Jun. 21, 2011, entitled "HEART VALVE REPLACEMENT METHODS AND APPARATUS," the disclosures of each of these applications is incorporated herein by reference in its entireties.

TECHNICAL FIELD

The present technology relates generally to prosthetic heart valve devices. In particular, several embodiments are directed to heart valve devices for percutaneous replacement of native heart valves and associated systems and methods.

BACKGROUND

The present technology is generally directed to treatment of heart disease related to valves of the heart such as percutaneous replacement of the mitral valve. Although specific reference is made to percutaneous replacement of the mitral valve, embodiments of the present technology can provide percutaneous or other treatment of other valves such as the aortic valve.

During a normal cycle of heart contraction (systole), when the left ventricle contracts, the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure in at least some instances. The mitral valve regurgitation can be characterized by retrograde flow from the left ventricle of a heart through an incompetent mitral valve into the left atrium.

Mitral valve regurgitation can result from a number of mechanical defects of the mitral valve. The mitral valve includes leaflets and chordae tendineae coupled to the leaflets. One or more of the leaflets, the chordae tendineae, or the papillary muscles may be damaged or otherwise dysfunctional. In at least some instances, the valve annulus may be damaged, dilated, or weakened, thereby limiting the ability of the mitral valve to close adequately against the high pressures of the left ventricle.

The prior methods and apparatuses to treat valves of the heart can be less than ideal in at least some instances. Although open heart surgery can be used to repair valves of the heart, such surgery can be more invasive than would be ideal. For example, suturing opposed valve leaflets together, referred to as the "bow-tie" or "edge-to-edge" technique, can result in improved heart function. However, with open heart surgery the patient's chest is opened, typically via a sternotomy, and the patient placed on cardiopulmonary bypass. The need to open the chest and place the patient on bypass can be traumatic and may have associated morbidity.

Although recent advances in percutaneous technologies have resulted in valve therapies that can be less invasive, such percutaneous therapies can be less than ideal and may have less than ideal outcomes in at least some instances. Although clips may be delivered percutaneously to connect leaflets of the mitral valve to perform an edge-to-edge repair, placement of these clips on the mitral valve can be difficult. For example, the mitral valve leaflets can move and change shape with blood flow and contractions of the heart, such that alignment and placement of a clip on the valve can be more difficult than would be ideal in at least some instances. Further, many patients suffer from mitral valve disease which is not treatable with such clips or other percutaneous therapies so are left with no options other than open surgical repair or replacement.

Percutaneous treatment of the mitral valve can present additional challenges as compared with other valves such as the aortic valve. The methods and apparatus appropriate for the aortic valve may not be well suited for use with the mitral valve in at least some instances. The mitral valve includes clusters of chordae tendineae extending from the valve leaflets to the walls of the ventricle that may interfere with placement of the prosthesis. The shape of the mitral valve, rather than being circular and uniform like the aortic valve, can be an oval or kidney-like shape that may not be well suited for supporting conventional stents of cylindrical configuration. The mitral valve annulus can be distorted and may have an unpredictable and non-uniform geometry, as compared to the aortic valve annulus. Further, whereas the aortic valve annulus is often entirely surrounded by muscular tissue, the mitral valve annulus may be bounded by muscular tissue on the outer wall only. The anterior side of the mitral valve annulus is bounded by a thin vessel wall. The thin vessel wall separates the mitral valve annulus and the left ventricular outflow tract ("LVOT"), which must remain open to allow blood to pass into the aorta. As a result, the stent-type fixation upon which prior transcatheter prostheses rely may not be suitable for the mitral valve because the anterior side of the valve has insufficient radial strength and can distort under the radial force of such a stent, risking occlusion of the left ventricular outflow tract. Moreover, mitral valve disease often is accompanied by (or caused by) gradual enlargement of the native annulus and/or the left ventricle. Thus, treatment approaches which rely upon radial engagement with or outward compression against the native annulus are subject to failure as the size and shape of the annulus changes.

In light of the above, it would be desirable to provide improved treatments for heart valves, such as mitral valve replacement. Ideally, these treatments would decrease at least some of the deficiencies of the prior art, and provide improved percutaneous valve prostheses with greater ease of alignment and improved coupling of the prostheses to tissues of the heart.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIG. 1C-1 is a schematic illustration of a native mitral valve of a heart showing normal closure of native mitral valve leaflets.

FIG. 1C-2 is a schematic illustration of a native mitral valve of a heart showing abnormal closure of native mitral valve leaflets in a dilated heart, and which is suitable for combination with various prosthetic heart valve devices in accordance with embodiments of the present technology.

FIGS. 2A1 and 2A2 are side and top views of a prosthetic heart valve device having a valve portion, a support in a delivery configuration and a plurality of arms having an outward configuration configured to reach behind leaflets of the native mitral valve, in accordance with an embodiment of the present technology.

FIG. 2A3 is a top view of the device of FIGS. 2A1 and 2A2 with the support in an expanded configuration and showing the valve open, in accordance with an embodiment of the present technology.

FIG. 2A4 is a top view of the device of FIGS. 2A1 and 2A2 with the support in an expanded configuration and showing the valve closed, in accordance with an embodiment of the present technology.

FIG. 2A5 is a side view of an individual arm in accordance with an embodiment of the present technology.

FIG. 2A6 is a schematic illustration showing a plurality of arms extending around a native leaflet and between chordae of a native mitral valve, in accordance with an embodiment of the present technology.

FIGS. 2A7A-2A7D are side views of tip portions of individual arms, in accordance with various embodiments of the present technology.

FIG. 2A7E is a side view of a portion of a prosthetic heart valve device showing an arm having a curved tip portion oriented inwardly toward the support for retaining a native leaflet around the proximal end of the support, in accordance with an embodiment of the present technology.

FIG. 2A8 is a top view of a prosthetic heart valve device showing a support and a plurality of arms, wherein the arms are in an inward configuration and wherein pressure reducing tip portions of the arms are oriented along a surface of the support, in accordance with an embodiment of the present technology.

FIG. 2A9 is a side view of a prosthetic heart valve device showing arms in an outward configuration at varying splay angles from a support configured in accordance with an embodiment of the present technology.

FIGS. 2A10 and 2A11 are top and side views, respectively, of a support and a plurality of arms arranged in varying splay angles relative to a longitudinal axis of the support configured in accordance with an embodiment of the present technology.

FIG. 2B-1 is a schematic, cross-sectional illustration of a heart showing delivery of a prosthetic heart valve device positioned in a distal end of a delivery catheter to the native mitral valve MV region, in accordance with various embodiments of the present technology.

FIG. 2B-2 is an enlarged cross-sectional view of a prosthetic heart valve device within a catheter sheath for delivering to a native valve region of the heart configured in accordance with an embodiment of the present technology.

FIG. 2C1 is a top view of the device shown in FIG. 2C.

FIG. 2C2 is a side view of an individual arm configured to have variable length and in accordance with another embodiment of the present technology.

FIGS. 2C3 and 2C4 are side views of individual arms showing, respectively, a first outward configuration prior to expansion of the support and a second outward configuration after expansion of the support configured in accordance with an embodiment of the present technology.

FIGS. 2C5 and 2C6 are side views of individual arms showing schematically a twisting movement of the arms when transitioning from the first outward configuration (FIG. 2C5) to the second outward configuration (FIG. 2C6), in accordance with an embodiment of the present technology.

FIGS. 2F1-A and 2F1-B are side and top views, respectively, of a prosthetic heart valve device having sealing members configured to be positioned adjacent the commissures of the native valve, and in accordance with another embodiment of the present technology.

FIGS. 2F2-A and 2F2-B are isometric side and top views, respectively, of a prosthetic heart valve device having a bell-shaped skirt tapering from an open downstream end to a closed, narrower upstream end configured in accordance with a further embodiment of the present technology.

FIGS. 2F3A-2F3B and 2F4A-2F4C are side views of a prosthetic heart valve device having alternative skirt configurations in accordance with further embodiments of the present technology.

FIGS. 2F5A and 2F5B are top and cross-sectional side views, respectively, of a prosthetic heart valve device having leaflet pushers shown in an open or separated configuration and in accordance with an embodiment of the present technology.

FIGS. 2F5C and 2F5D are top and cross-sectional side views, respectively, of a prosthetic heart valve device having leaflet pushers shown in a closed or inward configuration in accordance with an embodiment of the present technology.

FIG. 2H-1 is an isometric side view of a prosthetic heart valve device having a flange extending outwardly from the support at a proximal, upstream end configured in accordance with another embodiment of the present technology.

FIG. 2H-2 is an isometric view a prosthetic heart valve device having a support with a plurality of elongated fingers extending radially outward from the proximal, upstream end of the support configured in accordance with a further embodiment of the present technology.

FIG. 2I is an isometric side view of a prosthetic heart valve device configured for positioning in a native aortic valve, and in accordance with another embodiment of the present technology.

FIG. 2J is a top view of a prosthetic heart valve device having a plurality of sealing members configured to extend toward tricuspid valve commissures of the native aortic valve, and in accordance with yet another embodiment of the present technology.

FIG. 3A is an isometric view of a prosthetic heart valve device having an expandable support shown in a delivery configuration and having a plurality of arms shown in an inward configuration, such that the device is suitable to access a valve of the body percutaneously, and in accordance with various embodiments of the present technology.

FIGS. 3B, 3C and 3D show front, side, and top views, respectively, of the device having the expandable support and plurality of arms configured as in FIG. 3A.

FIG. 3II is a force diagram illustrating the forces exerted on the arms during systole and showing the corresponding forces to the support's struts and posts in accordance with aspects of the present technology.

FIGS. 4A and 4B are side views of prosthetic heart valve devices having a plurality of arms shown a first inward configuration (FIG. 4A) and an outward configuration and having a plurality of lengths (FIG. 4B), configured in accordance with other embodiments of the present technology.

FIGS. 5A1 to 5A4 are side views of a prosthetic heart valve device having arms with ringed ends configured in accordance with an embodiment of the present technology.

FIG. 5A5 is a partial side view of a prosthetic heart valve device having arms with a first, flattened cross-sectional dimension and a second, elongated cross-sectional dimension such that the arms have a relative resistance to bending in different directions and configured in accordance with an embodiment of the present technology.

FIG. 5A6A shows a portion of the arm along line A-A of FIG. 5A5.

FIG. 5A6B shows a portion of the arm along line B-B of FIG. 5A5.

FIGS. 5A7-5A8 are side and front views, respectively, of prosthetic heart valve devices with arms including arm tips having a bent tip portion for providing a planar subannular interfacing tip configured in accordance with embodiments of the present technology.

FIGS. 5A9-5A10 are partial side views of a prosthetic heart valve device having an arm with loop and two support attachment points. The looped arm can be in an outward configuration (FIG. 5A9) suitable for positioning within a native valve structure, or in an inward configuration (FIG. 5A10) with a low cross-sectional profile suitable for retention in a delivery catheter and configured in accordance with an embodiment of the present technology.

FIG. 5A11 is a perspective view of a further embodiment of a prosthetic heart valve device having a cover thereon in accordance with aspects of the present technology.

FIGS. 5A12-5A15 are partial side views showing various embodiments of covers on arms of a prosthetic heart valve device in accordance with aspects of the present technology.

FIGS. 6A1 to 6B4 are bottom, front, side and isometric views of prosthetic heart valve devices showing arms that cross from a support attachment site on a first side of a support to a leaflet and/or annulus engaging site oriented on a second side of the support opposite the first side and configured in accordance with additional embodiments of the present technology.

FIG. 7A is a top view of a prosthetic heart valve device having an expanded support with arms and a separate prosthetic valve retained and positioned inside the expanded support configured in accordance with an embodiment of the present technology.

FIG. 7A1 is a perspective view of a separate prosthetic valve shown in an expanded configuration and configured for use with an expanded support of a prosthetic heart valve device configured in accordance with an embodiment of the present technology.

FIG. 7B is a top view of a prosthetic heart valve device having an expanded support with arms and a temporary valve structure, and showing a separate prosthetic valve retained and positioned inside the expanded support and within the temporary valve structure and configured in accordance with another embodiment of the present technology.

FIGS. 7B1 to 7B3 show various components and construction of a temporary valve comprising leaflets, in accordance with embodiments of the present technology.

FIGS. 9A-9D are enlarged cross-sectional views of a delivery catheter having an inner shaft and a middle shaft, in accordance with additional embodiments of the present technology.

FIG. 10 is an enlarged cross-sectional view of a delivery catheter including a second sheath slidably disposed within a first sheath, in which the second sheath is configured to slide between the outer surface of a support and a plurality of arms of a prosthetic heart valve device and configured in accordance with a further embodiment of the present technology.

FIGS. 12A-12C are side elevational views of various components of a delivery system for a prosthetic heart valve device configured in accordance with additional embodiments of the present technology.

FIGS. 12D-12G are side views of a distal portion of the delivery system of FIGS. 12A-12C having a prosthetic heart valve device disposed therein and showing various arrangements of the device during deployment of the device from the delivery system, in accordance with an embodiment of the present technology.

FIGS. 13A-13B are elevated side and oblique views, respectively, of a prosthetic heart valve device having a belt coupled between an expandable support and a plurality of arms configured in accordance with an embodiment of the present technology.

FIGS. 13C-13D are top views of the device of FIGS. 13A-13B showing the arms in an outward orientation (FIG. 13C) and in an inward orientation or configurations (FIG. 13D) in accordance with aspects of the present technology.

FIG. 14 is an elevated side view of a prosthetic heart valve device having a pair of belts coupled between an expandable support and a plurality of arms configured in accordance with another embodiment of the present technology.

DETAILED DESCRIPTION

Figure 1:
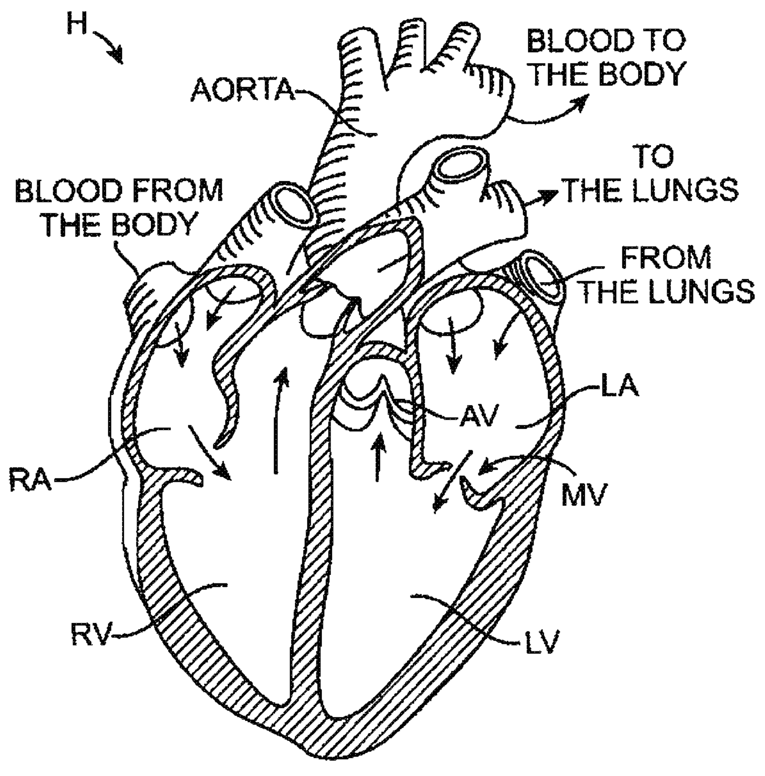
FIGS. 1 and 1A are schematic illustrations of a mammalian heart having native valve structures suitable for replacement with various prosthetic heart valve devices in accordance with embodiments of the present technology.

Specific details of several embodiments of the technology are described below with reference to FIGS. 1-16C. Although many of the embodiments are described below with respect to devices, systems, and methods for percutaneous replacement of a native heart valve using prosthetic valve devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-16C.

With regard to the terms "distal" and "proximal" within this description, unless otherwise specified, the terms can reference a relative position of the portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow. For ease of reference, throughout this disclosure identical reference numbers and/or letters are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Overview

Systems, devices and methods are provided herein for percutaneous replacement of native heart valves, such as mitral valves. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Embodiments of the present technology provide systems, methods and apparatus to treat valves of the body, such as heart valves including the mitral valve. The apparatus and methods enable a percutaneous approach using a catheter delivered intravascularly through a vein or artery into the heart. Additionally, the apparatus and methods enable other less-invasive approaches including trans-apical, trans-atrial, and direct aortic delivery of a prosthetic replacement valve to a target location in the heart. The apparatus and methods enable a prosthetic device to be anchored at a native valve location by engagement with a subannular surface of the valve annulus and/or valve leaflets. In accordance with various embodiments of the present technology, the valve annulus or leaflets are engaged within a subannular space behind (radially outside of) the native leaflets. In particular embodiments, the subannular surface is engaged by one or more elongated members, or arms, which extend from a location downstream of the native annulus. The elongated members may extend around a downstream edge of at least one native leaflet, and may further pass between two or more chordae tendineae coupled to the native leaflets. The elongated members may have an upstream end configured to engage the subannular surface. In some embodiments, the elongated members are oriented so as to be generally orthogonal to, or at an oblique angle between about 45 and 135 degrees relative to, the subannular surface, such that the loading exerted upon the elongated members is primarily a compressive, axial load. The prosthetic device may comprise a support coupled to the elongated members which contains a prosthetic valve, or which is configured to receive a separately-delivered prosthetic valve, such as a stented valve prosthesis. The elongated members can be configured to maintain the position of the prosthetic device and resist movement in at least the upstream direction when the device is subject to the force of blood pressure downstream of the valve and when the valve is closed.

In some embodiments, the arms of the apparatus may be shorter in length so as to not extend completely into engagement with the annulus tissue behind the leaflets. Additionally, in some arrangement, the arms may comprise short hooks which extend around the free edges of the native leaflets and behind the leaflets only a short distance sufficient to keep the arms from slipping off the leaflets. The arms may alternatively be configured to engage or couple to the chordae, papillary muscles or ventricular walls to enhance anchoring. Moreover, the arms may be configured to remain on the inner sides of the native leaflets and to engage the leaflets themselves, or to penetrate through the leaflets to contact the annulus or other tissue behind the leaflets. All of the various features and characteristics of the arms described herein may be applicable to longer arms, which engage sub-annular tissue, as well as shorter arms or arms which remain on the inner sides of the leaflets. Additionally, devices may include or incorporate a plurality of arms of different length or arms having different modes of engagement with the leaflets or other native tissue.

The devices, systems and methods described herein overcome many of the challenges of previous percutaneous valve replacement approaches. In particular, the apparatus and methods may eliminate the need to rely solely upon radial engagement with an outward force against the native valve annulus in order to anchor the prosthetic device, such as a replacement valve, to the native valve. The apparatus and methods may be well-suited for treating non-circular, asymmetrically shaped valves and bileaflet or bicuspid valves, such as the mitral valve. The apparatus and methods further provide for permanent and reliable anchoring of the prosthetic device even in conditions where the heart or native valve may experience gradual enlargement or distortion.

Some embodiments of the disclosure are directed to prosthetic heart valve devices for implanting at a native valve located between an atrium and a ventricle of a heart of a patient. Such devices are suitable, for example, for implantation at native valves that have an annulus and leaflets coupled to the annulus. In one embodiment, the device can have an expandable support having an outer surface and configured for placement between the leaflets. The device can also have a plurality of arms coupled to or otherwise extending from the expandable support and configured to receive the leaflets between the arms and the outer surface of the expandable support. In some embodiments, at least two arms can have different lengths to extend different distances behind the leaflets to engage a subannular surface of the annulus. In other embodiments, the plurality of arms can be asymmetrically arranged around a circumference of the expandable support and configured to receive the leaflets between the arms and the outer surface. In some examples, asymmetrically arranged arms can be arms with varying distance between adjacent arms. Alternatively or additionally, the arms may be asymmetrically arranged around a longitudinal axis passing through a center of the expandable support, e.g., with more arms disposed on one side of the axis than on an opposite side. In other examples, asymmetrically arranged arms can be arms having varying lengths or varying extension angles, wherein an extension angle is the angle between an upstream extending portion of the arm and the vertical or longitudinal axis of the support. In further examples, asymmetrically arranged arms can be arms having varying splay angles for increasing or decreasing the distance between tip portions of adjacent arms. A person skilled in the art will recognize other ways to asymmetrically arrange arms around the circumference of the expandable support.

In another embodiment, the device can further include a sealing member coupled to at least one of the expandable support and the arms. The sealing member, in some embodiments can be membranes configured to extend from the expandable support into the commissural region of the valve as to inhibit blood flow through a commissural region of a valve. In some embodiments, the device can include two sealing members, which could be membrane structures or rigid structures) oriented on the device to inhibit blood flow through commissural regions of a bicuspid valve (e.g., mitral valve or a bicuspid aortic valve). In another embodiment, the device can include three or more sealing members oriented on the device as to inhibit blood flow through commissural regions of a tricuspid (e.g., aortic valve) or other valve. In a further embodiment, the device can include a single skirt shaped membrane oriented on the device as to inhibit blood flow through gaps formed between the device and the native valve.

Other embodiments of the disclosure are directed to prosthetic heart valve devices for implantation at a native valve region of a heart. In one embodiment, the device can include an expandable support having an upstream portion and a downstream portion. The expandable support can also be configured to be located at the native valve region such that the upstream portion is in fluid communication with a first heart chamber and the downstream portion is in fluid communication with a second heart chamber or portion. In one example, the native valve region can be a mitral valve region and the first heart chamber can be a left atrium and the second heart chamber can be a left ventricle. In another example, the native valve region can be an aortic valve region and the first heart chamber can be a left ventricle and the second heart chamber or portion can be an aorta.

The prosthetic heart valve device can also include a plurality of arms coupled to the expandable support at the downstream portion. The arms, for example, can be formed integrally with the expandable support, or the arms can be separate components that are attached to the expandable support (e.g., spot welded). In one embodiment, each individual arm can be configured to extend from the downstream portion to engage a subannular surface of the native valve region within the second chamber (or portion). In some embodiments, at least some of the individual arms have independently adjustable lengths. In other embodiments, the individual arms can have a base portion, an extension portion and an elbow portion connecting the base portion to the extension portion. The extension portion can be configured, in some embodiments, to engage a subannular surface of the native valve region within the second chamber or portion. In further embodiments, individual arms extend from the support at different splay angles.

Further embodiments of the present technology provide a device to treat a heart valve of a patient, wherein the valve includes an annulus and leaflets coupled to the annulus. The device can include an expandable support comprising an outer surface, an upstream portion and a downstream portion. The support can be configured for placement between the leaflets. The device can also include a plurality of arms coupled to the expandable support. In some arrangements, the plurality of arms can include a first plurality of arms and a second plurality of arms. The first plurality of arms can be arranged on a first portion of the support to receive a first leaflet and the second plurality of arms can be arranged on a second portion of the support to receive a second leaflet. In some examples, the first plurality of arms can include a larger number of arms than the second plurality of arms.

Another embodiment of the present technology provides a device for repair or replacement of a bicuspid heart valve having an annulus, leaflets coupled to the annulus and chordae tendineae coupled to the leaflets. The device can include a hollow support positionable between the leaflets and having an interior to which a valve may be coupled. The device can also include an anchoring portion coupled to the support. The anchoring portion can have an arcuate region configured to extend around a downstream edge of at least one leaflet, an extension region configured to extend from the downstream edge between the chordae tendineae to the annulus, and an engagement region configured to engage a subannular surface of the annulus so as to inhibit movement of the device in an upstream direction. The device can also optionally include a sealing member coupled to at least one of the support and the anchoring portion and extending outwardly from the expandable support into a commissural region of the bicuspid valve so as to occlude the commissural region to inhibit blood flow through the commissural region. In some embodiments, the membrane can be a sealing member configured to engage the commissural region from a ventricle or downstream side of the bicuspid heart valve.

Further embodiments of the disclosure are directed to devices for repair or replacement of a heart valve having an annulus and leaflets coupled to the annulus. In one embodiment, the device can include a cylindrical support configured for placement between the leaflets. The support can include proximal and distal portions, or in other embodiments, upstream and downstream portions. The cylindrical support can also include an interior in which a valve may be coupled. The device can also include a first group of arms (e.g., anchoring arms) coupled to a posterior side of the cylindrical support and a second group of arms (e.g., anchoring arms) coupled to an anterior side of the cylindrical support opposite the posterior side. In one embodiment, each arm can be configured to extend around a downstream edge of a leaflet and extend between the chordae tendineae. Each arm may also engage a subannular surface of the annulus so as to inhibit movement of the support in an upstream direction. In some arrangements, the first group of arms can be configured to engage a first subannular surface along a first line and the second group of arms can be configured to engage a second subannular surface along a second line. In some embodiments, the first and second lines can be non-parallel to the annulus. For example, in one embodiment, the first and second lines are substantially straight, and in another embodiment, the first and second lines can have a curvature substantially larger than a radius of the annulus.

In some embodiments, anchoring arms can be coupled to downstream portions of the cylindrical support and extend outwardly in an upstream direction. The anchoring arms can have distal tips configured to atraumatically engage the annulus of the heart valve. In some arrangements, the plurality of anchoring arms can include a first and second plurality of anchoring arms. The first plurality of anchoring arms can have a characteristic different than the second plurality of anchoring arms. Examples of such arm characteristics can include size, shape, stiffness, splay angle, spacing from the support, and the number of arms disposed within a given area of the support. One of ordinary skill in the art will recognize other arm characteristics that can vary between separate groups of arms coupled to the support and/or associated with the devices disclosed herein.

In a further embodiment, the cylindrical support can have upstream and downstream ends, an interior in which a valve may be coupled, and a perimeter. A plurality of arms can be coupled to the cylindrical support and extend outwardly and in an upstream direction. The arms can include distal tips configured to atraumatically engage the annulus of the heart valve. Further, the arms can be unevenly or otherwise irregularly distributed about the perimeter such that at least a first adjacent pair of arms is spaced closer together than at least a second adjacent pair of arms.

Other embodiments of the disclosure are directed to prosthetic heart valve devices having cylindrical supports having upstream and downstream ends, an interior in which a valve may be coupled and a central longitudinal axis. The devices can also include a plurality of arms extending outwardly from the cylindrical support in an upstream direction. The arms can have distal tips configured to atraumatically engage a subannular surface of a native heart valve. In some embodiments, at least one of the arms can extend outwardly from the longitudinal axis by a greater distance than at least a second of the arms.

A prosthetic heart valve device may also, in some embodiments, include an expandable support having an upstream portion and a downstream portion. The support, for example, can be configured to be located at a native valve region such that the upstream portion is in fluid communication with a first heart chamber and the downstream portion is in fluid communication with a second heart chamber. The device can also include at least one arm coupled to the support and extending in an upstream direction with a distal tip configured to engage an annulus of the native valve region within the second heart chamber. The arm can have a column strength selected to maintain the position of the support relative to the heart valve under the force of blood during systole, e.g., a force of at least about 0.5 lbf exerted against the support in the upstream direction. If multiple arms are utilized, the column strength of each arm can be selected such that in combination the arms maintain the position of the support relative to the heart valve under such a systolic load.

Some devices can include a cylindrical support having a longitudinal axis and an interior along the longitudinal axis through which blood may flow. The device may also include a valve coupled within the interior of the support that is configured to block blood flow through the support in an upstream direction and allow blood flow through the support in a downstream direction. The device can further include a plurality of arms coupled to the support and extending in the upstream direction along an exterior wall or surface of the support. The device may be movable into a plurality of configurations that can include a) a first configuration in which the support is radially contracted and each arm is in an inward position against or adjacent to the exterior wall of the support, b) a second configuration in which the support is radially contracted and each arm is in an outward position spatially separated from the exterior wall by a distance sufficient to receive a leaflet of the heart valve therebetween, and c) a third configuration in which the support is radially expanded and each arm is positioned closer to the exterior wall of the support than in the second configuration.

In many embodiments, an apparatus comprises an expandable support coupled to a plurality of arms. The expandable support may comprise an upstream portion for placement near an upstream portion of the valve and a downstream portion for placement near a downstream portion of the valve. The plurality of arms may extend from the downstream portion and may comprise an inward configuration for placement in a lumen of a catheter and an outward configuration to reach behind the leaflets and engage the annulus. The expandable support and the plurality of arms can be introduced into the patient percutaneously with the plurality of arms comprising the inward configuration and the expandable support comprising a first non-expanded configuration, such that the support and the plurality of arms can be advanced along the lumen of a catheter toward the intended valve. A sheath covering the plurality of arms and the expandable support can be drawn proximally so as to expose the plurality of arms, and the plurality of arms can move outward from the expandable support so as to comprise the outward configuration. In the outward configuration, the plurality of arms can extend, in some embodiments, between chordae tendineae of the mitral valve and receive the leaflets between the plurality of arms and the support. The support can be moved upstream with the leaflets received between the plurality of arms and the support so as to guide the plurality of arms toward the annulus. When the support has moved upstream a sufficient distance, the plurality of arms can engage the annulus with the leaflets extending substantially between the plurality of arms and the support such that the plurality of arms can engage the annulus with direct contact and with decreased interference of the leaflets. The expandable support can be expanded to an expanded configuration when the plurality of arms engages the annulus in the outward configuration. The arms may have sufficient flexibility to deflect inwardly or outwardly relative to the support sufficiently to accommodate any expansion or distortion of the native annulus which may occur in a heart afflicted with mitral valve disease, congestive heart failure, or other conditions.

A valve can be provided which is configured to be coupled to the support when the support is in the expanded configuration. The valve may be delivered separately from the support and coupled to the support after the support has been implanted at the native valve site. Alternatively the valve may be pre-mounted to the support and delivered with it to the target site. The valve may also be a temporary valve which regulates blood flow through the support for a temporary period, e.g. 15 minutes to 3 days, until a permanent prosthetic valve is delivered and coupled to the support. The valve can be supported with the plurality of arms engaging the ventricular side of the annulus behind the leaflets with the arms in the outward configuration, such that the valve is supported by direct coupling to the native annulus. This engagement of the annulus by the plurality of arms can provide safe and reliable coupling to the native valve. The integrity of neighboring tissues and structures can be substantially maintained and blood flow through the aortic outflow tract can be substantially unimpeded. The arms may comprise sufficient strength to support the valve and maintain its position during systole, and the strength may comprise a column strength which keeps the arms from buckling or fracturing under the force of blood against the valve coupled to the support.

The plurality of arms may comprise one or more structures to couple to the annulus of the valve. Each of the plurality of arms may comprise a tip portion to inhibit penetration of the annulus. The tip portion may comprise a cross-sectional size to inhibit excessive penetration of the annulus. The plurality of arms may comprise a portion to provide deflection of the tip portion.

Each of the plurality of arms may comprise a mechanism to vary the length of the arm, such as a telescopic component. The mechanism may comprise a locking mechanism which locks when the plurality of arms engage the annulus. Alternatively or in combination, the plurality of arms can be shaped to engage the annulus of the mitral valve. A first plurality of arms can be configured to engage a first portion of the annulus on a first side of the support and a second plurality of arms can be configured to engage a second portion of the annulus on a second side of the support. Each of the first plurality of arms and the second plurality of arms may be splayed outwardly from a surface of the support and configured to pass between chordae coupled to the leaflets with minimal interference therewith.

In many embodiments, the support can be configured to receive an expandable valve when the support is in the expanded configuration. The expandable valve may comprise an expandable stented valve, and the support may comprise retaining structures to couple to the expandable stented valve with one or more of friction, compression, or interlocking elements. In some embodiments, the expandable support is configured to receive an expandable aortic stented valve when the support is placed in the mitral valve. The support may be disposed in the expanded configuration when coupled to the expandable aortic stented valve and configured such that the support and the plurality of arms substantially maintain the shape and size of the native annulus and do not extend excessively into the aortic outflow tract so that blood flow through the aortic outflow tract is substantially unimpeded.

Certain embodiments of the present technology provide an apparatus to treat a mitral valve located between an atrium and a ventricle of a heart of a patient. The mitral valve has an annulus, leaflets coupled to the annulus, and chordae tendineae coupled to the leaflets. The apparatus comprises an expandable support comprising an outer surface. The expandable support is configured for placement between the leaflets and comprises an upstream portion and a downstream portion. A plurality of arms is coupled to the expandable support. The plurality of arms is configured to receive the leaflets between the arms and the outer surface and extend behind the leaflets so as to engage the annulus.

In many embodiments, the plurality of arms is configured to engage the annulus so as to inhibit movement of the support toward the atrium. The plurality of arms collectively may have column strength sufficient to support a systolic load of at least about 2 to 5 lbf exerted in the axial direction on the support. In some embodiments, each arm may be configured to support an axial compressive load of at least about 0.2 lbf, and in other embodiments, at least about 0.5 lbf.

In many embodiments, a valve is coupled to the support and is configured to inhibit retrograde blood flow when the left ventricle of the heart contracts, and the plurality of arms extends from the support to the annulus so as to couple the valve to the annulus.

In many embodiments, the plurality of arms is configured to contact the leaflets so as to further resist movement of the support. Each of the plurality of arms can be separated from the outer surface by a gap distance sized to receive the leaflets such that the leaflets are received between the plurality of arms and the support. The gap distance associated with each of the plurality of arms can be sized to guide the plurality of arms toward the annulus. Each of the plurality of arms can be independently deflectable to vary the gap distance if engaged by tissue during positioning. The arms may further be configured to be movable from a first position having a first gap distance to a second position having a second gap distance, the first gap distance being larger than the second gap distance. The arms may be moved automatically from the first position to the second position when the support is expanded to the expanded configuration, or the arms may be actively movable on demand either before or after the support is expanded. The arms may further be movable to a third position having a gap distance even smaller than in the first or second positions, in which the arms have a minimal profile so as to facilitate endovascular delivery to the target site. The arms may have an unbiased configuration which corresponds to either the first, second, or third positions.

In another aspect, embodiments of the present technology provide a method of treating a mitral valve of a patient, in which the mitral valve has an annulus and leaflets. The method comprises placing an apparatus comprising an expandable support coupled to a plurality of arms along the mitral valve such that the plurality of arms engages the annulus behind the leaflets.

In a further aspect, embodiments of the present technology provide a system to treat a mitral valve of a patient, in which the mitral valve has an annulus. The system comprises an apparatus to treat the mitral valve as described herein and a catheter having the apparatus within a lumen of the catheter.

In yet another aspect, embodiments of the present technology provide a method of treating a valve of heart of a patient. The valve has an annulus and leaflets. The method can include implanting a device as described herein within or adjacent to the annulus. The device, in some embodiments, can include an expandable support coupled to a plurality of arms. The support can be disposed between the leaflets and the plurality of arms can be configured to engage the annulus behind the leaflets. Accordingly, the method can also include engaging a surface of the annulus behind the leaflets by a plurality of arms coupled to the expandable support so as to inhibit movement of the support, and, in some embodiments, include coupling a valve to the support to allow blood flow in a first direction through the support and inhibit blood flow in a second direction through the support.

In another aspect, embodiments of the present technology provide an apparatus to treat a valve of a patient, in which the valve comprises an annulus and leaflets coupled to the annulus. An expandable support comprises an outer surface, and the expandable support is configured for placement between the leaflets. The expandable support comprises an upstream portion and a downstream portion when placed between the leaflets. A plurality of arms is coupled to the expandable support and extends from the downstream portion. The plurality of arms comprises a first plurality of arms and a second plurality of arms. The first plurality of arms is arranged on a first portion of the support to receive a first leaflet, and the second plurality of arms is arranged on a second portion of the support to receive a second leaflet. At least some of the first and second plurality of arms engage the annulus behind the first and second leaflets so as to inhibit movement of the support. A temporary or permanent valve may be coupled to the support to allow blood flow in a first direction and inhibit blood flow in a second direction.

In a further aspect of the technology, a method of securing a treatment device at a location proximate a native valve of a heart of a patient. The method can include passing a first arm of the treatment device around a free edge of the first leaflet into a first subannular space behind the first leaflet; passing a second arm of the treatment device around a free edge of the second leaflet into a second subannular space behind the second leaflet; and engaging a surface of the annulus behind the leaflets with the first and second arms to inhibit movement of the treatment device in an upstream direction relative to the native valve.

In another aspect, an apparatus to treat a valve of a patient includes an expandable support comprising an outer surface, the expandable support configured for placement between the leaflets and comprising an upstream portion and a downstream portion; and a plurality of arms coupled to the expandable support, the plurality of arms comprising a first plurality of arms and a second plurality of arms, the first plurality of arms arranged on a first portion of the support to receive a first leaflet, the second plurality of arms arranged on a second portion of the support to receive a second leaflet.

In a further embodiment, an apparatus for repair or replacement of a heart valve having an annulus, leaflets coupled to the annulus, and chordae tendineae coupled to the leaflets, comprises a support portion positionable between the leaflets and having an interior to which a valve may be coupled; an anchoring portion coupled to the support portion, the anchoring portion having a turning region configured to extend around a downstream edge of at least one leaflet, an extension region configured to extend from the downstream edge between the chordae tendineae to the annulus, and an engagement region configured to engage the annulus so as to inhibit movement of the apparatus in an upstream direction.

In still another aspect, the present technology provides an apparatus for repair or replacement of a heart valve having an annulus, leaflets coupled to the annulus, and chordae tendineae coupled to the leaflets, the apparatus comprising a cylindrical support configured for placement between the leaflets, the support having upstream and downstream ends and an interior in which a valve may be coupled; a first group of arms coupled to the support along a posterior side thereof; and a second group of arms coupled to the support along an anterior side thereof opposite the posterior side; wherein each arm is configured to extend around a downstream edge of a leaflet, between the chordae tendineae and into engagement with the annulus so as to inhibit movement of the support in an upstream direction.

In another embodiment, an apparatus for repair or replacement of a heart valve having an annulus can include a cylindrical support configured for placement between the leaflets, the support having upstream and downstream ends and an interior in which a valve may be coupled; and a plurality of arms coupled to the cylindrical support and extending in an upstream direction with distal tips configured to engage annulus tissue of the heart valve; wherein a first plurality of the arms have a characteristic different than at least a second plurality of the arms, the characteristic being selected from size, shape, stiffness, angle, spacing from the support, or the number of arms within a given area of the support.

In another aspect of the present technology, an apparatus for repair or replacement of a heart valve having an annulus is provided. The apparatus can comprise a cylindrical support having upstream and downstream ends, an interior in which a valve may be coupled, and a perimeter; and a plurality of arms coupled to the cylindrical support and extending in an upstream direction with distal tips configured to atraumatically engage annulus tissue of the heart valve; wherein the arms are unevenly distributed about the perimeter such that at least a first adjacent pair of arms is spaced closer together than at least a second adjacent pair of arms.

In a further embodiment, an apparatus for repair or replacement of a heart valve having an annulus can include a cylindrical support having upstream and downstream ends, an interior in which a valve may be coupled, and a central longitudinal axis; and a plurality of arms coupled to the cylindrical support and extending in an upstream direction with distal tips configured to engage annulus tissue of the heart valve; wherein at least one of the arms extends outwardly a greater distance from the longitudinal axis than at least a second of the arms.

In still another aspect, the present technology provides an apparatus for repair or replacement of a heart valve having an annulus which comprises a cylindrical support having upstream and downstream ends and an interior in which a valve may be coupled; and at least one arm coupled to the cylindrical support and extending in an upstream direction with a distal tip configured to engage the annulus of the heart valve behind a leaflet thereof, the at least one arm having a column strength selected to maintain the position of the support relative to the heart valve under a force of at least about 0.5 lbf exerted against the support in the upstream direction.

In a further aspect of the present technology, an apparatus for replacement of a heart valve comprises a cylindrical support having an interior through which blood may flow; a valve coupled within the interior of the support and configured to block blood flow through the support in an upstream direction and allow blood flow through the support in a downstream direction; and a plurality of arms coupled to the support and extending in the upstream direction along an exterior wall of the support; wherein the apparatus is movable into a plurality of configurations comprising a first configuration in which the support is radially contracted and each arm is in an inward position against or adjacent to the exterior wall of the support; a second configuration in which the support is radially contracted and each arm is in an outward position separated from the exterior wall by a distance sufficient to receive a leaflet of the heart valve therebetween; and a third configuration in which the support is radially expanded and each arm is positioned closer to the exterior wall of the support than in the second configuration.

Additional aspects of the present technology are described further herein. It is contemplated that the embodiments as described herein may be combined in many ways, and any one or more of the elements recited in the claims can be combined together in accordance with embodiments of the present technology and teachings as described herein.

Embodiments of the present technology as described herein can be combined in many ways to treat one or more of many valves of the body including valves of the heart such as the mitral valve. The embodiments of the present technology can be therapeutically combined with many known surgeries and procedures, for example, such embodiments can be combined with known methods of accessing the valves of the heart such as the mitral valve with antegrade or retrograde approaches, and combinations thereof.

Cardiac Physiology

Figure 1A:
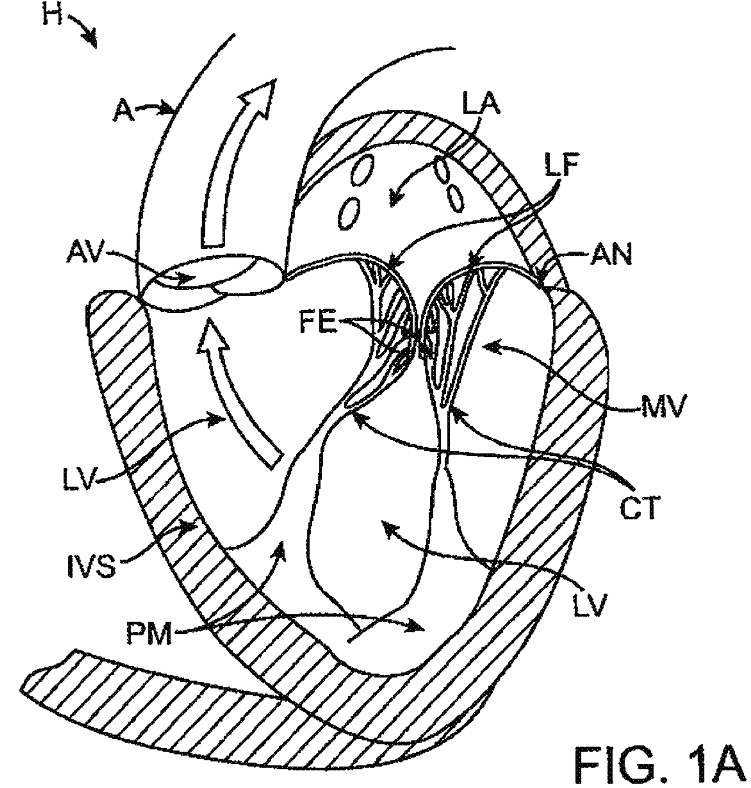

FIGS. 1 and 1A shows a heart H. The heart comprises a right atrium RA and a right ventricle RV that receive blood from the body and pump the blood from the body to the lungs. The left atrium receives oxygenated blood from the lungs via the pulmonary veins PV and pumps this oxygenated blood through the mitral MV into the left ventricle LV. The left ventricle LV pumps the blood through the aortic valve AV into the aorta from which it flows throughout the body.

The left ventricle LV of a normal heart H in systole is illustrated in FIG. 1A. In systole, the left ventricle LV contracts and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly, or "coapt" to close, as illustrated in FIG. 1A. The opposite ends of the leaflets LF are attached to the surrounding heart structure via an annular region of tissue referred to as the annulus AN. The free edges FE of the leaflets LF are secured to the lower portions of the left ventricle LV through chordae tendineae CT (referred to hereinafter "chordae") which include a plurality of branching tendons secured over the lower surfaces of each of the valve leaflets LF. The chordae CT in turn, are attached to the papillary muscles PM, which extend upwardly from the lower wall of the left ventricle and interventricular septum IVS.

Figure 1B:
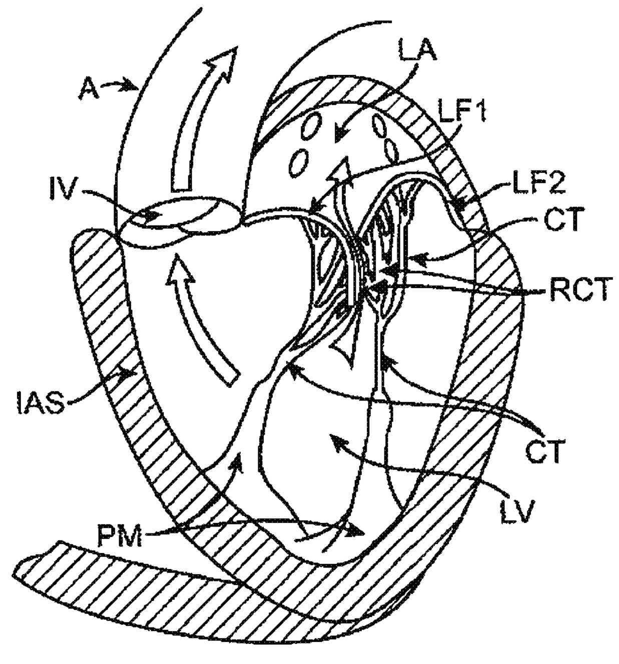
FIG. 1B is a schematic illustration of the left ventricle of a heart having prolapsed leaflets in the mitral valve, and which is suitable for combination with various prosthetic heart valve devices in accordance with embodiments of the present technology.
Figure 1C:
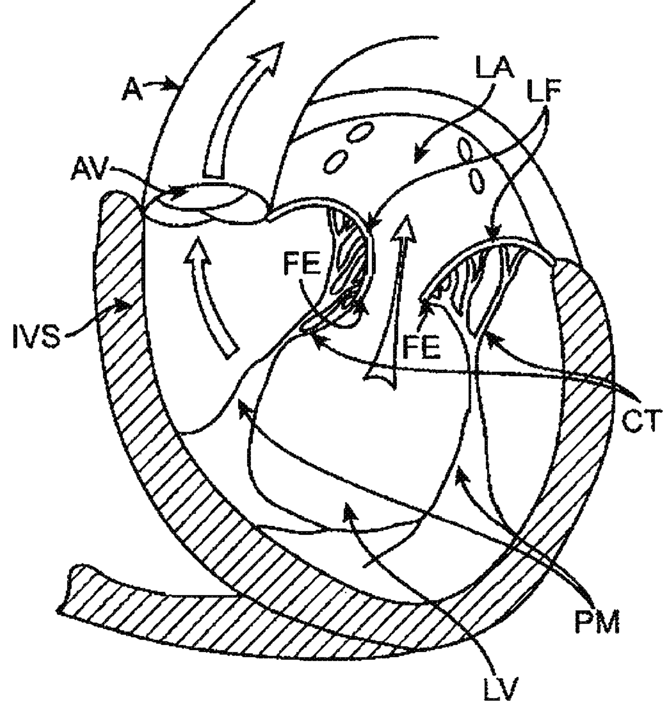
FIG. 1C is a schematic illustration of a heart in a patient suffering from cardiomyopathy, and which is suitable for combination with various prosthetic heart valve devices in accordance with embodiments of the present technology.
Figures 1, 1C:
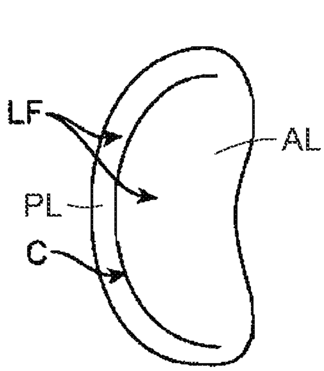
Figures 1, 1C, 2:
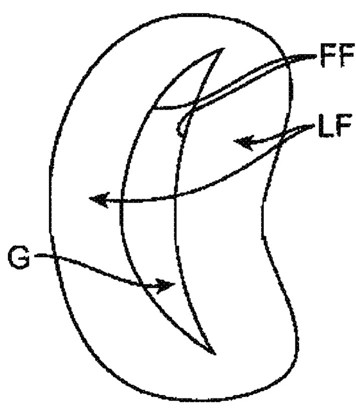
Figure 1D:
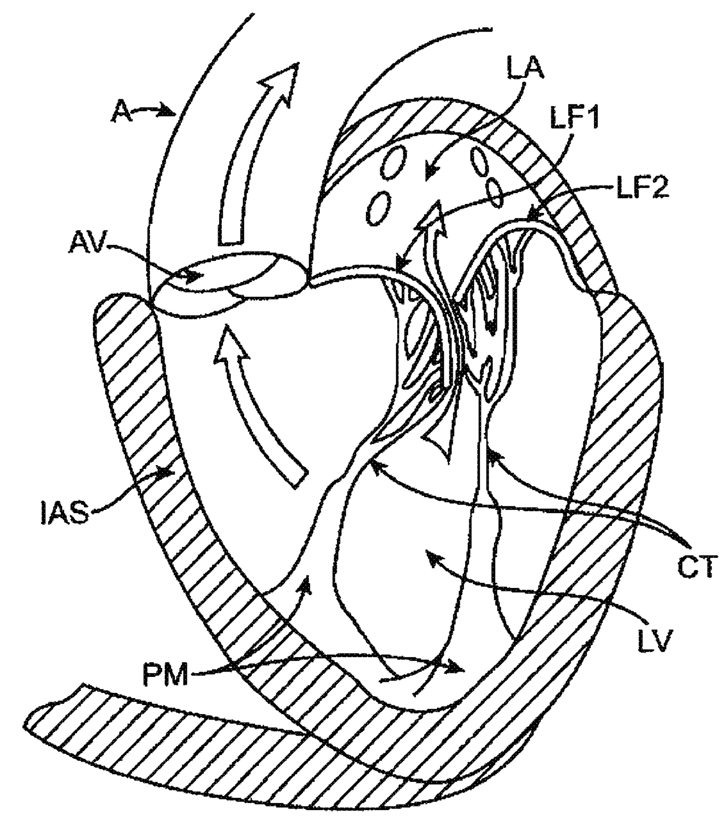
FIG. 1D illustrates mitral valve regurgitation in the left ventricle of a heart having impaired papillary muscles, and which is suitable for combination with various prosthetic heart valve devices in accordance with embodiments of the present technology.

Referring now to FIGS. 1B to 1D, a number of structural defects in the heart can cause mitral valve regurgitation. Ruptured chordae RCT, as shown in FIG. 1B, can cause a valve leaflet LF2 to prolapse since inadequate tension is transmitted to the leaflet via the chordae. While the other leaflet LF 1 maintains a normal profile, the two valve leaflets do not properly meet and leakage from the left ventricle LV into the left atrium LA will occur, as shown by the arrow.

Regurgitation also occurs in the patients suffering from cardiomyopathy where the heart is dilated and the increased size prevents the valve leaflets LF from meeting properly, as shown in FIG. 1C. The enlargement of the heart causes the mitral annulus to become enlarged, making it impossible for the free edges FE to meet during systole. The free edges of the anterior and posterior leaflets normally meet along a line of coaptation C as shown in FIG. 1C1, but a significant gap G can be left in patients suffering from cardiomyopathy, as shown in FIG. 1C2.

FIGS. 1C1, 1C2, and 1E further illustrate the shape and relative sizes of the leaflets L of the mitral valve. It may be seen that the overall valve has a generally kidney-like shape, with a long axis MVA1 and a short axis MVA2. In healthy humans the long axis MVA1 is typically within a range from about 33.3 mm to about 42.5 mm in length (37.9+/−4.6 mm), and the short axis MVA2 is within a range from about 26.9 to about 38.1 mm in length (32.5+/−5.6 mm). However, with patients having decreased cardiac function these values can be larger, for example MVA1 can be within a range from about 45 mm to 55 mm and MVA2 can be within a range from about 35 mm to about 40 mm. The line of coaptation C is curved or C-shaped, thereby defining a relatively large anterior leaflet AL and substantially smaller posterior leaflet PL (FIG. 1C1). Both leaflets appear generally crescent-shaped from the superior or atrial side, with the anterior leaflet AL being substantially wider in the middle of the valve than the posterior leaflet. At the opposing ends of the line of coaptation C the leaflets join together at corners called the anterolateral commissure AC and posteromedial commissure PC, respectively.

Mitral valve regurgitation can also occur in patients who have suffered ischemic heart disease where the functioning of the papillary muscles PM is impaired, as illustrated in FIG. 1D. As the left ventricle LV contracts during systole, the papillary muscles PM do not contract sufficiently to effect proper closure. One or both of the leaflets LF1 and LF2 then prolapse, as illustrated. Leakage again occurs from the left ventricle LV to the left atrium LA, as shown by the arrow.

Figure 1E:
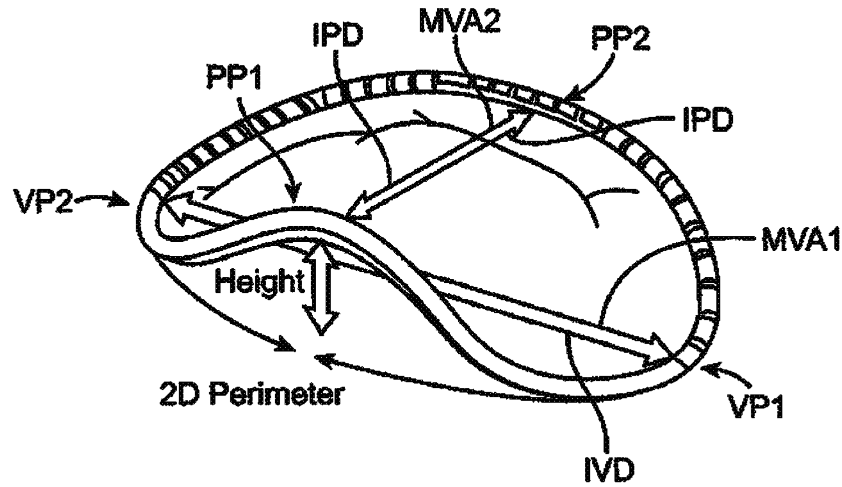
FIG. 1E is a schematic illustration of a mitral valve of a heart showing dimensions of the annulus, and which is suitable for combination with various prosthetic heart valve devices in accordance with embodiments of the present technology.

FIG. 1E shows the shape and dimensions of the annulus of the mitral valve. The annulus is an annular area around the circumference of the valve comprised of fibrous tissue which is thicker and tougher than that of the leaflets LF and distinct from the muscular tissue of the ventricular and atrial walls. The annulus may comprise a saddle-like shape with a first peak portion PP1 and a second peak portion PP2 located along an interpeak axis IPD, and a first valley portion VP1 and a second valley portion VP2 located along an intervalley axis IVD. The first and second peak portions PP1 and PP2 are higher in elevation relative to a plane containing the nadirs of the two valley portions VP1, VP2, typically being about 8-19 mm higher in humans, thus giving the valve an overall saddle-like shape. The distance between the first and second peak portions PP1, PP2, referred to as interpeak span IPD, is substantially shorter than the intervalley span IVD, the distance between first and second valley portions VP1, VP2.

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, work in relation to the present disclosure suggests that some patients may have a long dimension across the annulus and a short dimension across the annulus without well defined peak and valley portions, and the methods and apparatus as described herein can be configured accordingly.

Access to the Mitral Valve

Access to the mitral valve or other atrioventricular valve can be accomplished through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well-known and described in the patent and medical literature. Depending on the point of vascular access, the approach to the mitral valve may be antegrade and may rely on entry into the left atrium by crossing the interatrial septum. Alternatively, approach to the mitral valve can be retrograde where the left ventricle is entered through the aortic valve. Once percutaneous access is achieved, the interventional tools and supporting catheter (s) may be advanced to the heart intravascularly and positioned adjacent the target cardiac valve in a variety of manners, as described herein.

Using a trans-septal approach, access is obtained via the inferior vena cava IVC or superior vena cava SVC, through the right atrium RA, across the interatrial septum IAS and into the left atrium LA above the mitral valve MV.

Figure 1F:
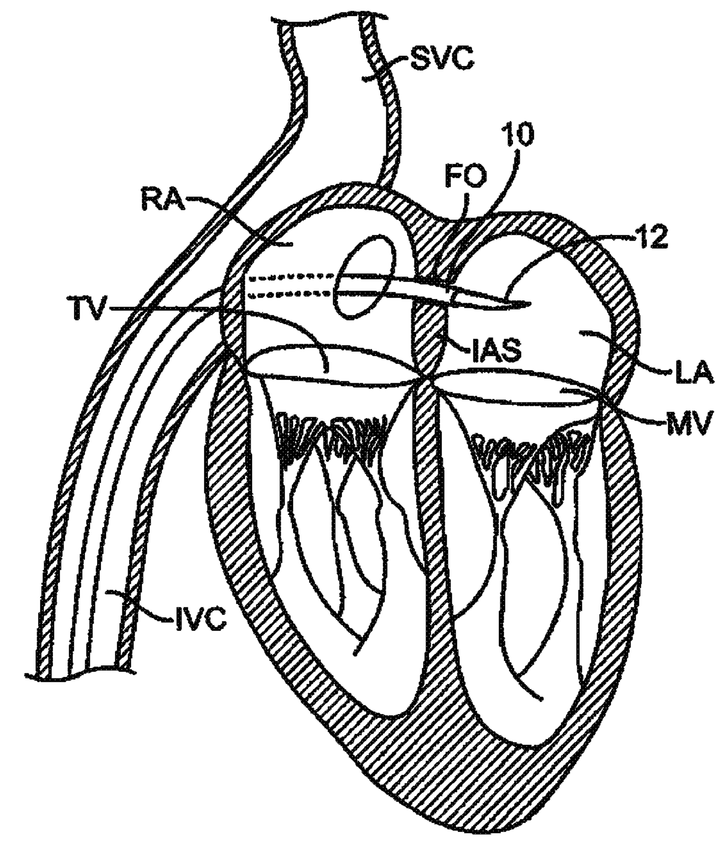
FIG. 1F is a schematic, cross-sectional illustration of the heart showing an antegrade approach to the native mitral valve from the venous vasculature, in accordance with various embodiments of the present technology.

As shown in FIG. 1F, a catheter 10 having a needle 12 may be advanced from the inferior vena cava IVC into the right atrium RA. Once the catheter 10 reaches the anterior side of the interatrial septum IAS, the needle 12 may be advanced so that it penetrates through the septum, for example at the fossa ovalis FO or the foramen ovale into the left atrium LA. At this point, a guidewire may be exchanged for the needle 12 and the catheter 10 withdrawn.

Figure 1G:
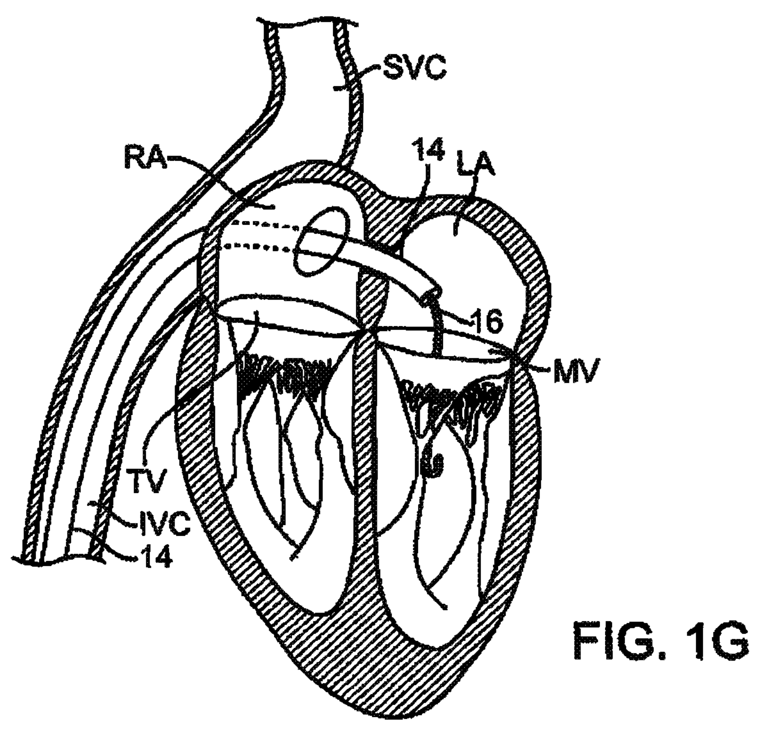
FIG. 1G is a schematic, cross-sectional illustration of the heart showing access through the interatrial septum (IAS) maintained by the placement of a guide catheter over a guidewire, in accordance with various embodiments of the present technology.

As shown in FIG. 1G, access through the interatrial septum IAS may usually be maintained by the placement of a guide catheter 14, typically over a guidewire 16 which has been placed as described above. The guide catheter 14 affords subsequent access to permit introduction of the apparatus to replace the mitral valve, as described in more detail herein below.

The antegrade or trans-septal approach to the mitral valve, as described above, can be advantageous in many respects. For example, the use of the antegrade approach will usually allow for more precise and effective centering and stabilization of the guide catheter and/or prosthetic valve apparatus. Precise positioning facilitates accuracy in the placement of the prosthetic valve apparatus. The antegrade approach may also reduce the risk of damaging the subvalvular apparatus during catheter and interventional tool introduction and manipulation. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 1H:
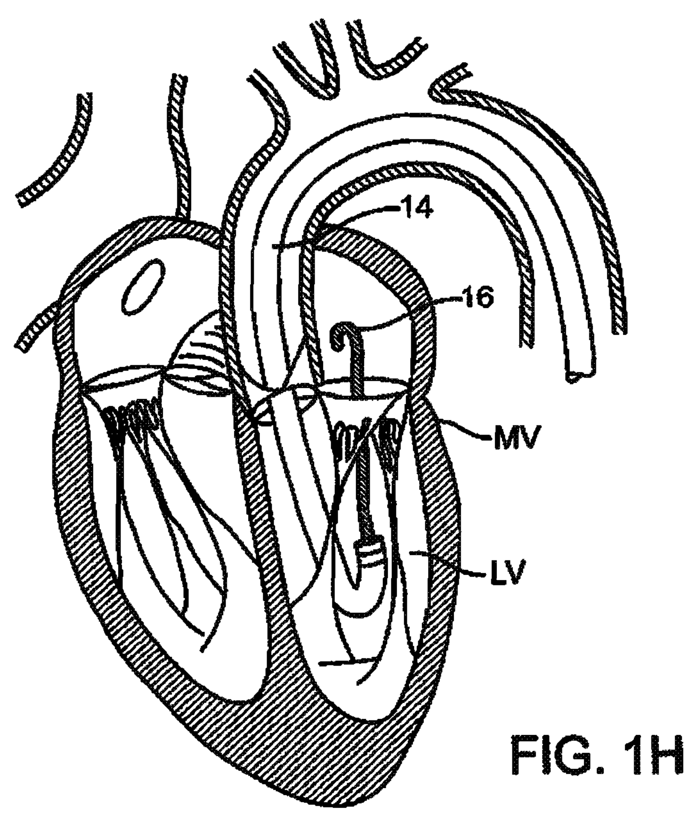
FIGS. 1H and 1I are schematic, cross-sectional illustrations of the heart showing retrograde approaches to the native mitral valve through the aortic valve and arterial vasculature, in accordance with various embodiments of the present technology.
Figures 1I, 1J:
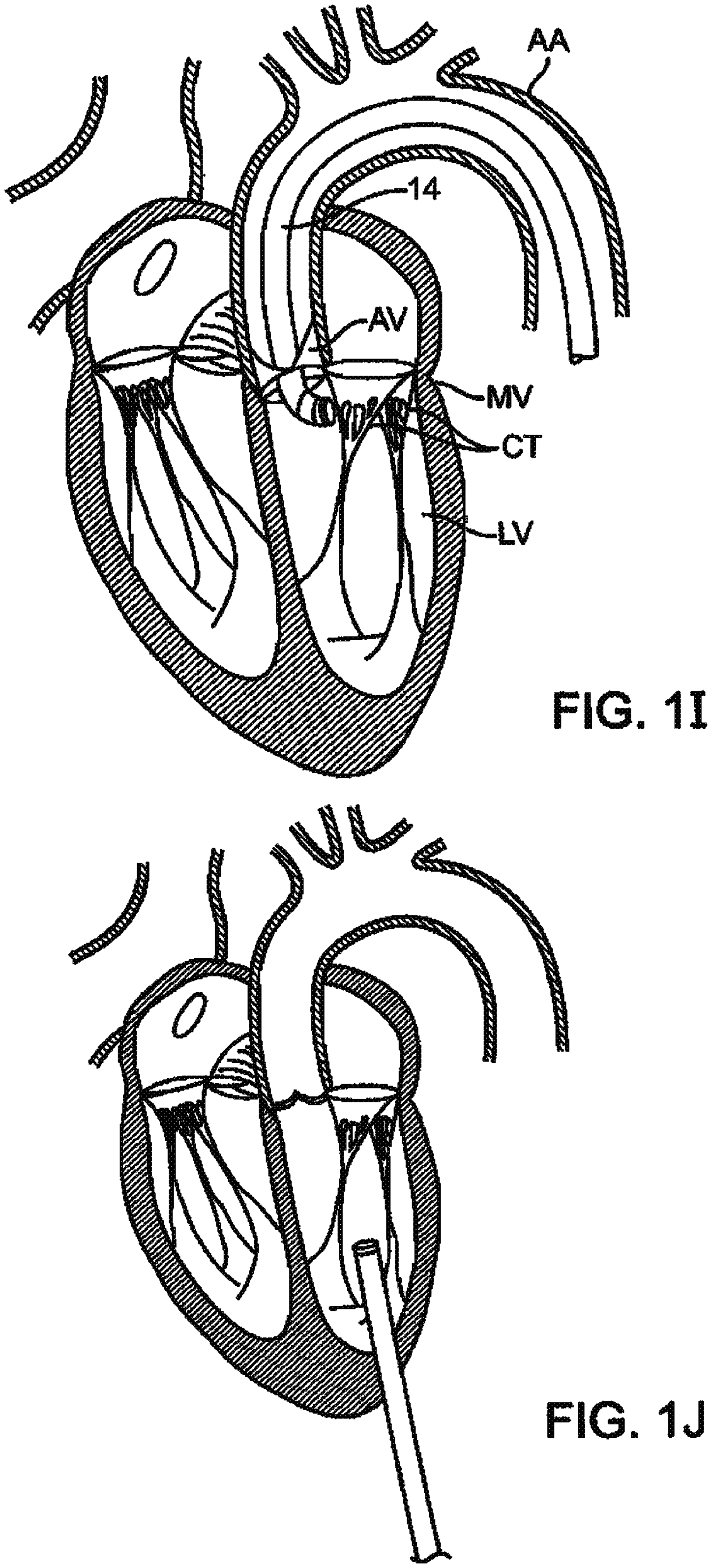
FIG. 1J is a schematic, cross-sectional illustration of the heart showing an approach to the native mitral valve using a trans-apical puncture, in accordance with various embodiments of the present technology.

An exemplary retrograde approach to the mitral valve is illustrated in FIGS. 1H-1I. The mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. Such access may be achieved with the use of a guidewire 16. Once in place, a guide catheter 14 may be tracked over the guidewire 16. The guide catheter 14 affords subsequent access to permit placement of the prosthetic valve apparatus, as described in more detail below.

In some instances, a retrograde arterial approach to the mitral valve can be preferred due to its advantages. Use of the retrograde approach can eliminate the need for a trans-septal puncture. The retrograde approach is also more commonly used by cardiologists and thus has the advantage of familiarity.

An additional approach to the mitral valve is via trans-apical puncture, as shown in FIG. 1J. In this approach, access to the heart is gained via thoracic incision, which can be a conventional open thoracotomy or sternotomy, or a smaller intercostal or sub-xyphoid incision or puncture. An access cannula is then placed through a puncture, sealed by a purse-string suture, in the wall of the left ventricle near the apex of the heart. The catheters and prosthetic devices disclosed herein may then be introduced into the left ventricle through this access cannula.

The trans-apical approach has the advantage of providing a shorter, straighter, and more direct path to the mitral or aortic valve. Further, because it does not involve intravascular access, it can be performed by surgeons who may not have the necessary training in interventional cardiology to perform the catheterizations of other percutaneous approaches.

The prosthetic treatment apparatus may be specifically designed for the approach or interchangeable among approaches. A person of ordinary skill in the art can identify an appropriate approach for an individual patient and design the treatment apparatus for the identified approach in accordance with embodiments described herein.

Orientation and steering of the prosthetic valve apparatus can be combined with many known catheters, tools and devices. Such orientation may be accomplished by gross steering of the device to the desired location and then refined steering of the device components to achieve a desired result.

Gross steering may be accomplished by a number of methods. A steerable guidewire may be used to introduce a guide catheter and the prosthetic treatment apparatus into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

A guide catheter may be pre-shaped to provide a desired orientation relative to the mitral valve. For access via the trans-septal approach, the guide catheter may have a curved, angled or other suitable shape at its tip to orient the distal end toward the mitral valve from the location of the septal puncture through which the guide catheter extends. For the retrograde approach, as shown in FIGS. 1H and 1I, guide catheter 14 may have a pre-shaped J-tip which is configured so that it turns toward the mitral valve MV after it is placed over the aortic arch AA and through the aortic valve AV. As shown in FIG. 1H, the guide catheter 14 may be configured to extend down into the left ventricle LV and to evert so that the orientation of an interventional tool or catheter is more closely aligned with the axis of the mitral valve MV. In either case, a pre-shaped guide catheter may be configured to be straightened for endovascular delivery by means of a stylet or stiff guidewire which is passed through a lumen of the guide catheter. The guide catheter might also have pull-wires or other means to adjust its shape for more fine steering adjustment.

Treatment of Cardiac Valves

Embodiments of the present technology as described herein can be used to treat one or more of the valves of the heart as described herein, and can be used for treatment of the mitral valve, or in other embodiments, the aortic valve.

FIGS. 2A1 and 2A2 show side and top views of a prosthetic treatment apparatus 100 comprising a valve 150 mounted to a support 110 disposed in a delivery configuration 111, and a plurality of arms 120 in an outward configuration 123 to reach behind leaflets of the mitral valve into the subannular space on the ventricular side of the native annulus. The support 110 is generally cylindrical, being formed around a longitudinal axis 110A. The support 110 comprises an expandable skeleton 140 from which the plurality of arms 120 extend. The support 110 may further comprise a covering (not shown) disposed around the exterior and/or interior walls of the skeleton 140 to block blood flow through the walls of skeleton 140 and/or to promote in-growth of tissue. The arms 120 may also be covered by a coating or covering (not shown) to promote in-growth. The arms 120 can be configured to engage the native annulus such that the valve 150 is supported by the annulus when valve 150 is closed during systole. The plurality of arms 120 can have a column strength to support the valve 150 and maintain its general position relative to the native heart tissue by engaging the annulus as described herein.

The support 110 comprises an upstream portion 112 and a downstream portion 114 and an outer surface 110S. As used herein, "upstream" shall mean the direction from which blood normally flows through the heart or valve in question, while "downstream" shall mean the direction toward which blood normally flows. In the case of the mitral valve, "upstream" means the direction toward or closer to the left atrium or superior aspect of the heart, while "downstream" means the opposite direction, toward or closer to the left ventricle or inferior aspect of the heart. For the aortic valve, "upstream" means the direction toward the left ventricle or inferior end of the heart, while "downstream" means the direction toward or closer to the aorta or aortic arch. In one embodiment, the support 110 comprises a first side 110S1 and a second side 110S2. A first plurality of arms 120A comprising first tip portions 122A can be mounted to the support 110 on the first side 110S1 and a second plurality of arms 120B comprising second tip portions 122B can be mounted to the support 110S on the second side 110S2. A first midline 110M divides the support roughly in half between the first side 110S1 and the second side 110S2, intersecting axis 110A. A second midline 110M2 extends transverse to the first midline 110M, intersecting the midline 110M at the center of the support 110 (FIG. 2A2).

The skeleton 140 may be comprised of a plurality of thin interconnecting members referred to herein as struts 142 or posts 144, arranged in a variety of geometrical patterns. Alternatively, the skeleton 140 may comprise a mesh or woven construction. In one embodiment, the skeleton 140 can include a plurality of struts 142 and a plurality of posts 144. The plurality of posts 144 can extend along an axial direction generally parallel to the longitudinal axis 110A and the struts 142 can extend circumferentially around the longitudinal axis 110A. The struts 142 can form a series of rings around the longitudinal axis 110A, wherein each ring can have a circumferentially expandable geometry. In the example shown, struts 142 are formed in sinusoidal configuration. Zig-Zags, closed cells, open cells, or other expandable configurations are also possible. The plurality of struts 142 can attach to the plurality of posts 144 so as to define a plurality of nodes 110N. The plurality of struts 142 and the plurality of posts 144 may comprise a deformable material or a resilient or shape memory material as described herein. In some embodiments, the plurality of arms 120 may be attached to or otherwise formed integrally with the downstream ends 114*a* of the posts 144 or to locations along the struts 142, or a combination thereof. In other embodiments, the arms 120 can extend from or be coupled to anywhere on the skeleton 140, for example, to an outer surface of a post 144 or strut 142 along the longitudinal axis 110A of the skeleton 140.

The plurality of arms 120 are configured to reach behind the leaflets of the valve and to engage the native annulus. Each of the plurality of arms 120 can comprise a tip portion 122 (e.g., a distal tip) to contact the annulus and a base portion 124 to couple the arm 120 to the support 110. Contact with the annulus may occur, for example, in the annular groove defined by the intersection of the superior portion of the ventricular wall and the root portion the ventricular surface of the mitral leaflets. In one embodiment, the arms 120, when engaging the annulus, are oriented so as to be generally orthogonal to, or at an oblique angle between about 45 and 135 degrees relative to, the subannular surface, such that the loading exerted upon the arms 120 is primarily a compressive, axial load. The tip portion 122 may alternatively be positioned more downstream, that is, anywhere along the ventricular surface of the mitral leaflets or along the ventricular wall. Likewise, the tip portions 122 may not be in substantial contact with any heart structure if, for example, engagement of the plurality of the arms 120 with the chordae tendineae leave the plurality of arms 120 positioned such that the tip portions 122 extend into free space.

Each of the plurality of arms 120 are separated from the support 110 with a gap distance 130 sized to receive the leaflet between each arm 120 and the outer surface 110S of support 110. An elbow portion 126 extends in a downstream direction from the base portion 124 and then makes a turn of about 120-180 degrees in the upstream direction. Each of the plurality of arms 120 may comprise an extension portion 127 extending between the curved elbow portion 126 and the tip portion 122. The elbow portion 126 may comprise a U-shaped curve 126U that extends to the extension portion 127. In some embodiments, the elbow portion 126 can have an arcuate shape, however, in other embodiments, the elbow portion can include a more triangular shape or a square shape that permits redirection of the arm 120 from a downstream trajectory to an upstream trajectory. Each of the plurality of arms 120 can extend a distance 139 below the downstream end 114*a* of the downstream portion 114 of the support 110. The curved elbow portion 126 can extend around an axis 126A located below the downstream end of the support 110. Each of the plurality of arms 110 extends upstream a distance 138 from the downstream end of curved elbow portion 126 to the tip portion 122 so that the tip 122 can engage the native valve annulus while the curved elbow portion 126 can accommodate the downstream edge of the native leaflet. Optionally, the arms 120 may be configured such that the native leaflet is compressed, folded or bunched up toward the annulus when the tip portion 122 is in engagement with the annulus.

The tip portion 122 of each of the plurality arms 120 can be shaped to inhibit penetration of or injury to the annulus. The tip portion 122 may comprise a pressure reducing tip portion 122PR shaped so that the surface area of the tip portion 122 of the arm 120 contacting the annulus is greater than a cross sectional area of the arm 120 away from the tip portion 122.

The tip portions can be oriented so as to have a low profile when the support 110 is disposed in a delivery configuration 111 (FIG. 2A2) and have an engagement profile when the support 110 is in an expanded configuration 113 (FIG. 2A3). Tip portions 122A can be curved or bent around an axis generally parallel to longitudinal axis 110A so that the tips point toward the second midline 110M2 (FIG. 2A2).

Referring to FIGS. 2A2, 2A3 and 2A4 together, the valve 150 can be configured in many ways and may comprise one or more of a temporary valve, a replaceable valve, a removable valve or a permanent valve. The valve 150 comprises a plurality of leaflets 152. In one embodiment, valve 150 has a tri-leaflet configuration, although various alternative valve configurations may be used, such as a bi-leaflet configuration. The valve 150 is adapted to allow blood flow in the downstream direction and to block blood flow in the upstream direction.

FIG. 2A3 shows the apparatus of FIGS. 2A1 and 2A2 with the support 110 in an expanded configuration 113 and the valve open 150. Additionally, FIGS. 2A3-2A4 illustrate an alternative configuration for tip portions 122A, wherein tip portions 122A are bent or curved around an axis transverse to the longitudinal axis 110A so that the tips 122 point generally toward the center of support 110 or toward midline 110M.

FIG. 2A4 shows the apparatus of FIGS. 2A1 and 2A2 with the support 110 comprising the expanded configuration 113 and the valve 150 closed.

FIG. 2A5 shows the geometry and dimensions of an individual arm 120. The arm 120 comprises the elbow portion 126 that can extend the distance 139 below the downstream end of support 110 (not shown in FIG. 2A5). The distance 139 can be within a range from about 0 to about 15 mm, for example about 4 mm. The arm 120 can extend from the lower end of the elbow portion 126 to the tip 122 a distance 137. The distance 137 can be from about 10 mm to about 35 mm, for example about 20 mm. The extension portion 127 can extend at an extension angle 135 relative to the longitudinal axis 110A of the support 110. The extension angle 135 can be within a range from about 10 degrees to about 50 degrees, for example about 25 degrees. The extension angle 135 can determine a gap distance 130 between the tip portion 122 and the outside surface 110S of the support 110.

FIG. 2A6 shows an apparatus 100 implanted at a native valve location in the heart. The arms 120 of the apparatus 100 extend around a leaflet LF between chordae CT of a mitral valve. In some embodiments, the arms 120 on one side of the apparatus 100 can be configured to extend through a gap in the chordae CT near the center of the native leaflet LF. The arms 120 can be sized to extend to the annulus and engage the annulus with the tip portions 122. The arms 120 are splayed circumferentially so that tip portions 122 are spaced apart along the native annulus so as to distribute the load across a wider area of the native subannular surface.

Figure 7C:
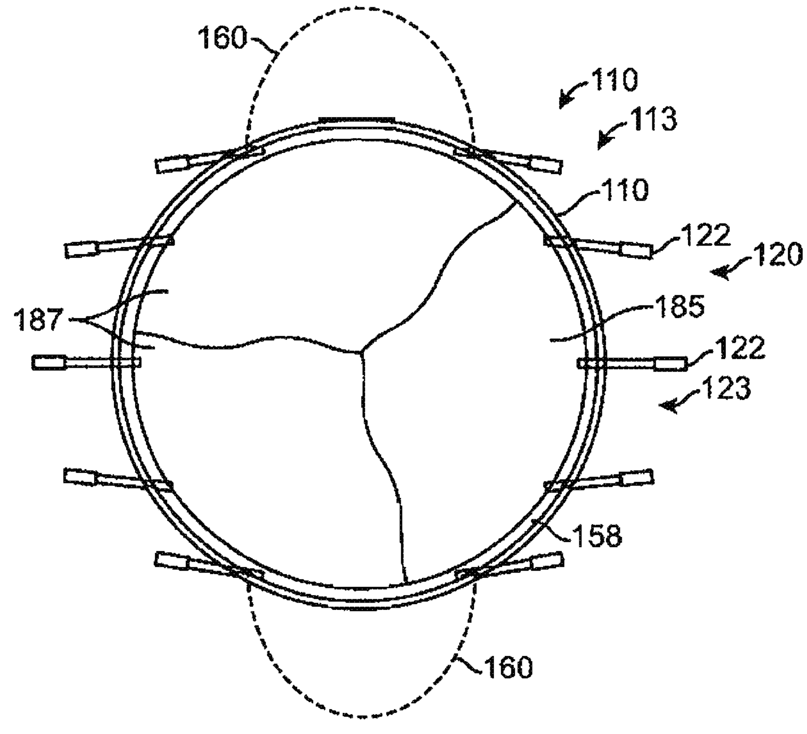
FIG. 7C is a top view of a prosthetic heart valve device having an expandable support with a plurality of arms and a temporary valve mounted within the expandable support configured in accordance with an embodiment of the present technology.

The tip portions 122 may have a variety of configurations adapted to distribute force and minimize tissue injury or penetration of the annulus. FIG. 2A7A shows an arm 120 having a pair of curved tips 122SK on the tip portion 122. The pair of curved tips 122SK of tip portion 122 may comprise curved tips which are sufficiently flexible to be deflected in the downstream direction when engaged by the annulus. The curved tips 122SK may have sufficient resiliency to be biased in an upstream direction toward the annulus so as to maintain contact with the annulus. In this way, the varying elevation of the annulus can be accommodated by the arms 120 so that each of the arms 120 can engage the annulus and bear some of the load exerted on the support 110. Alternatively, the tip portion 122 may comprise round balls as shown in FIG. 2A7B, flattened disk-like structures as shown in FIG. 2A7C, rings as shown in FIG. 2A7D, or other structures. Moreover, in some embodiments, the tip portions 122 are configured to interact cooperatively with the support 110 to enhance engagement with the native valve leaflets. In one configuration, the tip portions 122 point inwardly toward the longitudinal axis 110A and extend over the upstream end of the support 110 such that the native leaflets are sandwiched or compressed between the arms 120 and the support 110 and are folded around the upstream end 112*a* of the upstream portion 112 of support 110 as shown in FIG. 2A7E.

FIG. 2A8 shows a top view of an apparatus 100 wherein the maximum dimension 122MD across each pressure reducing tip portion 122PR is oriented so as to extend generally parallel to the outer surface 110S of the support 110. When the support 110 is in the delivery configuration 111 and the plurality of arms 120 are in the inward configuration 121, the tip portions 122 can nest and conform to the outer surface 110S to decrease the cross-sectional size of the apparatus 100. In some embodiments, adjacent pressure reducing tip portions 122PR can be touching or pressed together on the outer surface 110S of the support 110, or in other embodiments, the pressure reducing tip portions 122PR can be spaced apart along the outer surface 110S by a space 122PRA such that each arm 120 can have a low profile against the support 110 while in the inward configuration 121.

Figure 10:
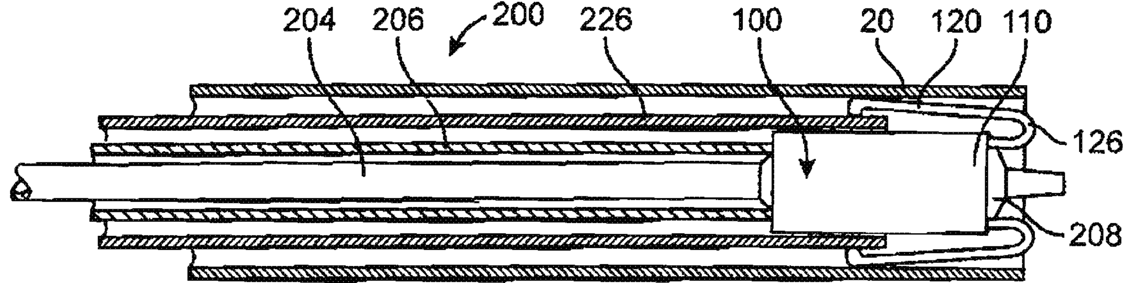

In another embodiment, FIGS. 2A9-2A10 show splay angles of the plurality of arms 120. The support 110 is shown in the delivery configuration 111 and the plurality of arms 120 are shown in the outward configuration 123. Each arm 120 extends from the elbow portion 126 toward the tip portion 122 at unique and variable splay angles off a midline (e.g., the second midline 110M2) such that the plurality of arms 120 are splayed away from each other. In the example shown in FIGS. 2A9 and 2A10, the arms 120 (e.g., arm 120*z*) closest to the second midline 110M2 can have a first splay angle 126SA1 and the arms 120 (e.g., arm 120*x*) farther from the midline 110M2 can have a second splay angle 126SA2 larger than the first splay angle 126SA1. In this example, the tip portions 122 can be spaced apart with respect to each other tip portion 122 and can span a wider distance while contacting the native annulus. In this embodiment, it can be possible to more widely distribute a load on the subannular surface (e.g., pressure or force exerted on the apparatus 100 against the subannular surface of the native annulus at the points of contact with the tip portion 122) when the second/downstream heart chamber contracts. In another configuration, the splay angles 126SA1, 126SA2 are selected such that the individual tip portions 122 of each of the groupings (e.g., rows 128A and 128B shown in FIG. 2A10) of arms 120 on each side of support 110 are clustered together near the midline 110M2. The splay angles may also be selected such that the curved elbow portion 126 forms a helical curve. Alternatively, or in combination, the elbow portion 126 can be twisted such that the extension portion 127 extends to the tip 122 at the selected splay angle. One of ordinary skill will understand that each arm 120 can project from the support 110 at a unique and variable splay angle, with respect to other splay angles of additional arms 120 on the support 110, for accommodating a variety of native structures having differing shapes, sizes and load-bearing potential.

FIGS. 2A10 and 2A11 show top and side views of angles of the plurality of arms 120 relative to the longitudinal axis 110A and configured for treatment of a bi-leaflet or bicuspid valve such as the mitral valve. The support 110 is shown in the delivery configuration 111 and the plurality of arms 120 in the outward configuration 123. The arms 120 are arranged such that tip portions 122 form a first row 128A on the first side 110S1 of the first midline 110M and a second row 128B on the second side 110S2 of the first midline 110M. In one embodiment, the other two sides of support 110, offset roughly 90 degrees from sides 110S1 and 110S2, may have no arms or a much smaller number or lower density of arms than on sides 110S1 and 110S2. In some embodiments, the circumferential distance between an outside arm 120*x* in row 128A and an outside arm 120*y* in row 128B can be substantially larger than the space between adjacent arms (e.g., arm 120*x* and arm 120*z*) in the same row (row 128A or 128B).

First and second rows 128A, 128B of arms 120 may each form a generally straight line, or in other arrangements, may form a peaked or arrow-like shape. In additional arrangements, the arms 120 can be arranged in a curvilinear fashion with a curvature generally matching that of the natural curvature of the native annulus. In some embodiments of devices suitable for treating the mitral valve, which can have a large oval or kidney-like shaped annulus, tip portions 122 in the expanded configuration can be arranged to mimic or match the oval or kidney-like shape of the native annulus and can have a radius of curvature substantially larger than the radius of curvature of support 110. For example, support 110 may have a radius of curvature of about 10-20 mm when expanded, while tip portions 122 may be arranged in a curve having a radius of about 15-30 mm. The first side 110S1 and the second side 110S2 are each divided by the second midline 110M2. To extend the radius of curvature of the tip portions 122 of the collective plurality of arms 120, the arms can have varying splay angles (e.g., splay angles 126SA1 and 126SA2) as discussed above, and the arms 120 can be extended from the longitudinal axis 110A at variable extension angles 135 (shown individually as 135*a* and 135*b* in FIG. 2A11). The extension portion 127 of each arm 120 can extend at an extension angle 135 relative to the longitudinal axis 110A and/or the outside surface 110S of the support 110. In one embodiment, and as shown in FIG. 2A11, the arms furthest from the second midline 110M2 can extend at an extension angle 135*b* relative to the longitudinal axis 110A and the arms closest to the second midline 110M2 can extend at an extension angle 135*a* relative to the longitudinal axis 110A, wherein the extension angle 135*b* is greater than extension angle 135*a*. Referring to FIG. 2A11, the extension portion 127 of the arm 120*z* closest to midline 110M2 extends with a first extension angle 135*a* relative to longitudinal axis 110A and extension portion 127 of the arm 120*x* located farther from midline 110M2 than arm 120*z*, extends with a second extension angle 135*b*, wherein the second extension angle 135*b* is greater than the first extension angle 135*a* such that the plurality of tips 122 on first side 110S1 are linearly aligned to form a generally straight first row 128A and/or have a radius of curvature greater than a radius of curvature of the support 110. For a tri-leaflet or tricuspid valve, arms 120 may be arranged in three groups or rows offset by about 120 degrees from each other circumferentially around the support 110, rather than two groups or rows on opposing sides of the support 110. In other embodiments, the support 110 can accommodate more than three groupings or rows of arms 120.

Figures 2, 2B:
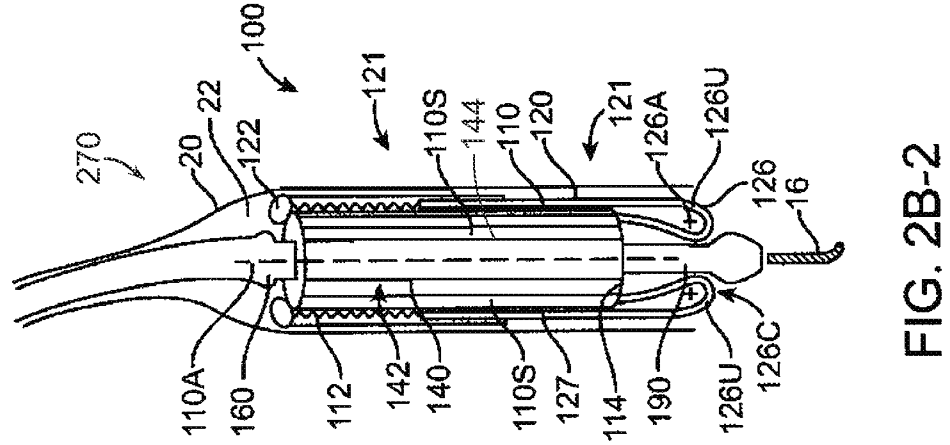
Figures 1, 2B:
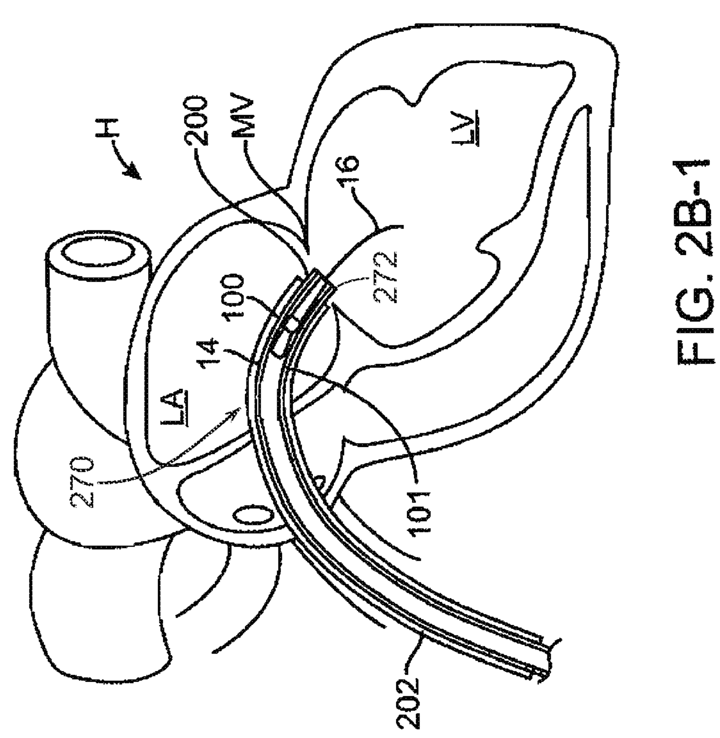

FIG. 2B-1 shows a schematic cross-sectional front elevation view of the heart with a prosthetic treatment apparatus 100 (such as the apparatus 100 of FIG. 2A1) coupled within a lumen 101 near the distal end of a delivery catheter 200 for treatment of the mitral valve MV (chordae tendineae are not shown for clarity). The delivery catheter 200 is inserted through a guide 202 which has been delivered from the right atrium through a trans-septal puncture into the left atrium LA. In some embodiments, a distal portion 270 of the guide 202 is shape-set into a curve such that a distal end 272 of the guide 202 points toward the native mitral valve MV of the heart H.

FIG. 2B-2 shows the distal portion 270 of the delivery catheter 200 of FIG. 2B-1, wherein the prosthetic treatment apparatus 100 is covered with a sheath 20 of the delivery catheter 200. The apparatus 100 can include an expandable support 110 and a plurality of arms 120. Constrained within a lumen 22 of the sheath 20, the expandable support 110 is disposed in a radially-contracted delivery configuration 111 and the plurality of arms 120 are arranged in an inward configuration 121 for percutaneous delivery to the mitral valve MV. The sheath 20 of the delivery catheter 200 can be located over the arms 120 when the support 110 is in the delivery configuration 111 and the plurality of arms 120 are in the inward configuration 121. The apparatus 100 may include an expandable member, e.g. balloon, 190 to expand the support 110, or the support 110 can be a self-expanding support, or combinations thereof. A valve 150 can be mounted within the interior of the expandable support 110, or the valve 150 can be coupled to the support after implantation when the support 110 is in the expanded configuration 113, or combinations thereof as described herein.

Figure 2C:
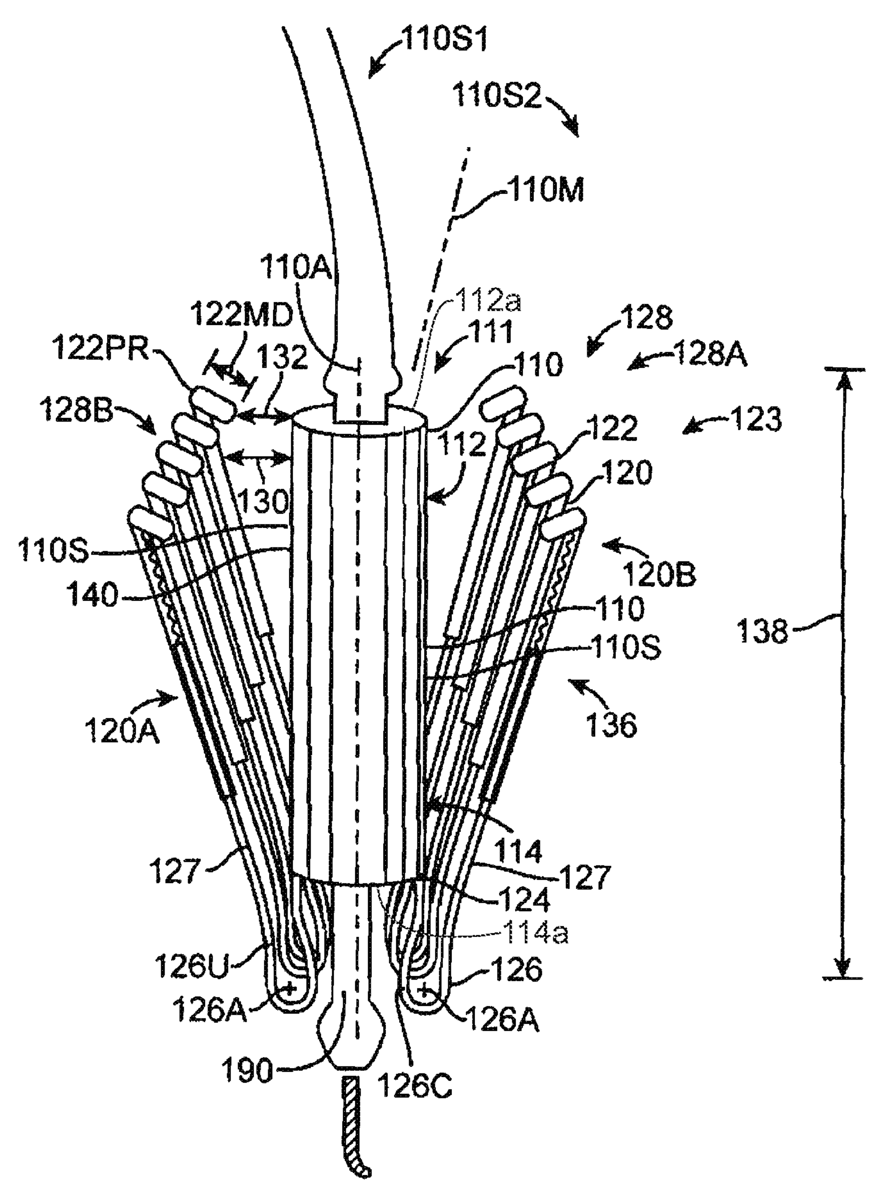
FIG. 2C is an isometric side view of the prosthetic heart valve device of FIG. 2B-2 having the catheter sheath retracted from the plurality of arms and showing the plurality of arms extending outward from the support for positioning at the native valve structure and configured in accordance with an embodiment of the present technology.

FIG. 2C is an isometric side view of the prosthetic heart valve device (e.g., apparatus 100) of FIG. 2B-2 having the catheter sheath retracted from the plurality of arms 120 and showing the plurality of arms 120 extending outward from the support 110 for positioning at the native valve structure and configured in accordance with an embodiment of the present technology. Referring to FIGS. 2A1, 2B-2 and 2C together, the expandable support 110 comprises an upstream portion 112 comprising an upstream end 112*a* of the support 110 and a downstream portion 114 comprising a downstream end 114*a* of the support 110. The support 110 includes an outer surface 110S, which can be covered with a fabric, or other flexible and biocompatible material such as Dacron™, to integrate with tissue and minimize perivalvular leaks. The support 110 can be cylindrical in shape, with a circular, oval, elliptical, kidney-shaped or other suitable cross-section, and defines an axis 110A extending from the upstream portion 112 to the downstream portion 114. The support 110 may comprise a skeleton 140 comprised of a plurality of interconnected struts 142 which are deformable or which resiliently change orientation when unconstrained. The skeleton 140 may comprise a plurality of posts 144 extending between the plurality of struts 142 to provide column strength to the support 110. The plurality of posts 144 and struts 142 have sufficient strength to transfer a force or load applied to the apparatus 100 to the plurality of arms 120. The skeleton 140 can be formed of, for example, one or more of a malleable, balloon-deformable material such as stainless steel or a cobalt chromium alloy such as L605 or MP35N. Alternatively or in combination, the expandable support 110 can include one or more of a resilient material, shape memory material, or superelastic material such as Nitinol, for example. The support 110 may alternatively be composed entirely or partially of a biocompatible polymer, ceramic, textile, or other suitable material.

The arms 120 can include J-hooks, fingers, columns, posts, wires, tubes, ribbons or similar structures having properties such as column strength, flexibility, resilience, etc., suitable for bearing a load or force exerted on the apparatus 100. The arms 120 can have various cross-sectional geometries, including round or polygonal, and can have different geometries at different locations along their length. For example, the curved elbow portions 126 may be circular in cross-section, while other regions of the arms 120, such as those that engage the native leaflets may be more flattened to have a broader area of contact with the leaflets. Referring to FIGS. 2B-2 and 2C together, the plurality of arms 120 are coupled to the support 110 near the downstream portion 114, although the arms 120 may alternatively be coupled to the support 110 at any location within the upstream and downstream portions 112, 114. The arms 120 have a base 124 coupled to the support 110, a tip portion 122 configured to engage the native valve annulus (described more fully below), a curved elbow portion 126 coupled to the base 124, and an extension portion 127 extending between the curved elbow portion 126 and tip portion 122. The arms 120 can be folded against the outer surface 110S of the support 110 in the delivery configuration 111 (shown in FIG. 2B-2). In some embodiments, the tip portions 122 extend above the upstream portion 112 of the support 110 in the inward configuration 121, so as to decrease a cross-sectional size of the apparatus 100 when the support 110 is in the delivery configuration 111 and the plurality of arms 120 are in the inward configuration 121. The tip portions 122 may further be movable to an inward configuration 121 when the support 110 is in the expanded configuration 113, wherein the tip portions 122 contact the native valve annulus very close to the base of each native valve leaflet. The arms 120 may also push the native leaflets against the outer surface 110S of support 110 to help anchor the apparatus 100 to the native tissue and to inhibit perivalvular leaks.

In other embodiments, the arms 120 are shorter in length so as to extend only partially along the length of the support 110, with tip portions 122 being aligned with a middle region (e.g., between portions 112 and 114) of support 110. In the inward configuration 121, the arms 120 may be twisted so that the tip portions 122 are aligned more tangentially with the outer surface 110S of the support 110 so as to lie against the support 110 when covered with the sheath 20 to provide a narrow cross-sectional profile.

The curved elbow portion 126 of each arm 120 may be configured to resiliently urge the arm 120 outward from the inward configuration 121 (FIG. 2B-2) to the outward configuration 123 (FIG. 2C) when the plurality of arms 120 are unconstrained. Referring to FIGS. 2B-2 and 2C together, the curved elbow portion 126 can extend downward (or distally) from the downstream end 114*a* of the downstream portion 114 of the support 110 and define an arcuate or U-shaped turnaround portion 126U from which the extension portion 127 extends upwardly along the outer surface 110S of the support 110. The curved elbow portion 126 may extend about an axis of rotation 126A located below the end 114*a* of the downstream portion 114. Further, the curved elbow portions 126 may extend radially inward toward the central longitudinal axis 110A, which may reduce the overall profile of the apparatus 100 during delivery (shown in FIG. 2B-2). In addition, the delivery configuration may position the elbow portions 126 such that they are engaged by the balloon, if present, used to expand the support 110 from the delivery 111 to the expanded 113 configurations. Upon expansion, the balloon may urge the elbow portions 126 radially outward, thereby urging tip portions 122 radially inward toward the outer surface 110S of the support 110. This may help to push the leaflet tissue against the support 110 for improved perivalvular sealing, and may further compress the leaflet tissue between the arms 120 and the support 110, thereby enhancing the anchoring of apparatus 100.

The plurality of arms 120 can be a unitary or integral part of the support 110 or, in another embodiment, the arms 120 can be welded, bonded, pinned, pivotably or slidably coupled by a hinge or sliding mechanism, or otherwise affixed to the support 110. In some embodiments, the arms 120 and support 110 are laser cut from a single tube of material such as stainless steel or cobalt chromium alloy. The arms 120 can then be formed into the desired unbiased configuration, optionally using heat to assist in forming or setting the ultimate shape.

In some arrangements, the plurality of arms have sufficient column strength and resistance to buckling to maintain the position of the support 110 relative to the native valve by engagement of the arms 120 with the annulus, as described more fully below. In the same or other arrangements, the arms 120 can have sufficient resilience to self-expand from the inward configuration 121 when unconstrained, and have sufficient flexibility to be deflected and repositioned when encountering rigid tissue structures during deployment.

The loading of the plurality of arms 120 will depend on the size of the native valve and the subject's blood pressure. As shown in Table 1 below, for a valve 25 mm in diameter, the force of blood pressure during systole can exert a load of about 1.8-3.1 lbf (about 7.8 N-13.7 N) on the support 110. For a valve 29 mm in diameter, the systolic load on the support may be about 2.4-4.2 lbf (10.6 N-18.5 N). This load is distributed across the features that are in contact with the anatomy. The load may be supported by the arms 120, and, in one embodiment, the load may be spread evenly among the arms 120, so that the load can be divided by the number of arms. For example, with an apparatus having 10 arms, each individual arm 120 may see a load of about 0.2-0.4 lbf (1.1 N-1.9 N). In these arrangements, the arms 120, when restrained by engagement with the annulus, have a column strength sufficient to withstand these forces without buckling. Some flexing or slight deformation may be acceptable in some embodiments, however, arms 120 generally are configured to maintain the position of the support 110 relative to the annulus while under this loading. In other arrangements, the load may not be spread evenly among the arms 120 such that the load is distributed to individual arms in an uneven or variable manner. In these arrangements, the arms 120 can be configured to withstand higher loads, e.g. for a 10-arm embodiment, each arm can be configured to withstand a load of at least about 0.5 lbf, or in another embodiment at least about 1 lbf, and in a further embodiment at least about 2 lbf, without buckling, fracturing or otherwise failing. In embodiments with fewer arms, higher loads can be encountered by each individual arm, while devices having more arms may have each arm 120 receiving lower loads.

TABLE 1

Mitral Valve Load Parameters.

| Systolic pressure | | Load on 25 mm valve | | Load on 29 mm valve | |
|---|---|---|---|---|---|
| (mm Hg) | (N/mm^2) | (N) | (lbf) | (N) | (lbf) |
| 120 | 0.0160 | 7.8 | 1.76 | 10.6 | 2.37 |
| 210 | 0.0280 | 13.7 | 3.09 | 18.5 | 4.15 |

The values of Table 1 are based on the following model aspects and values. The systolic pressure acts as the pressure gradient on the mitral valve even though there is some pressure in the left atrium, and the true pressure gradient is less than the peak systolic pressure. The systolic pressure is shown for ranges from about 120 mmHg (normal) to 210 mmHg (far above the 160 mmHg threshold for Stage 2 hypertension). The pressure gradient is applied to the valve area, so for a given pressure, the larger the valve area, the greater the load.

The arms 120 can be sized and positioned in many ways so as to have a combination of rigidity, flexibility, and resilience that is appropriate for deploying and anchoring a replacement heart valve. The arms 120 may comprise sufficient rigidity to brace against the subannular rim and to push against the leaflets and/or chordae (for mitral valve replacement devices) so as to maintain position of apparatus 100 with respect to the native valve. For example, assuming a hypertensive systolic pressure of 200 mm Hg (0.0266 N/mm2) acting as a pressure gradient on a 25 mm diameter valve, the load on the device can be about 13.1 N (2.94 lbf). Divided evenly across 10 arms, each arm will receive a load of 0.294 lbf. For a stainless steel arm, each arm may have a circular cross-section with a diameter of at least about 0.016 in (0.41 mm), a length of 0.787" (20 mm), and may be angled at about 15-20° away from the skeleton body.

The material and geometry selected for the arms can be used to determine the necessary dimensions. For an arm made from 316 stainless steel having minimum ultimate tensile strength of about 75 ksi (per ASTM A240), a minimum arm diameter may be 0.016", for example. Arms of different cross-sectional shapes can have a similar bending moment of inertia, and increasing the number of arms on a prosthetic heart valve device can allow for a decrease in individual arm cross-sections. In some embodiments, weaker, softer, more brittle, or more flexible materials may require larger cross-sectional dimensions and/or more rigid geometries.

Referring back to FIGS. 2B-1 and 2B-2, the arms 120 can fold up against the skeleton 140 of the support 110 to create a compact profile for transcatheter delivery, which can be achieved with flexibility and/or a small cross-section, for example. Various embodiments of the apparatus 100 can be sized to fit in a 24 Fr lumen catheter (approximately 8 mm in diameter) for delivery. For example, the support 110 in the delivery configuration 111 may have a diameter of about 6.5 mm, and the plurality of arms 120 in the inward configuration 121 may add an additional 0.75 mm, such that the total diameter of the apparatus 100 can be about 8 mm or less which can be accommodated in the 24 Fr lumen catheter.

The plurality of arms 120 may nest within recesses or holes (not shown) in the outer surface 110S of the support 110 to reduce an overall profile or to accommodate a support 110 having a larger cross-section.

Referring to FIG. 2C, the plurality of arms 120 can be resilient to deploy away from the support 110 with a sufficient gap for receiving the native valve leaflets between the arms 120 and the skeleton 140. The plurality of arms 120 can be deployed away from the support 110 using a variety of mechanisms and resilient materials. In some embodiments, the arms 120 are resiliently biased toward the outward configuration 123 and may be deployed by retracting the sheath 20 (shown in FIG. 2B-2), or extending the device 100 out of a cannula, or otherwise releasing the arms 120 from a radial constraint. The arms 120 may further be configured to move radially inward relative to the outer surface 110S of support 110 when the support 110 is expanded to the expanded configuration 113. In this way, the arms 120 may engage and grip the native leaflets as the skeleton 140 expands, sandwiching the leaflets between the arms 120 and the support 110 so as to a) reduce perivalvular leaks around the outside surface 110S of the support 110, and b) to enhance the anchoring of the device 100 to the native valve structure. In alternative embodiments, the arms 120 may be unbiased and instead, configured to naturally reside in an inward position (e.g., configuration 121) close to or against the outer surface 110S of the support 110, or in another embodiment, in an intermediate position between an outward configuration for receiving the leaflets, and an inward configuration against the support 110. Further, the radial expansion of support 110 from the delivery configuration 111 to the expanded configuration 113 can close the gap between the arms 120 and the support 110, such that the arms 120, when unbiased, are disposed against or in close proximity to the outer surface 110S of the support 110.

In various arrangements of the prosthetic heart valve device disclosed herein, the plurality of arms 120 may be sufficiently rigid so as to be pushed or pulled up along the ventricular wall; however, the arms 120 can also be provided with flexibility and resilience so that the arms 120 or tip portions 122 do not damage cardiac tissue or get snagged in recesses in the wall of the downstream heart chamber. The plurality of arms 120 may also have flexibility and resilience so as to be deflected out of the way if engaged by obstructions such as papillary muscles and chordae as the arms are moved into position and engage a subannular surface of the annulus. The arms 120 may also be flexible and resilient so as to absorb some of the cyclic loading experienced by an implanted apparatus 100, and to decrease irritation and puncture of anatomical structures following implantation.

During percutaneous delivery, the support 110 and the plurality of arms 120 may be held within catheter 20 in a compressed configuration, with an overall diameter of about 5-8 mm, for example, with the support in the delivery configuration 111 and the plurality of arms in the inward configuration 121 (shown in FIGS. 2B-1 and 1B-2). In some embodiments, the arms 120 or, selectively, outmost arms 120 of each row 128 or groupings of arms 120, can be rotated against the support 110 to decrease the overall transverse profile, for example by twisting, bending, or folding individual arms 120 (FIG. 2A2). In other arrangements, any arm 120 or selected individual arms can be rotated to decrease the overall transverse profile.

FIG. 2C shows an isometric view of the prosthetic treatment apparatus 100 wherein the support 110 is in the delivery configuration 111 (sheath 20 in FIG. 2B2 pulled away) and arms 120 are extending outward from the support 110 in the outward configuration 123 for placement behind the native leaflets. FIG. 2C1 shows a top (upstream) view of the apparatus 100 configured as shown in FIG. 2C. When the tip portions 122 of plurality of arms 120 are positioned distally of the native leaflets, the sheath can be withdrawn to allow the arms to move from the inward configuration 121 to the outward configuration 123.

In the relaxed and unbiased outward configuration 123, the plurality of arms 120 may extend radially outward from the support 110 at various angles (e.g., extension angles 135 and splay angles 126SA) and in a generally upstream direction providing a gap distance 130 between the arms 120 and the outer surface 110S of the support 110 (FIGS. 2A5, 2A9-2A11). In some embodiments, the arms 120 can be arranged at extension angles 135 within a range from about 5-40 degrees, or in other embodiments from about 10-30 degrees, relative to the outer surface 110S (or axis 110A) and while in the outward configuration 123 (shown in FIGS. 2A5 and 2A11).

Referring back to FIG. 2C, each of the plurality of arms 120 includes a base portion 124 and each arm can extend from the base portion 124 to a tip portion 122. Each base portion 124 couples the arm 120 to the downstream portion 114 of the support 110. The base portion 126 can be coupled to the support 110 using a variety of techniques known in the art (e.g., welding, pins, clips, adhesives or other mechanical techniques for attaching the base portion 126 of the arm 120 to the support 110). In one embodiment, the base portion 124 of each arm 120 may be integrally formed with the arm 120 and, in some arrangements to the support 110. In another embodiment, the base portion 124 may comprise a separate component which is welded, pinned, or otherwise coupled to the arm 120 and/or support 110. The base portion 124 may comprise a movable coupling or a component of a movable coupling (e.g., mechanism) such that the arms 120 or portions of the arms (e.g., base portion 124, elbow portion 126 and or extension portion 127) are length and/or height adjustable. In one example, the base portion 126 may be sized to pass through a tube welded to the downstream portion 114 so that the base portion 126 can slide through the tube to alter the height of the tip portion 122 relative to support 110.

As shown in FIG. 2C, intermediate or elbow portion 126 can extend from or otherwise be attached to the base portion 124. The elbow portion 126 can be curved or arcuate in shape and may be configured to deform in a manner which repositions the arm 120 when the support 110 is expanded from the deliver configuration 111 to the expanded configuration 113. In this manner, the elbow portion 126 is configured to vary the gap distance 130 between the outer surface 110S and the tip portions 122 (refer also to FIG. 2A5). In one or more embodiments, the elbow portion 126 has a cam portion 126C positioned to be engaged by a deployed balloon of the delivery catheter. The cam portion 126C can be displaced radially outward away from the longitudinal axis 110A of the support 110 by the balloon such that the cam portion 126 is outside of a vertical alignment with the support 110 and so as to reposition the arm 120 to bring the tip portions 122 closer to the outer surface 110S (e.g., decrease the gap distance 130). This radially outward displacement of the cam portion 126C can position the plurality of arms 120 closer to the outer surface 110S such that the outward configuration 123 comprises a second outward configuration 123B to compress the leaflets between the arms 120 and the outer surface 110S of the support 110, for example.

As described above, when the arms 120 are in the outward configuration 123 and the support 110 is in the unexpanded delivery configuration 111, the individual arms 120 each extend away from the surface 110S of the support 110 by the gap distance 130. The gap distance 130 may correspond to a radial distance extending between the outer surface 110S and the tip portion 122 of each arms 120, or alternatively, may correspond to another radial distance extending between the outer surface 110S and another position along the extension portion 127 of the arm 120.

Referring to FIGS. 2C and 2C1 together, the plurality of arms 120 may comprise a first plurality of arms 120A extending along a first row 128A and a second plurality of arms 120B extending along a second row 128B. The first plurality of arms 120A can receive a first leaflet and the second plurality of arms 120B can receive a second leaflet.

In one embodiment, the plurality of arms 120A and 120B may be arranged in two rows 128A and 128B, respectively, on opposing sides of the support 110. The gap distance 130 of each of the plurality of arms 120A, 120B may vary among individual arms. For example, arms 120 closest to the second midline 110M2 of the support can have a first gap distance 130 while arms furthest from the second midline 110M2 can have a second gap distance 130 greater than the first gap distance 130. In this embodiment, the gap distances 130 can be arranged such that the arms 120 and/or tip portions 122 can be aligned in generally straight or, in another embodiment, curvilinear rows 128. As described herein, rows 128 may comprise a generally straight line, a curved line, a zig-zag, sinusoidal shape, or other configuration. In some embodiments, the rows 128 are straight or form a slight curve with a radius of curvature substantially larger than that of the outer surface 110S. While a row 128 is shown, the gap distance 130 of each of the tip portions 122 may be varied in many ways to achieve a variety of different arrangements of arms 120 or tip portions 122 so as to position the tip portions 122 against the native annulus and/or to receive the leaflets of the treated valve (e.g., the mitral valve).

In additional arrangements, arms 120A on a first side 110S1 of support 110 may be different in number, may be in a different arrangement, may be disposed at different angles (e.g., extension angles 135 or splay angles 126SA) in the outward configuration 123, may have different sizes or shapes, may be more or less flexible, or may have other properties different than the arms 120B on a second side 110S2 of the support 110. This enables the arms 120 in each row 128A or 128B, or other groupings of the arms 120, to be tailored to receive a particular leaflet of the native valve and/or accommodate the unique physiology of particular leaflet and surrounding anatomy. For a particular valve, such as the mitral valve, in which the two leaflets are very different in shape and size, and where the surrounding anatomy is very different around the anterior leaflet than around the posterior leaflet, this variability and independent adaptability of the arms 120A, 120B on different and/or opposing sides of the support 110 can be useful for providing unique and custom fits of the devices/apparatuses to target native valve structures in a variety of patients and in a variety of unique disease states. In particular, in the case of the mitral valve, the anterior leaflet is disposed adjacent to the left ventricular outflow tract (LVOT) for which, in some embodiments, obstruction should be avoided. Further, the wall of the left ventricle is farther away from the anterior leaflet than a corresponding distance to the ventricle wall near the posterior leaflet. As such, arms 120A, for example, configured to capture and engage the anterior leaflet may not be able slide along a wall of the ventricle to guide the arms to the subannular surface. Thus, in some embodiments, arms 120A on the first side 110S1 of support 110 can be configured, in the outward configuration 123, to extend from the support 110 at a shallower angle and/or to have a shorter gap distance 130 than the arms 120B on the second side 110S2 of the support 110 (shown in FIG. 2C1). In this way, the arms 120A on the first side 110S1 can be positioned to capture the anterior leaflet while minimizing obstruction of the left ventricular outflow tract, and the more widely separated arms 120B on the second side 110S2 can more easily capture the posterior leaflet while being guided toward the annulus by engagement with the left ventricular wall.

The first plurality of arms 120A and the second plurality of arms 120B can be arranged in many ways to receive the corresponding first or second leaflets. The first plurality of arms 120A and the second plurality of arms 120B may comprise similar components oriented around the longitudinal axis 110A so as to define one or more planes of symmetry. For example, the first plurality of arms 120A can extend from a first side of the support 110S1 and the second plurality of arms 120B can extend from a second side of the support S2, wherein a midline 110M divides the support 110 between side 110S1 and side 110S2. A second midline 110M2 perpendicular to midline 110M can further divide each of the first side and the second side. In some embodiments, the gap distance 130 associated with each individual arm 120 can increase progressively with respect to distance from the second midline 110M2. With aortic or other tri-leaflet valve embodiments, the first plurality of arms 120A may extend from a first portion of the support 110, the second plurality of arms 120B may extend from a second portion of the support 110, and a third plurality of arms (not shown) may extend from a third portion of the support 110, forming three rows in a generally triangular shape such that each of the plurality of arms 120 extending from the corresponding portions of the support 110 can be aligned with one of the native valve leaflets.

As described above, the plurality of arms 120 in each row 128 can be splayed away from each other arm 120. The plurality of arms 120 can extend from the base portions 124 to the tip portions 122 at different splay angles (e.g., 126SA1 and 126SA2 shown in FIG. 2A9) so that a distance between adjacent tip portions 122 is greater than a distance between adjacent base portions 124. For example, the arms 120 further from the second midline 110M2 (such as arm 120*x* shown in FIG. 2A10) can have a greater splay angle relative to the axis 110A, than those arms 120 closer to the second midline (such as arm 120*z* shown in FIG. 2A10). The plurality of arms 120 in each row 128 might alternatively be biased toward the second midline 110M2 so as to be grouped more tightly together. In this embodiment, the distance between adjacent tip portions 122 is less than a distance between adjacent base portions 124. This arrangement may facilitate the placement of the group of arms 120 through a gap in the chordae near the center of a native mitral valve leaflet.

The plurality of arms 120 can be configured to deflect laterally in response to tissue resistance. For example, each the plurality of arms 120 can be configured to deflect in response to contact with one or more of the chordae tendineae, such that the arm 120 can deflect away the chordae tendineae to avoid entanglement and decrease distortion to the leaflets as the arms 120 are advanced toward the annulus. For example, the elbow portion 126 of each arm 120 can be configured to allow deflection of the tip portion 122, while the extension portion 127 can provide suitable column strength to the arm 120. Accordingly, the elbow portion 126 may comprise a flexible material having a sufficient resiliency so as to assist transition of the arm 120 between the inward configuration 121 and the outward configuration 123, and so as to deflect in response to contact with the chordae or other heart tissue. In some embodiments, the arm 120 may comprise materials similar to the skeleton of the support 110, while the cross-sectional size and curvature of the elbow portion 126 can be configured to provide resilient deflection of tip portions 122 without substantial deformation of the shape and positioning of the elbow portion 126.

In accordance with some embodiments of the present technology, the tip portion 122 of the plurality of arms 120 can be configured to avoid trauma to and inhibit penetration of the annulus or other heart tissues. The tip portion 122 may comprise a surface or material to atraumatically contact and/or engage the annulus while avoiding penetration of the annulus tissue. In some embodiments, the tip portion 122 of each of the plurality of arms 120 may comprise a pressure reducing tip portion 122PR. The pressure reducing tip portion 122PR may comprise any of various structures configured to distribute force over a wider area of contact and avoid penetration of the tissue. Such structures can include, for example, a bumper, broadened foot, disk, curved tip, loop, tube, cap, eyelet, mitten, sleeve, sheath, ball, golf club head-shaped, teardrop shaped structure or other such structures known in the art configured to atraumatically apply pressure to tissue while avoiding penetration or trauma to the tissue. In the embodiment shown in FIG. 2C, pressure reducing tips 122PR can be formed at a right angle to extension portions 127 and generally orient inwardly toward the longitudinal axis 110A. The upstream-facing surfaces of the pressure reducing tips 122PR can be flattened and broadened to increase the area of contact with the annulus tissue. In some embodiments, the pressure reducing tips 122PR can be configured to extend over the upstream end 112Aa of the support 110 so as to minimize the cross-sectional profile of the apparatus 100 while in the delivery configuration 111. Alternatively, arms 120 may be shorter in length, and the pressure reducing tips 122PR may extend into holes or recesses in the outer surface 110S of the support 110. In various embodiments, the pressure reducing tip portion 122PR may be integrally formed with the arm 120 or may be a separate component of the arm that is welded, bonded, mechanically attached or otherwise coupled the arm 120. The pressure reducing tip 122 PR may be the same material as the arm 120 or may be a different material, including metal, polymer, fabric, ceramic or other biocompatible material. In some embodiments, the pressure reducing tip portion 122PR can have a maximum cross-sectional area corresponding to a maximum dimension 122MD across the pressure reducing tip portion 122PR (shown in FIG. 2C). The cross-sectional area of the pressure reducing tip portion 122PR can be greater than a maximum cross-sectional area of the base portion 124, a maximum cross-sectional area of the curved elbow portion 126, or a maximum cross-sectional area of the extension portion 127, for example. Alternatively, the tip portion 122 contacting the annulus may comprise a cross-sectional size and maximum dimension 122MD similar to the base portion 124, the elbow portion 126 and/or the extension portion 127. For example, each arm 120 may extend from the base portion 124 to the end of the tip portion 122 with a substantially uniform cross sectional size, and the cross-sectional size of the tip portion 122 can be sufficiently large so as to inhibit penetration of the annulus. The pressure reducing tip portion 122PR may also comprise a sleeve of flexible material such as, for example, Dacron™ or PTFE placed over each tip portion 122 and adapted to not only inhibit penetration of the annulus, but, in some embodiments, to encourage or promote in-growth of tissue around the tip portion 122.

While in some embodiments, it generally can be desirable to avoid trauma and penetration of the native annulus, in some embodiments the tip portions 122 may be configured to penetrate the annulus partially or entirely in order to more securely anchor the apparatus 100 to the native valve. In such embodiments, tip portions 122 may include sharpened distal tips to enable penetration, and/or barbs, hooks or other suitable structures to resist removal from the tissue after penetration. In addition, the tip portions 122 may further include a depth limiting structure such as a hilt or flange extending around the arm 120 spaced a desired distance from the tip portion 122 to limit the depth of penetration into the annulus. In some embodiments (not shown), the sharpened distal tips may be retractable within the extension portions 127 of the arms 120 such that the penetrating portions (not shown) can be in a retracted state while the apparatus 100 is being positioned with the native valve region and can be in an extended state when contact is made with the desired target region of the subannular surface, for example. In this manner, the sharpened tip portion and/or penetrating tip portions can avoid trauma, cutting, or scraping of any other heart tissue during deployment.

In further embodiments, the extension portion 127 and/or the tip portion 122 of each of the plurality of arms 120 may comprise one or more of an anchoring structure, barb, bump, ridge, scale, sintering, a roughened surface, polymeric or fabric coverings, or hooks on their upstream and/or inward-facing surfaces configured to enhance friction with or couple to the annulus, back sides of the native leaflets, chordae, heart wall, or other surrounding structures to inhibit movement of the apparatus 100 once implanted.

Referring to FIG. 2C2, each of the plurality of arms 120 can optionally include a length adjusting mechanism 136 to adjust a length of the arms and/or the height 138 of tip portions 122 relative to support 110 and/or elbow portion 126 in response to contact with the annulus. In some embodiments, the length adjusting mechanism can be self-adjusting, and in other embodiments, the mechanism can be manually or operatively adjustable. In a further embodiment, the mechanism 136 may be configured to lock each of the arms 120 into position with a desired degree of axial rigidity when the arm 120 engages the annulus at the desired height 138. In some embodiments, the height 138 of each of the tip portions 122 may correspond to a distance along the axis 110A between the tip portion 122 and the base portion 124. In some embodiments, the mechanism 136 may comprise one or more of a spring, a slider, a hypo tube, a telescopic joint or a deflectable portion of the plurality of arms. One of ordinary skill will recognize other mechanisms 136 suitable for self adjustment or manual adjustment of arm length.

In some arrangements, the plurality of self-adjusting arms 120 can be well suited for use with devices used to implant at the native mitral valve region, as the mitral valve may have a non-uniform geometry that can vary among patients. In one embodiment, the mechanism 136 may comprise a telescopic configuration for adjusting and locking each arm 120. In one example, the tip portions 122, which may include a bumper or enlarged surface, may be coupled to a hypodermic tube 136T which can slide up and down over an extension portion 127 of the arm 120. An internal compression spring 136S may bias the tube 136T in an upstream direction so tip portions 122 are urged toward the annulus. The springs 136S may be further compressible from this position in response to tissue contact. When the support 110 is moved in an upstream direction with the plurality of arms 120 extending behind the leaflets, the arms 120 which contact the lower portions of the annulus first can start to compress, so as to allow additional arms 120 to contact the higher portions of the annulus. In exemplary embodiments, the height 138 of tip portions 122 will be self-adjusting within a range of about 1-15 mm to maintain engagement with the higher and lower portions of the annulus.

The self-adjusting the length of the arms 120, for example due to the internal springs 136S, can be expected to last a few hours after implantation. After that time, blood in the space between the hypo tube 136T and the strut over which it slides may cause the mechanism 136 to seize up or otherwise prevent further movement, thereby locking the mechanism 136 and providing a stable or static length of the arm 136. In the locked configuration, the plurality of arms 120 can support the hemodynamic load applied to the apparatus 100 with each second heart chamber contraction (e.g., heartbeat). It is also understood that the mechanism 136 to adjust and lock each arm 120 can be formed in additional ways, including, for example with telescoping tubes fitted with friction locks, spring buttons, cam locks, ratchet system, or hydraulic pressure resistance.

When the apparatus 100 has been positioned in the left ventricle with the arms 120 released in the outward configuration as shown in FIG. 2C, and the support 110 still in the unexpanded delivery configuration 111, the apparatus 100 can be moved up, down or sideways as appropriate so as to allow the arms 120 to slip around the lower edges of the leaflets, through the gaps between the chordae (if being placed at the mitral valve region), and into the space "behind", i.e. radially outside, the native valve leaflets. In some embodiments, the arms 120 are arranged such that most or all of the tip portions 122 are disposed in a middle region of each leaflet where there are fewer chordae and a significant gap is present between the groups of chordae going to each papillary muscle. Accordingly, the arms 120 can pass through the chordae toward the annulus.

The plurality of arms 120 may comprise a first outward configuration 123A prior to expansion of the balloon (not shown) and a second outward configuration 123B after expansion of the support 110 with the balloon and as illustrated in FIGS. 2C3 and 2C4, respectively. Referring to FIG. 2C3 and in the first outward configuration 123A, each of the plurality of arms 120 are separated from the outer surface 110S of support 110 by a gap distance 130A, and each of the tip portions 122 are separated from the outer surface 110S by a gap distance 132A. The arcuate or elbow portion 126 extends below the downstream portion 114 of the support 110 so as to engage the balloon, if present, with the cam portion 126C, as described above. When the support 110 expands from the delivery configuration 111 to the expanded configuration 113, the balloon can engage the cam portion 126C urging the plurality of arms to transition from the first outward configuration 123A to the second outward configuration 123B. The cam portion 126C can move radially outward away from the longitudinal axis 110A of the support such that the cam portion 126, in some embodiments, is outside of a vertical alignment with the support 110. As the cam portion 126 moves radially outward with pressure from a balloon or other expansion device, the axis 126AA (FIG. 2C3) is moved outward to axis position 126AB (FIG. 2C4) and the extension portion 127 and the tip portion 122 are both urged closer toward the outer surface 110S. The gap distance 130B between the arms 120 and the outer surface 110S is decreased in the second outward configuration 123B as compared to the first outward configuration 123A, and the gap distance 132B between the pressure reducing tip portion 122PR and the outer surface 110S is similarly decreased in the second outward configuration 123B. As the arms 120 transition from the first outward configuration 123A to the second outward configuration 123B, the arms 120 can engage and trap the leaflet against the outer surface. In some embodiments, the plurality of arms 120 can include a shape memory material which can promote similar movement between the configurations 123A and 123B.

In addition to the inward movement of the arms 120 relative to the outer surface 110S, the plurality of arms 120 can have a twisting action when transitioning from the first outward configuration 123A to the second outward configuration 123B, as shown schematically in FIGS. 2C5 and 2C6, respectively. In the first outward configuration 123A as seen from the downstream direction shown in FIG. 2C5, the cam portion 126C of each of the plurality of arms 120 extends inclined at an angle away from the axis 110A. When a delivery balloon expands (not shown), the cam portion 126C engages the balloon and twists the arm 120 about base portion 124 and moves the tip portion 122 toward the outer surface 110S with twisting movement 123T. The twisting can splay the arms 120 when the support 110 expands (FIG. 2C6). The twisting of arm 120 about the base portion 124 allows the arm 120 to be drawn toward the annulus (not shown) from a location along the leaflet having few chordae (FIG. 2C5) to a position that engages the annulus and extends along the leaflet to locations having a higher density of chordae (FIG. 2C6). The plurality of arms 120 can be configured to move similarly with shape memory material, for example.

Figures 2D, 2E:
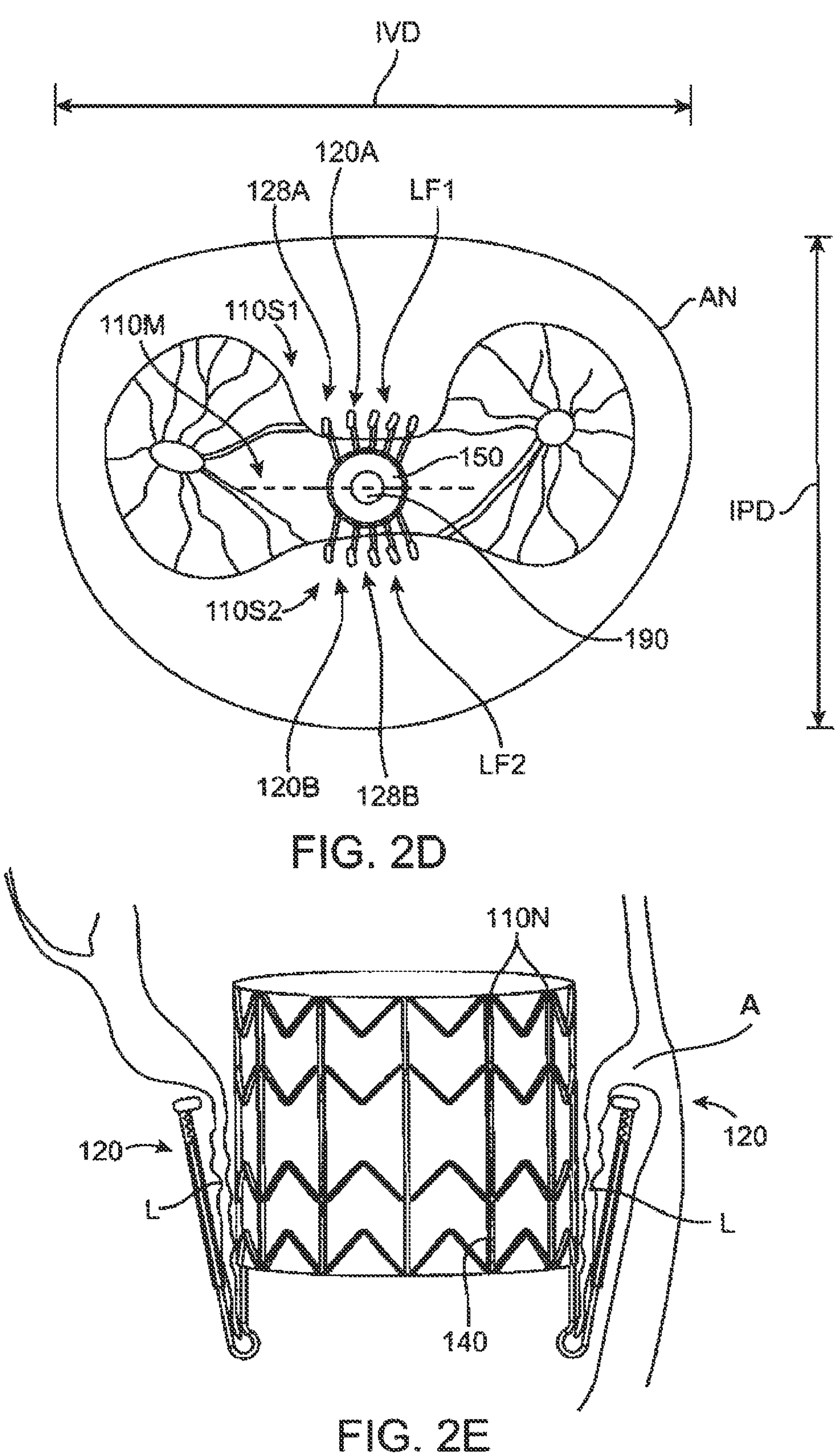
FIG. 2D is a schematic illustration showing a view from above of a prosthetic heart valve device having a plurality of arms positioned behind central portions of the native valve leaflets in accordance with various aspects of the present technology.
FIGS. 2E and 2F are side and top views, respectively, of a prosthetic heart valve device positioned within a native valve and showing a support in an expanded configuration and a plurality of arms extending outward from the support to reach behind native leaflets and engage a subannular region of the native annulus in accordance with various aspects of the present technology.

FIG. 2D is a schematic illustration showing a view from above of a prosthetic heart valve device (such as apparatus 100) positioned within a native valve and showing the support 110 in an expanded configuration 113 and the plurality of arms 120 extending outward from the support 110 to reach behind native leaflets along a central portion of the leaflets between the chordae tendineae CT, and engage a subannular region of the native annulus AN. For clarity, the tips 122 of the arms 120A, 120B are shown in FIG. 2D even though they are below the leaflets of the native valve. The rows 128A and 128B of the plurality of arms 120A, 120B and the midline 110M can be aligned with the long dimension of the annulus AN, such that one leaflet (shown individually as LF1 and LF2) can be engaged with each row (row 128A and 128B, respectively). For the mitral valve, the arms 120 can be configured to slip between the chordae tendineae in proximity to the edge of the leaflets LF1 and LF2, rather than down closer to the papillary muscles. Ultrasound, such as an echocardiogram, or fluoroscopic imaging can be used to align the first plurality of arms 120A and the second plurality of arms 120B with the long dimension of the mitral valve and to confirm this alignment and positioning.

Figure 2F:
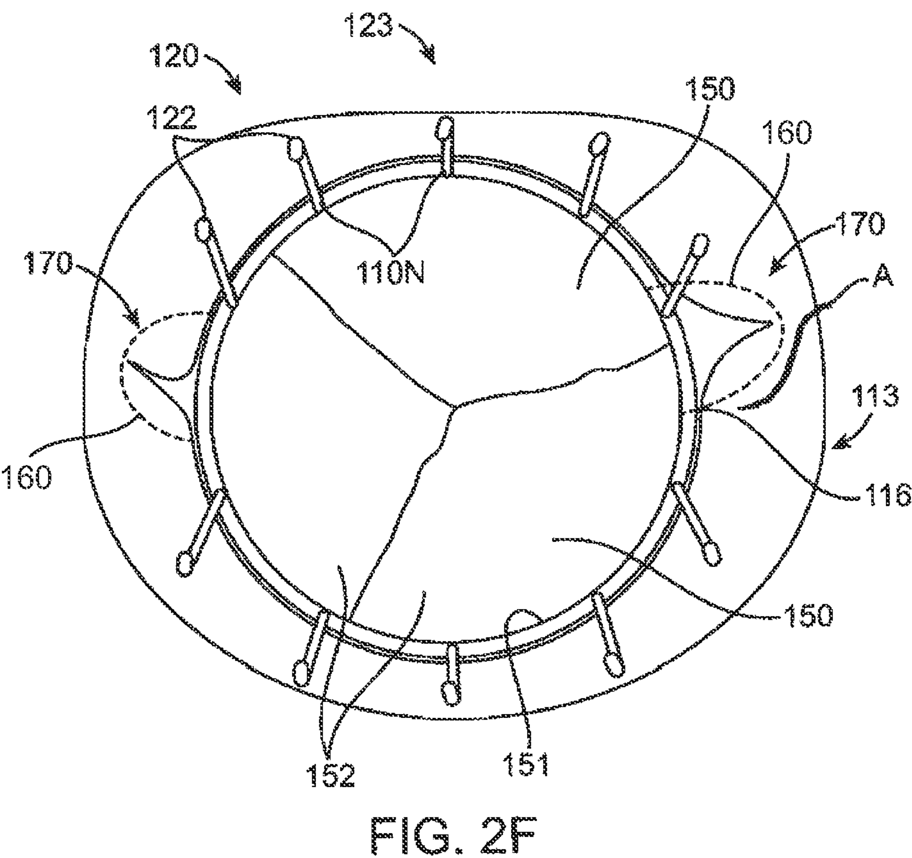

FIGS. 2E and 2F are side and top views, respectively, of a prosthetic heart valve device (such as apparatus 100) showing the support 110 in an expanded configuration 113 and in position within the native mitral valve. The arms 120 are shown in FIG. 2F for clarity, even though they would otherwise be obscured from view by the native leaflet. When each of the plurality of arms 120 has been determined to be appropriately positioned behind the leaflets L, the apparatus 100 can be moved in the upstream direction until the tip portions 122 of the arms 120 are placed against the annulus A. The surgeon may feel or otherwise sense the arms 120 contacting the annulus A when the support 110 is moved and guided along the native valve. Depending upon which native valve is being replaced and from which access site as described herein, the apparatus 100 may be pulled or pushed so as to engage the annulus A and the leaflets L. In some embodiments, the support 110 can be expanded from the delivery configuration 111 to the expanded configuration 113 by balloon expansion. Alternatively, the support 110 may be configured to self-expand into the expanded configuration 113. In some embodiments, the gap distance 132 between the tip portions 122 and the support 110 can decrease as the support 110 is expanded, either by deformation of the arms 120 to a more inward configuration, or by the radial expansion of the support 110 toward the arms 120, or a combination thereof. In this way, the native leaflets may be compressed or folded between the arms 120 and the outer surface 110S of the support 110 as the support 110 expands from a delivery configuration 111 to an expanded configuration 113. The compression or folding of the arms 120 can engage the leaflets with pressure so as to inhibit downstream movement of apparatus 100 when blood flows in the downstream direction through support 110, e.g. during diastole. In addition, the arms 120 may press the native leaflets against the outer surface 110S to inhibit blood flow around the outside of support 110 during systole.

In some embodiments, the arms 120 are configured to move inwardly toward the surface 110S as the support 110 is expanded so as to more accurately engage the annulus A and/or more firmly engage the leaflets L. Referring back to FIGS. 2C, the arms 120 may have cam portions 126C along elbow portions 126 which can be configured to be engaged by an expandable member (e.g. balloon) on the delivery catheter. The cam portions 126C are configured to deflect a downstream end of the arms 120 (e.g., elbow portion 126 and/or base portion 124) outwardly relative to support 110, causing the arms 120 to pivot about base portion 124 so as to urge tip portions 122 toward the outer surface 110S. This may direct tip portions 122 more securely toward the annulus A, and may enhance compression of the leaflets between the arms 120 and the outer surface 110S of the support 110.

As shown in FIG. 2F, the apparatus 100 may further comprise a valve 150 mounted in the interior lumen of the support 110. The valve 150 may comprise a temporary or permanent valve adapted to block blood flow in the upstream direction and allow blood flow in the downstream direction through the support 110. The valve 150 can have a plurality of leaflets 152, and may be formed of various flexible and impermeable materials including PTFE, Dacron, or biologic tissue such as pericardial tissue or xenograft valve tissue such as porcine heart tissue. Other aspects of valve 150 are described further below. An internal wall within the lumen of the support 110 can be covered at least partially by an impermeable cover 151 to prevent blood flow from inside the support 110 to the outside of the support 110, where it could leak around the exterior of the support 110. In another embodiment the cover 151 may be affixed to an exterior wall of the support 110 and, in either embodiment, may be integrally formed with or attached directly to valve 150. In an additional embodiment, a cover 151 can be applied on at least portions of both the inside wall and outside wall of the support 110.

In some embodiments, the apparatus 100 may comprise a membrane or sealing members 160 extending radially outward from the outer surface 110S of the support 110 to inhibit blood flow between the support 110 and the native leaflets. For example, the sealing members may extend outward from the support 110 so as to extend along the long dimension of the mitral valve into the native commissural regions 170, as shown in FIG. 2F. The sealing members 160 may comprise any of a number of flexible, blood-impermeable biocompatible materials, including one or more of a polymer, thermoplastic polymer, a polyester, a synthetic fiber, a fiber, polyethylene terephthalate (hereinafter "PET"), PTFE or Dacron™. In one embodiment, the sealing members 160 can extend radially outward from the support 110 in a direction extending along a long dimension of the annulus so as to inhibit flow blood flow between the leaflets outside of support 110 when the plurality of arms 120 are coupled to peak portions of the annulus. The sealing members 160 may be configured to pass between the leaflets so as to cover the line of coaptation on the downstream side of the valve (e.g., ventricular side of the mitral valve), thereby inhibiting the flow of blood in the upstream direction (from the ventricle to the atrium in the case of the mitral valve). The sealing members 160 can alternatively be coupled to one or more of the arms 120. For example, the sealing members 160 may be collapsed or wrapped around the tip portions 122 of one or more arms 120 during delivery of the apparatus 100, and the sealing members 160 may open or become unfurled and urged against the lower surface of the leaflets by the pressure and flow of blood when the arms 120 are in position behind the leaflets. In a particular example, the sealing members 160 may be coupled to the outermost arms 120 in each row 128 so as to be positioned near the native commissural regions 170 when the arms 120 are in the outward configuration 123. Thus, when the sealing members 160 are deployed, they can extend over the native commissural regions 170 and can inhibit or prevent the flow of blood through the native commissural regions 170 in either the upstream or down stream directions.

FIGS. 2F1-A and 2F1-B are side and top views, respectively, of a prosthetic heart valve device (e.g., apparatus 100) having sealing members 160 configured to be positioned adjacent the commissures of the native valve. In some embodiments of the apparatus 100 suitable for mitral valve replacement, a pair of sealing members 160A, 160B may be coupled to opposing sides of the support 110, e.g., roughly 90 degrees offset from the locations of rows 128A, 128B of arms 120, and so as to be positionable in the commissures of the native valve. Sealing members 160A, 160B may comprise tent-like conical or pyramidal tubes of a membrane or fabric such as Dacron or PTFE, tapering from an open downstream end 161 to a closed, narrow upstream end 162. The outer surface 110S of the support 110 (or alternatively, an inner surface of the support 110) may be covered with an impermeable fabric to prevent blood flowing from within the sealing members into the interior of the support 110. Wires may be sewn into sleeves along the edges and along the longitudinal peaks of the sealing members 160A, 160B to maintain their shape and conformity. The sealing members 160A, 160B are configured to fit adjacent or within commissures between the posterior and anterior leaflets, to effectively seal the outer surfaces of the sealing members 160A, 160B to the native valve tissue. During systole, blood is pushed under pressure though the open downstream end 161 of the sealing members 160A, 160B thereby inflating the sealing member 160A, 160B and urging it against the native leaflets and enhancing the seal. Optionally, openings (not shown) may be provided between the interior of the sealing members 160A, 160B and the interior of the support 110, allowing blood to flow from within the support 110 into the interior of the sealing members 160A, 160B to further pressurize them.

In addition to the commissures, gaps may be present between the leaflets and support 110 in other areas around the circumference of the support 110 and through which perivalvular leaks may occur. A sealing member 160 or other similar membrane feature can be included to extend around most or the entire circumference of the support 110 so as to seal any such gaps. In one embodiment, shown in FIGS. 2F2-A and 2F2-B, a bell-shaped skirt 163, tapering from an open downstream end 164 to a closed, narrower upstream end 165 can be provided on the apparatus 100. The skirt 163 may be integrally formed with or sewn to a cover 166 (such as cover 151 discussed above with respect to FIG. 2F) over the interior wall of the support 110. In some embodiments, the skirt is baggy, or otherwise provided with extra membrane material, and can be very flexible and conformable so as to conform to the shape of any gaps between the leaflets and the support 110. In some embodiments, the skirt 163 can be configured to be expanded or inflated by blood during systole so as to be urged radially outward to fill in any such gaps. In operation, and during systole, blood is forced through the open downstream end 164 so as to radially expand the skirt 163 into firm and continuous engagement with the leaflets. Openings (not shown) may be provided in the wall of the support 110 and/or in the cover 166 thereby providing fluid communication with an interior of the skirt 163 to allow blood to flow from the interior lumen of the support 110 to the interior of the skirt 163 to further pressurize the skirt. Optionally, the skirt 163 may be tacked or tethered to the support 110 at one or more locations around the perimeter of the support and/or the narrower upstream end 165 of the skirt 163 to limit the radial expansion or eversion of the skirt 163 (e.g. via sutures 167 shown in FIG. 2F2-B). Additionally, wires (not shown) may be sewn in or otherwise coupled to the material of the skirt 163 to keep the downstream end 164 open and/or otherwise maintain the skirt's desirable shape. As a further option, the skirt 163 may include plaits or internal partitions dividing the skirt 163 into a series of vertical tubular sections around the circumference of the support 110.

In alternative embodiments, the skirt 163 may extend only part-way down the length of the support 110 from the upstream end 112*a*, as shown in FIG. 2F3-A. In another arrangement, shown in FIG. 2F3-B, the skirt 163 can be attached to the support 110 at the upstream end 112*a* and configured to flare upwardly in an upstream direction (e.g., have an open skirt end facing upstream). In further embodiments, the skirt 163 may attach to and extend from the downstream end 114*a* of the support 110, flaring and opening either in a downstream direction as shown in FIG. 2F4-A, or flaring and opening in an upstream direction as shown in FIG. 2F4-B. In another embodiment, the skirt 163 may flare in the upstream direction while extending around the outside of arms 120, as shown in FIG. 2F4-C. The skirt 163 may alternatively be mounted to the support 110 in a mid portion, between the upstream and downstream ends 112*a*, 114*a*. In further embodiments, the skirt 163 may also extend around only a subsection of the perimeter of the support 110.

In a further embodiment, shown in FIGS. 2F5A-2F5D, one or more leaflet pushers 300 can be coupled to the support 110 and configured to extend in the upstream direction to engage the leaflets and urge them into coaptation with each other or into sealing engagement with the outer surface 110S of the support 110. The leaflet pushers 300 may be constructed similarly to arms 120 but because they need not serve the function of pushing against or pressing into the annulus to anchor the device 100, leaflet pushers 300 may, in some embodiments, have less rigidity and strength as arms 120. Further, in select embodiments, leaflet pushers 300 can have further lateral extension when compared with arms 120 to enable the pushers 300 to engage the leaflets near the valve commissures, (e.g., where the leaflets are not in engagement with the support 110 and may be prevented from coapting). As shown in FIGS. 2F5A-2F5D and described further below, the leaflet pushers 300 can push in opposing directions so as to urge the leaflets toward each other.

As shown in FIGS. 2F5A-2F5D, leaflet pushers 300 extend from a downstream end 114*a* of support 110. A pair of leaflet pushers 300 can be provided and coupled on each of two opposing sides of the support 110 which can be approximately 90 degrees offset from the two opposing sets of arms 120, such that each pair of leaflet pushers 300 are positioned to extend toward the commissural regions 170 of the valve. In one embodiment, each pair of leaflet pushers 300 can be arranged in a crossing pattern along the outer surface 110S of the support such that the distal tips 302 are on opposite sides from the bases 304 (shown in FIGS. 2F5B and 2F5D). When the support 110 is in the radially-contracted delivery configuration 111, distal tips 302 are separated from each other as shown in FIGS. 2F5A-2F5B. In this configuration, leaflet pushers 300 can be positioned behind the leaflets L such that the distal tips 302 engage the ventricular or downstream side of the leaflets outside of the support 110. When the support 110 is expanded to its expanded configuration 113, distal tips 302 are urged toward one another, pushing the leaflets L toward each other into sealed coaptation, as shown in FIGS. 2F5C-2F5D. Alternatively or additionally, leaflet pushers 300 may be configured to push leaflets L toward the support 110 so as to seal against the outer surface 110S of the support 110.

Figure 2G:
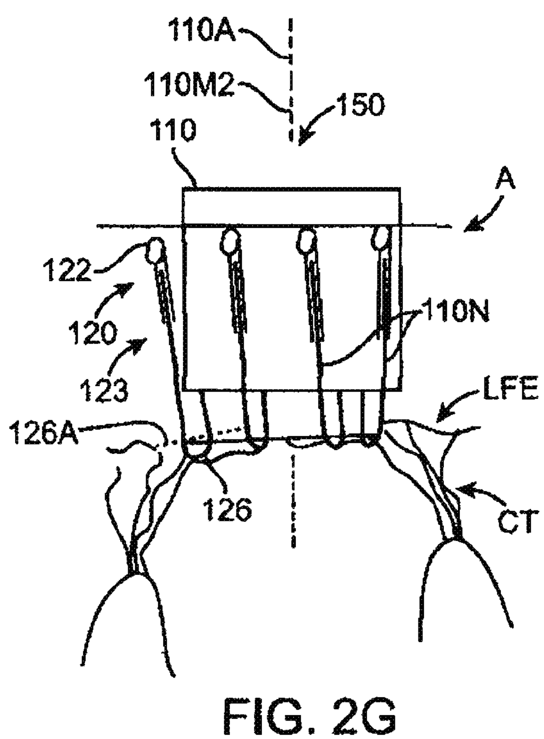
FIG. 2G is a schematic illustration of a side view of a prosthetic heart valve device having a support shown in an extended configuration and a plurality of arms extending between chordae tendineae, in accordance with various embodiments of the present technology.

FIG. 2G is a schematic illustration of a side view of a prosthetic heart valve device (such as apparatus 100) having a support 110 shown in an extended configuration 113 and having a plurality of arms 120 in an outward configuration 123 extending between chordae tendineae CT. In a variety of embodiments, the locations and geometry of the plurality of arms 120 are configured so the arms 120 pass unobstructed between the chordae tendineae CT. For mitral valve replacement, the plurality of arms 120 can be arranged to pass more easily behind the anterior and posterior leaflets. In many embodiments, the tip portions 122 of the arms 120 extend in the outward configuration 123 along two rows (previously described as rows 128A and 128B). The plurality of tip portions 122 in each row can be spaced at a distance within a range from about 2 mm to about 7 mm away from the outer surface 110S when the support 110 is in the delivery configuration 111. These tip portions 122 could then be passed relatively easily behind the anterior and posterior leaflets near a middle portion of the native leaflet, where there are relatively few chordae. The tip portions 122 can be relatively closer to the outer surface 110S and the bend radius of the curved elbow portion 126 about axis 126A near the bottom of the arm 120 can be smaller for the arms 120 near the second midline 110M2 of the support 110 than for the arms 120 further away from the second midline 110M2. Prior to expansion of the support 110 from the delivery configuration 111 to the expanded configuration 113, the arms 120 may hold or engage the central portions of the anterior and posterior leaflets together against the outer surface 110S of the support 110. In some embodiments, this gentle temporary constraint of the leaflets may inhibit pressure gradients and/or regurgitation during the implantation procedure.

For mitral valve treatment, during expansion of the support 110 into the expanded configuration 113, one row of the arms 120 can be configured for placement behind the anterior leaflet and to contact the annulus without extending excessively or obstructively into the left ventricular outflow tract. The other row of arms 120 can be configured for positioning behind the posterior leaflet and may contact regions of the ventricular wall, while engaging the posterior annulus with the tip portions 122. The more laterally positioned arms 120—those further away from the midline 110M2 in each row—may remain some millimeters away from the outer surface 110S of the support 110 when the support has been expanded, so that the tip portions 122 can make contact with the annulus even though the expanded support 110 does not fill the entire area of the native mitral valve near the commissures 170. These more laterally positioned arms 120 may also engage the leaflets and urge them against the support 110 and in closer apposition to each other to help prevent retrograde blood flow through the commissures 170.

In some arrangements, this approach may tend to push some or all of the central chordae CT laterally. Accordingly it may be desirable in some embodiments to make the arms 120 a little longer, so that the arms 120 extend in the downstream direction further into the left ventricle (e.g., increase the distance 138 shown in FIG. 2A1) and so that the chordae CT and leaflets are more minimally displaced. The leaflets can be compressed by the arms 120 an amount sufficient so as to provide support, keep the leaflets out of the way of the prosthetic valve 100, and to limit systolic anterior motion.

Referring again to FIG. 2A1, the skeleton 140 of the support 110 may comprise a plurality of nodes 110N which move apart from one another when the skeleton 140 is expanded. The base portions 124 of the arms 120 can be coupled to the plurality of nodes 110N such that the plurality of arms 120 separate from one another when the support 110 expands from the delivery configuration 111 to the expanded configuration 113. The plurality of bases 124 can be coupled to the plurality of nodes 110N, for example, such that the plurality of base portions 124 separates with respect to each other when the support 110 expands. The arms 120 and tip portions 122 may also splay outwardly—i.e. the splay angle 127SA of the arms 120 relative to the longitudinal axis 110A may increase—when the support 110 expands from the delivery configuration 111 to the expanded configuration 113. Each of the plurality of base portions 124 may be integrally formed with the nodes 110N or can be connected to the plurality of nodes 110N in other ways, for example, by welding, bonding, mechanical fastener, slider, tube, and many attachment and other coupling mechanisms known in the art so as to transmit forces from the tip portions 122 to the skeleton 140 of the support 110.

In some configurations, due to their angle relative to the support 110, arms 120 may translate forces downward and radially inward against the support 110 at the location (e.g., base portion 124) where the arms 120 are coupled to the support 110. This force may be at a maximum force when a valve (e.g., valve 150) mounted to the support 110 closes and the force of blood pressure downstream of the valve 150 pushes the support 110 in the upstream direction and arms 120 engage the annulus. Accordingly, the support 110 may have a hoop strength sufficient to resist inward radial deformation at the point where the arms 120 are coupled to the support 110.

In one embodiment, the support 110 may include a retention structure to inhibit migration of apparatus 100 in the downstream direction. In embodiments suitable for mitral valve replacement, the retention structure may be coupled to support 110 on or near its upstream end 112*a* so as to be located in the left atrium and upstream of the native annulus. FIG. 2H-1 is an isometric side view of a prosthetic heart valve device (such as apparatus 100) having a flange 165 extending outwardly from the support 110 at a proximal, upstream end 112*a*, in accordance with another embodiment of the present disclosure. The flange 165 can be coupled to the support 110 and externally oriented so as to extend laterally from the upstream portion 112 of the support 110 and have a circumference greater than the circumference of the support 110. The positioning of the flange 165 can be upstream of the annulus to inhibit migration of the apparatus 100 downstream through the native annulus during contraction of the upstream or first heart chamber. The flange 165 may be integrally formed with the support 110 or a separate component coupled to the support 110, and can be made of the same or different material as the support 110, e.g. a balloon-expandable malleable material such as stainless steel, or a self-expanding material such as nitinol. In some embodiments, the flange 165 may comprise an integral part of the skeleton 140 of the support 110. In alternative embodiments, the flange 165 can be attached to the support 110 in a variety of ways such as by sutures, clips, or other fasteners known in the art. The flange 165 can have an outer diameter which is about 2-20 mm larger than the outer diameter of the support 110 so to extend outwardly and over the native annulus within the first heart chamber. The flange 165 can include a cover (not shown) such as polyester, expanded PTFE, or other material to encourage tissue ingrowth. The flange 165 can be spaced apart from the tip portions 122 of arms 120 in the upstream direction at a distance large enough to position the annulus between the tip portions 122 and the flange 165, and in some embodiments, to compress the annulus between the tip portions 122 and the flange 165 to hold the apparatus 100 in position relative to the native valve. Accordingly, in some embodiments, the flange 165 can be configured to extend from the upstream portion 112 of the support 110 and engage a supra-annular surface while the arms 120 extend from the downstream portion 114 of the support and extend outwardly in an upstream direction to engage a subannular surface, thereby securing the apparatus 100 to the native valve region.

In another embodiment, as shown in FIG. 2H-2, a plurality of elongated fingers 165PF may extend radially outward from the upstream end 112*a* of the support 110. The fingers 165 PF may be configured to be deflectable into a straightened configuration for delivery within the lumen of a catheter, and to have sufficient resiliency to return to the radially extended configuration when released from the catheter. In some embodiments, the fingers 165 PF may be coupled to or comprise extensions of the arms 120. For example, as shown in FIG. 2H-2, rather than terminating at the point of attachment to support 110, arms 120 may extend upwardly from curved elbow portions 126 in an upstream direction along the outer surface 110S of the support 110 to the upstream end 112*a*, and may then be bent outwardly so as to extend radially away from the support 110 a distance sufficient to provide retention for the apparatus 100 within the upstream or first heart chamber.

The embodiments described herein can also be adapted for trans-apical delivery via ventricular incision or puncture, or retrograde delivery via the aorta. In trans-apical and aortic delivery, due to the approach coming from the downstream side of the valve rather than the upstream side, the upstream portion 112 and the downstream portion 114 of the apparatus will be reversed on the delivery system, and the delivery system can be modified appropriately.

FIG. 2I shows a prosthetic treatment apparatus 100 adapted to treat the aortic valve AV in accordance with other embodiments of the present technology. The shape, size, stiffness, and other aspects of support 110 and arms 120 can be adapted as needed for the aortic valve. For aortic valves, it may be preferable to group the tips 122 of the arms 120 into three groups in the outward configuration 123 so as to correspond to the tricuspid native aortic valve, or, in other embodiments, in two groups when bicuspid aortic valves are treated. Alternatively, the plurality of arms 120 may be evenly spaced about the circumference of the support 110. When placed in the aortic valve AV, in addition to anchoring the apparatus 100 in position by engagement with the annulus, the arms 120 may help to ensure that the valve is placed at the right longitudinal location in the aorta, for example, as far upstream as possible to avoid blockage of the coronary ostia. Any of the embodiments described herein or particular features thereof may be utilized in embodiments configured for aortic valve treatment.

Because the apparatus 100 utilizes the plurality of arms 120 to engage the annulus for maintaining the position of the apparatus 100 rather than outward compression against the aortic wall, the support 110 can be expanded to a diameter slightly smaller than the inner diameter of the aorta. This slightly undersized expanded configuration 113 may protect against unintentional blockage of the coronary ostia. Further, the present technology may provide more consistent and complete deployment of the apparatus 100 than prior transcatheter aortic valves that rely on aggressive expansion against the aortic wall and/or annulus. Prior transcatheter aortic valves may deploy to a non-circular, uneven shape because of calcium nodules in the native valve leaflets. In contrast, the apparatus 100 of the present technology can be deployed consistently into a known shape and size in which it will reliably function. This improved coupling to the annulus can help to prevent perivalvular leakage as well as incompetent valve closure due to incomplete valve expansion. Further, the plurality of arms 120 can hold the native aortic leaflets against the support 110, helping to decrease perivalvular leakage and regurgitation. The improved coupling to the annulus with the arms 120 and the support 110, as described herein, may also reduce the incidence of embolic debris and stroke, which can be a particular concern with transcatheter aortic valve replacement.

FIG. 2J is a top view of a prosthetic heart valve device (such as apparatus 100) having a plurality of sealing members 160 configured to extend toward tricuspid valve commissures of the native aortic valve as opposed to the bicuspid valve commissures of a native mitral valve. The sealing members 160 are positioned around the support 110 (shown in the expanded configuration 113) and configured to extend into, over, or under tricuspid (e.g. aortic) valve commissures, so as to reduce the risk of regurgitation or perivalvular leaks. In the illustrated embodiment, the sealing members 160 may include three separate portions angularly offset by about 120 degrees to as to extend into each of the three aortic commissures. In other embodiments, the sealing members 160 may have a triangular configuration, so that the corners of the triangles extend towards the native tricuspid valve commissures.

Devices suitable for aortic deployment may further include a flange 165 or plurality of fingers 165PF on the upstream end 112*a* of the support 110 (similar to those shown in FIGS. 2H-1 and 2H-2) that may be positioned on the ventricular side of the aortic annulus to help inhibit or prevent downstream movement of the apparatus 100.

Additionally, devices suitable for aortic valve replacement may be implanted using either a retrograde approach via the aorta, a trans-septal approach from the right atrium, or transapical approach via a puncture or incision in the left ventricle. In retrograde approaches, because the native valve will be approached from the downstream side rather than the upstream side, the apparatus 100 will be oriented in a reverse direction on the delivery system from the trans-septal mitral embodiments described above. Further, the delivery system can be modified appropriately for this reverse orientation. In apical approaches, the device will be oriented similarly to trans-septal mitral embodiments, although because of the shorter length and surgical approach, other suitable modifications may be made to the delivery system.

Figure 3B:
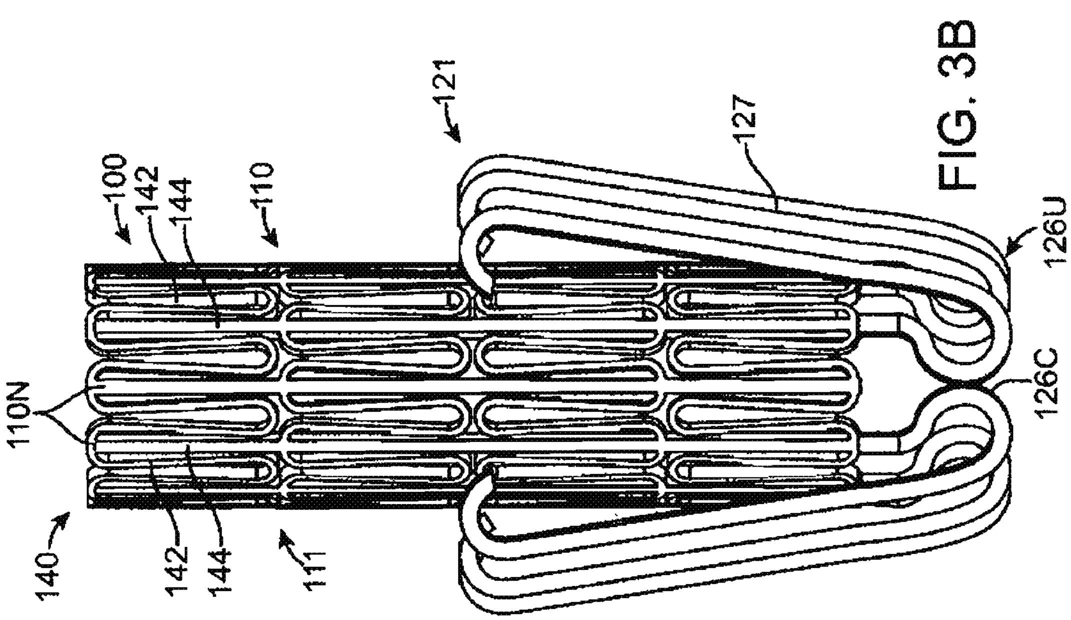
Figure 3A:
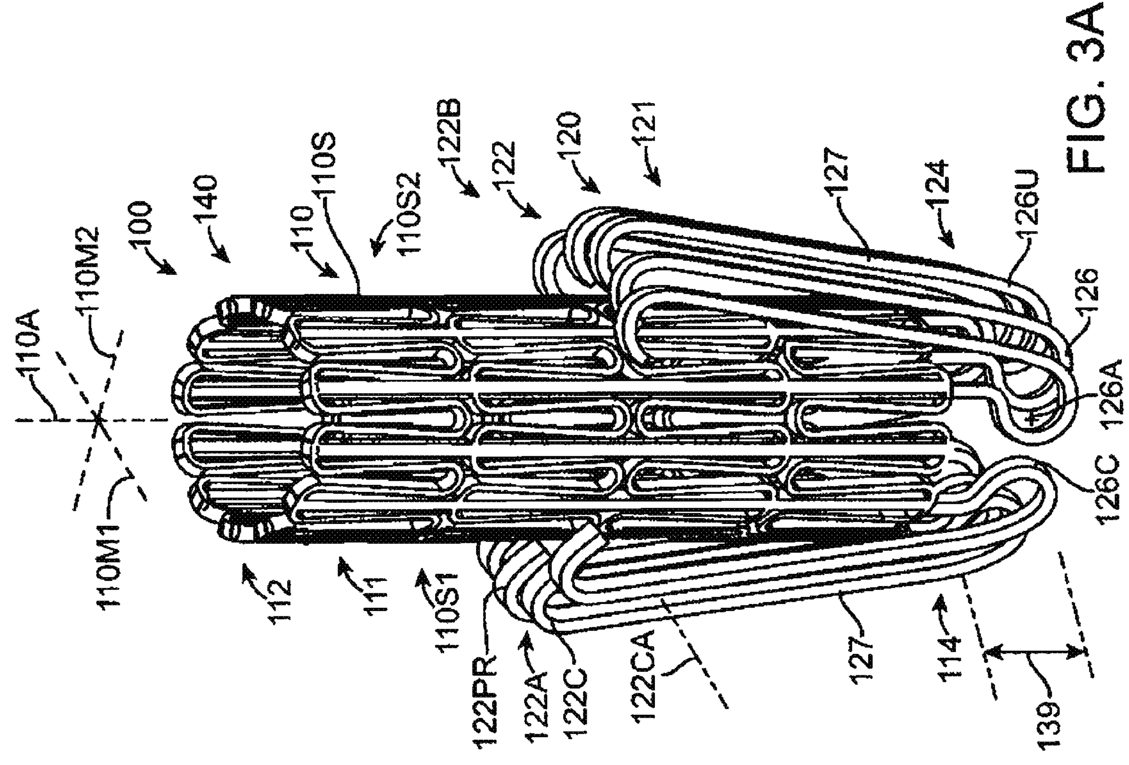
Figures 3C, 3D:
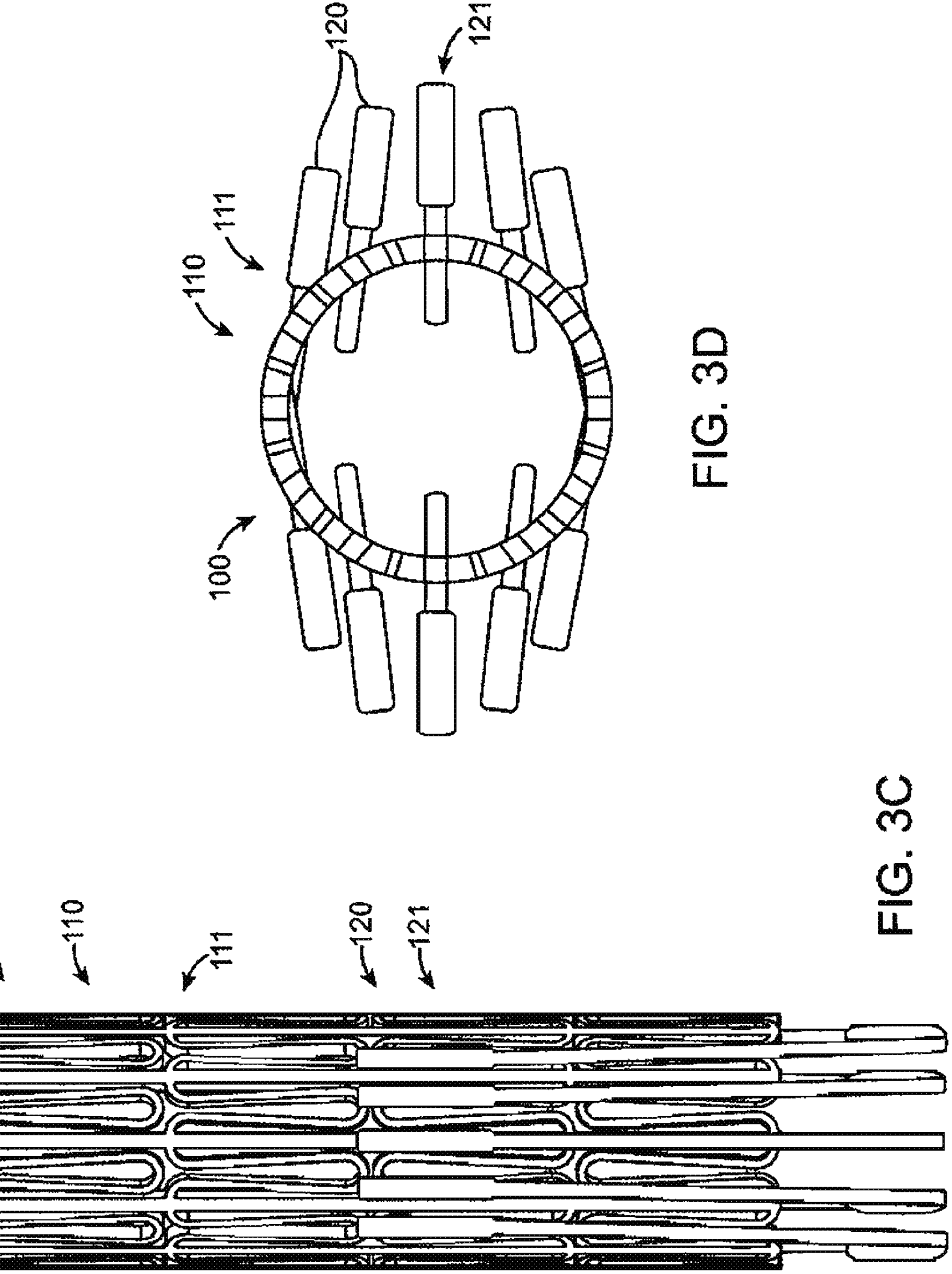

FIG. 3A is an isometric view of a prosthetic heart valve device having an expandable support 110 shown in a delivery configuration 111 and having a plurality of arms 120 shown in an inward configuration 121 such that the device is suitable to access a valve of the body percutaneously. FIGS. 3B, 3C and 3D show front, side, and top views, respectively, of the expandable support 110 and plurality of arms 120 configured as in FIG. 3A. Each of the plurality of arms 120 can deflect laterally in response to tissue contact. In some embodiments, the height 138 of the tip portions 122 and/or the length of arms 120 can vary in response to tissue contact with the annulus. Many of the structures are similar to the embodiments of FIGS. 2A-2J and identical numbers and letters may indicate similar elements.

Referring to FIGS. 3A-3D together, the skeleton 140 comprises a strut pattern geometry. The plurality of struts 142 extends between a plurality of elongate posts 144. The plurality of struts 142 can extend between the posts 144 in a sinusoidal configuration which can be collapsed so as to decrease the separation distance between the ends of each strut 142 and to decrease the separation distance between each of the posts 144 when the support 110 is radially contracted in the delivery configuration 111. The posts 144 may comprise substantially rigid structures and can extend substantially parallel to the longitudinal axis 110A so as to transfer the load of the valve 150 to the plurality of arms 120. The plurality of struts 142 can be attached to the plurality of posts 144 so as to define the plurality of nodes 110N.

With expansion of the support 110 from the delivery configuration 111 to the expanded configuration 113, the struts 142 can assume an elongate configuration so as to increase the separation distance of the posts 144 and corresponding nodes 110N. The distance between the ends of the struts 142 can be increased with deformation of the struts 142 with force of a balloon (not shown), or the struts 142 may comprise a shape memory material, for example. The skeleton 140 may also comprise a variety of eyelets, hooks, or other features to facilitate attachment of the valve, membrane, sealing member, skirt, cover, or other elements.

The plurality of tips 122 can be curved such that each tip comprises a curved portion 122C. The curved portion 122C of each of the plurality of tips 122 can be curved around an axis 122CA. The curved portion 122C can extend from the extension portion 127 pointing inwardly toward the surface 110S of the support 110, and the axis 122CA of each curved portion may be parallel to a tangent of the outer surface of support 110, or, alternatively, parallel to the midline 110M1, for example. In the embodiment shown, the axis 122CA of each curved portion 122C are generally parallel to each other and parallel to midline 110M1.

The plurality of arms 120 are attached to the downstream ends of posts 144 and have a curved elbow portion 126 extending a distance 139 below the downstream end portion 114 of the support 110. Each curved elbow portion 126 can be curved about an axis 126A which, like axis 122CA, is parallel to midline 110M1. Alternatively, axis 126A may be parallel to a tangent of the outer surface of support 110, or disposed at some other angle. Intermediate elbow portions 126 may comprise a cam portion 126C to engage the balloon (not shown). The curved elbow portion 126 may comprise U-shaped portion 126U. The curved elbow portion 126 can extend to the extension portion 127, and the extension portion 127 can extend from the curve elbow portion 126 to the tip portion 122.

Figures 3E, 3F:
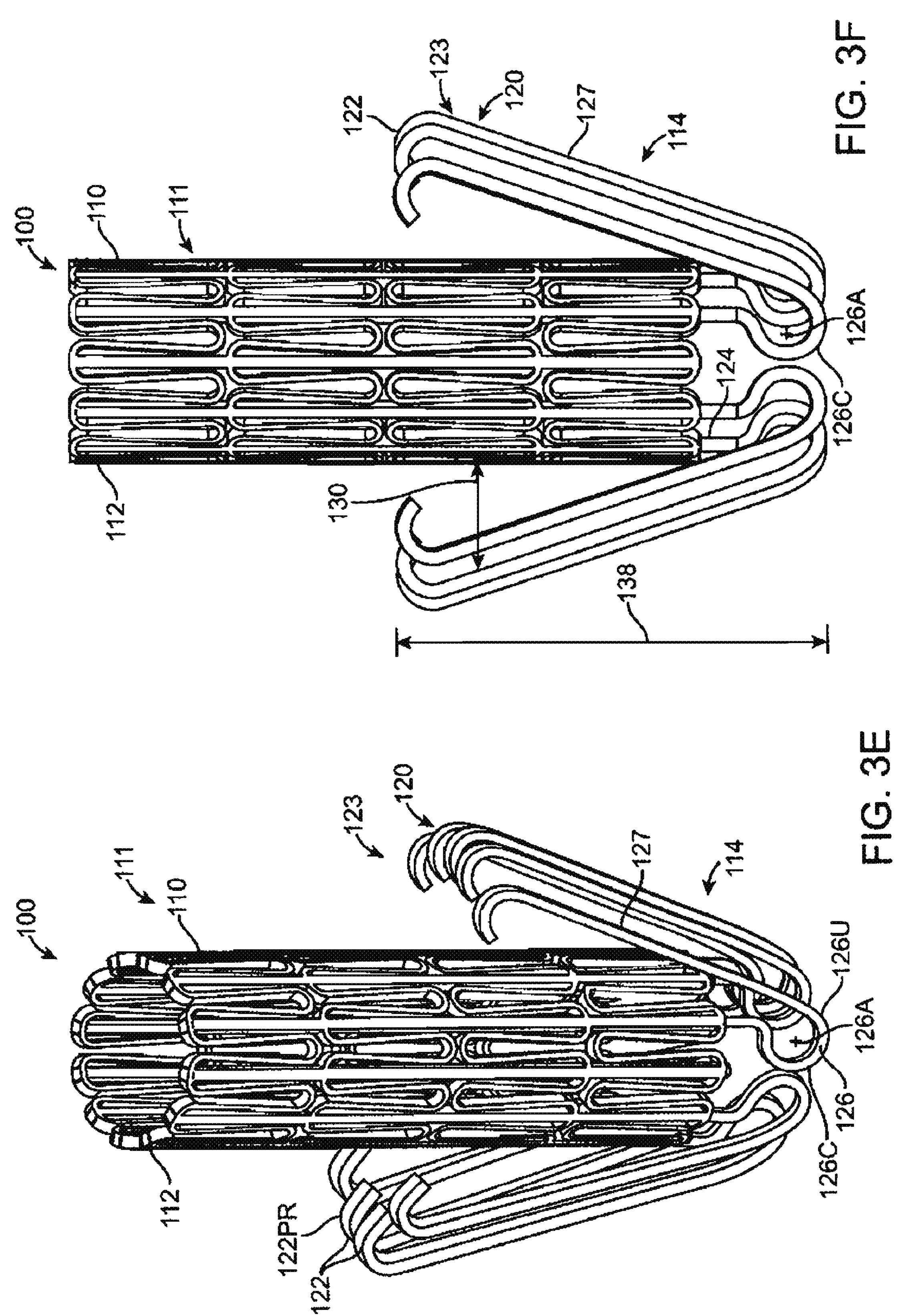
FIG. 3E is an isometric view of a prosthetic heart valve device having an expandable support shown in the delivery configuration and a plurality of arms shown in an outward configuration such that the arms are positioned to receive leaflets of a native valve between the arms and the expandable support, and configured in accordance with a further embodiment of the present technology.
FIGS. 3F, 3G and 3H show front, side, and top views, respectively, of the device having the expandable support and plurality of arms configured as in FIG. 3E.
Figures 3G, 3H:
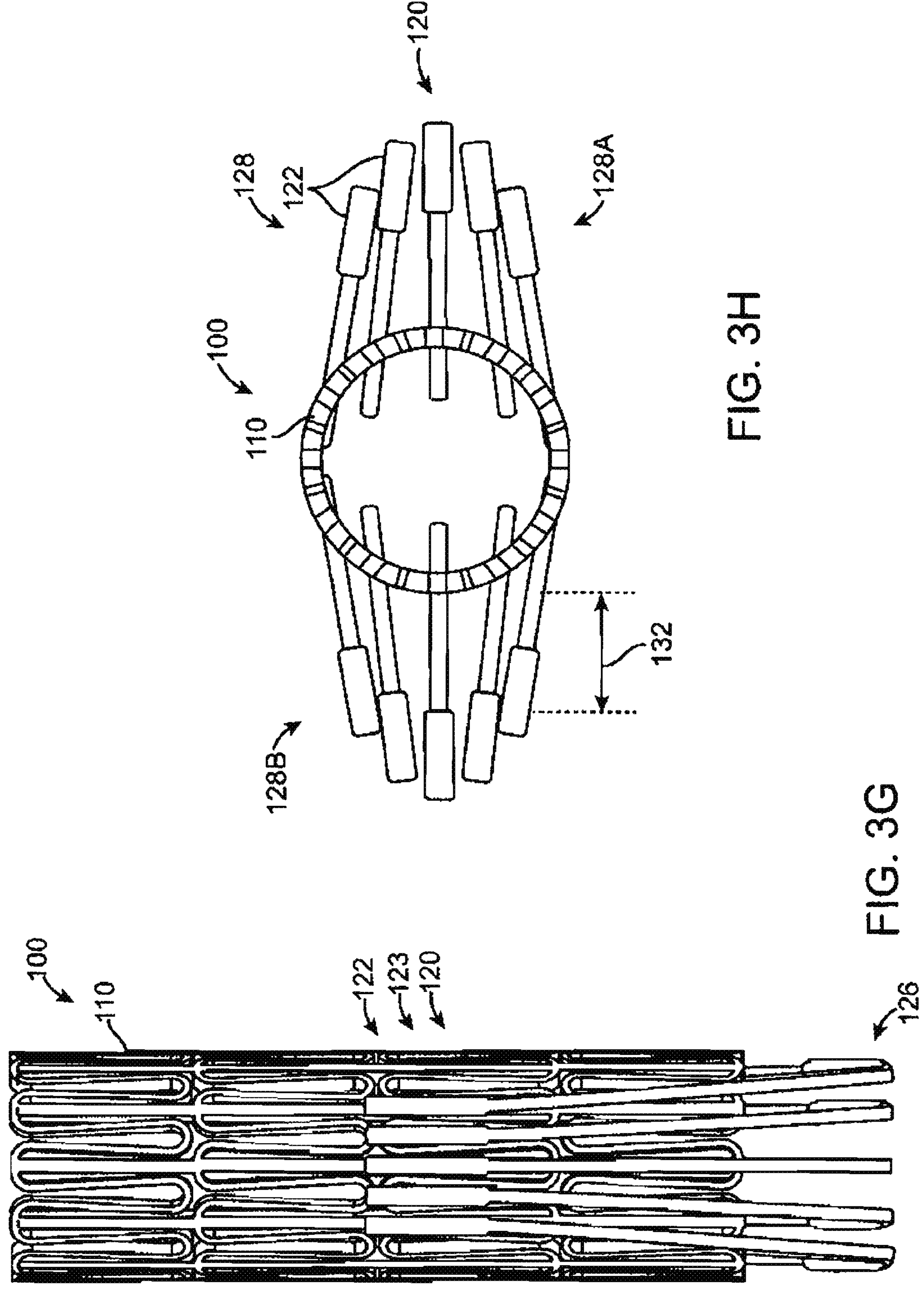

FIG. 3E is an isometric view of a prosthetic heart valve device (such as apparatus 100) having an expandable support 110 shown in the delivery configuration 111 and a plurality of arms shown in an outward configuration 123 such that the arms 120 are positioned to receive leaflets of a native valve between the arms 120 and the expandable support 110. FIGS. 3F, 3G and 3H show front, side, and top views, respectively, of the expandable support 110 and plurality of arms 120 configured as in FIG. 3E.

Figures 3I, 3J:
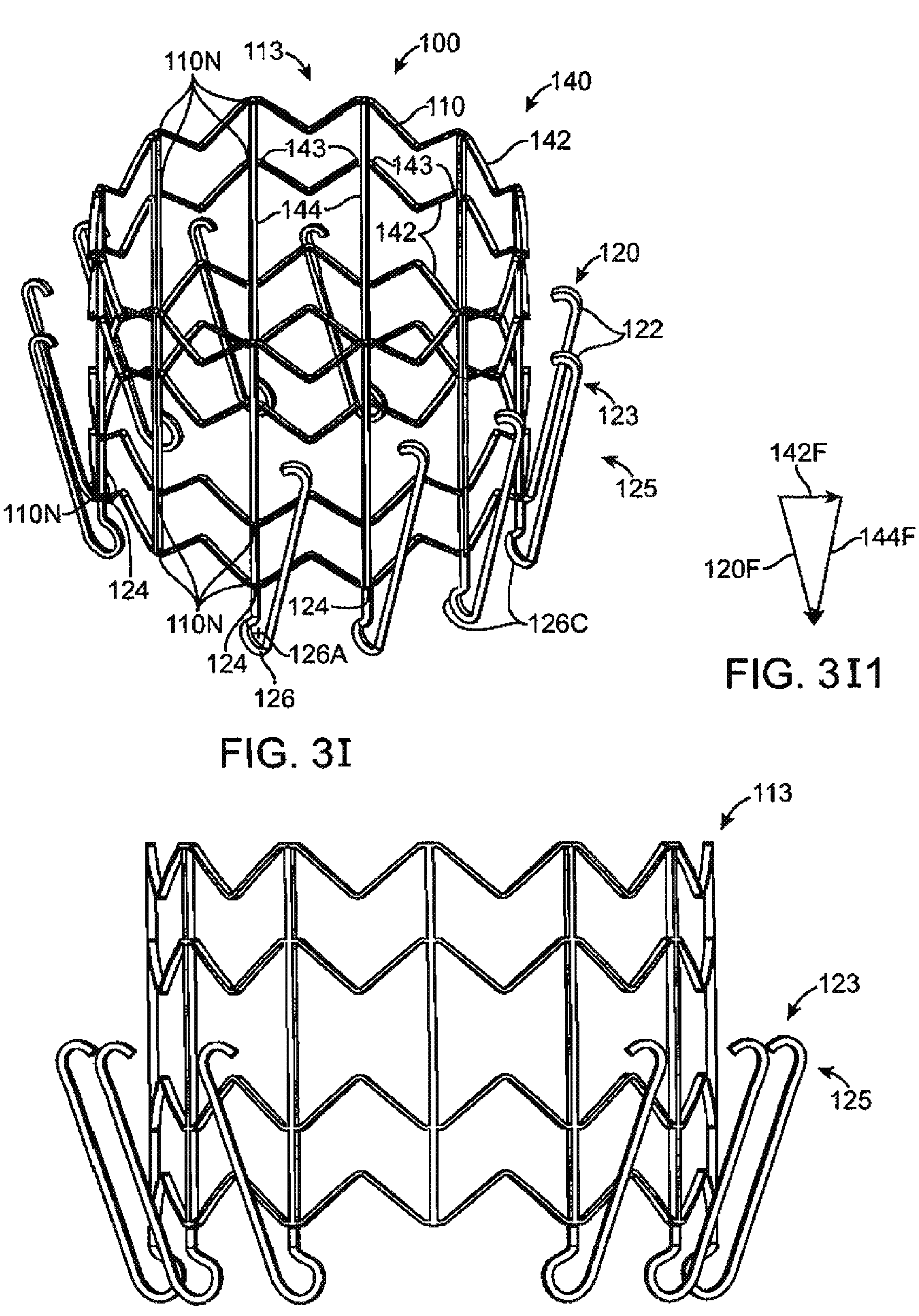
FIG. 3I is an isometric view of a prosthetic heart valve device having an expandable support shown in an expanded configuration and a plurality of arms shown in the outward configuration such that the device is suitable to couple to the annulus of a native valve, configured in accordance with additional embodiments of the present technology.
FIGS. 3J, 3K and 3L show front, side, and top views, respectively, of the device having the expandable support and plurality of arms configured as in FIG. 3I.
Figure 3K:
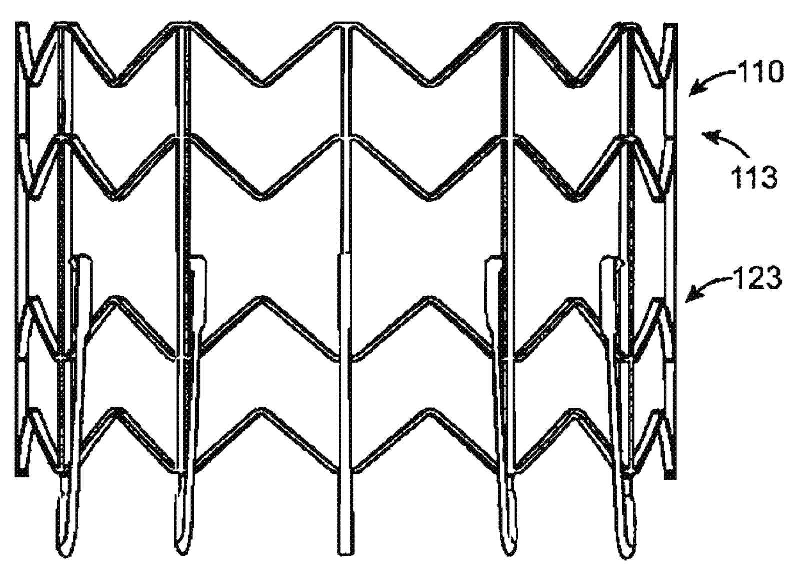
Figure 3L:
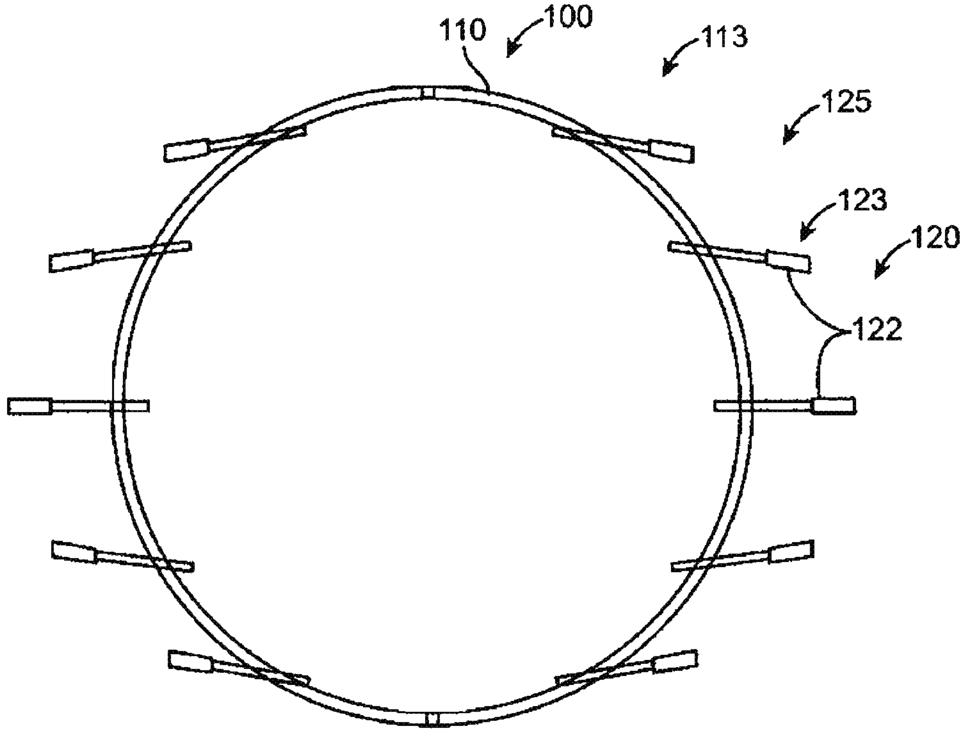

FIG. 3I is an isometric view of a prosthetic heart valve device (such as apparatus 100) having an expandable support 110 shown in an expanded configuration 113 and a plurality of arms 120 shown in the outward configuration 123 such that the device is suitable to couple to the annulus of a native valve. FIGS. 3J, 3K and 3L show front, side, and top views, respectively, of the expandable support 110 and plurality of arms 120 configured as in FIG. 3I. The plurality of struts 142 comprises an elongate configuration to increase the separation distance among posts 144, and the ends 143 of the struts 142 are spaced farther apart from each other. The nodes 110N between posts 144 are spaced farther apart from each other and correspond to the increased separation distance between posts 144. The posts 144 comprise sufficient rigidity to transfer the load of the valve 150 to the plurality of arms 120. The struts 142 extending between the posts 144 comprise sufficient strength to support the load forces of the arms 120.

FIG. 3II is a force diagram illustrating the forces exerted on the arms during systole and showing the corresponding forces to the support's struts 142 and posts 144. In some embodiments, when engaging the annulus, the arms 120 are oriented so as to be generally orthogonal to, or at an oblique angles between about 45 and 135 degrees relative to, the subannular surface, such that the loading exerted upon the arms 120 is primarily a compressive, axial load. Assuming for simplicity that the force through each arm 120 is entirely axial, due to the angle of the arm 120 relative to the support 110, the force 120F exerted on each arm 120 results in a radially inward force 142F to the support 110 and an axial force 144F to the support 110. Each of the posts 144 attached to the arm 120 comprises sufficient strength to support the arm 120 in response to axial force 144F, and the struts 142 coupled to each post 144 near the downstream end 114*a* comprise sufficient strength to resist deformation between the ends 143 and support the arm 120 in response to the radial force 142F.

Figure 4A:
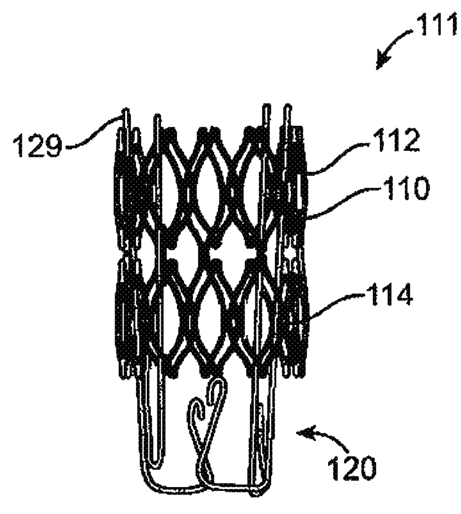
Figure 4B:
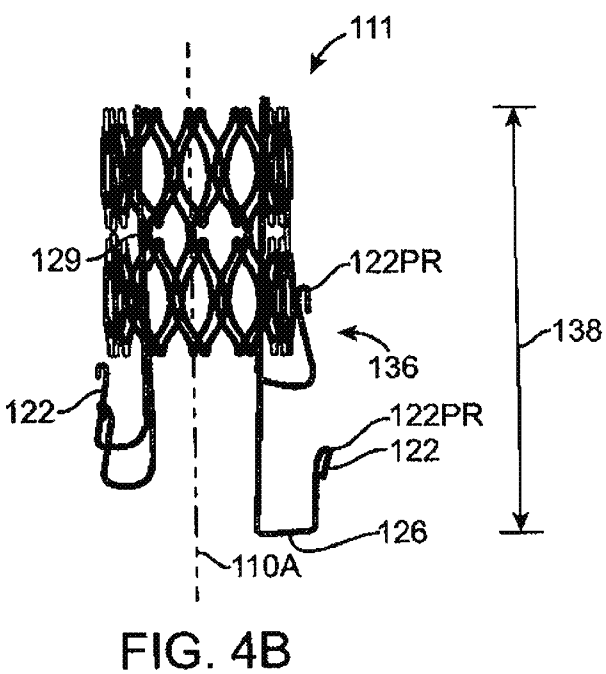

FIGS. 4A and 4B are side views of prosthetic heart valve devices (apparatus 100) having a plurality of arms 120 shown in a first inward configuration 121 (FIG. 4A) and an outward configuration 123 (FIG. 4B). In one embodiment, apparatus 100 comprises a self-expanding support 110 composed of a resilient material configured to self-expand from the delivery configuration shown in FIG. 4A to the expanded configuration shown in FIG. 4B. The material may include a variety of different metals or polymers, but in some embodiments, includes a super-elastic material such as Nitinol. A plurality of arms 120 are coupled to the support 110 and have an inward configuration 121 and an outward configuration 123. The arms 120 may be slidably coupled to the support 110 such that the height 138 of each of the plurality of tip portion 122 along the axis 110A can vary relative to the support 110 and relative to each other tip portion 122. In some embodiments, the arms 120 may comprise an upper portion 129 that extends along the support 110 to vary the height of the arm 120 relative to the support 110. The upper portion 129 may be woven through the openings in the outer surface 110S of the support 110, or may extend through a slidable coupling such as a tube (not shown) mounted to the support 110, for example. The tip portion 122 of each of the plurality of arms 120 may include a pressure reducing tip portion 122PR, having for example a curve or loop to inhibit tissue penetration. The self-expanding support 110 may or may not have struts (not shown) to facilitate attachment of a replacement valve structure.

Operatively, when the pressure reducing tip portions 122PR engage annulus tissue, the arms 120 can slide axially in the downstream direction relative to support 110 to accommodate the varying elevations of the annulus and to ensure that all of the arms 120 contact the annulus. The pressure reducing tip portions 122PR of the arms 120 may also be configured to deflect when contacting annulus tissue to avoid trauma and to allow further variation of the height of the pressure reducing tip portions 122PR. Preferably arms 120 are slidably coupled to the support 110 in such a way that their axial position is maintained once the support 110 is positioned in the desired final location. For example, the coupling mechanism may apply significant friction to the arms 120 such that a fairly high threshold axial force must be applied to the arms 120 to overcome such friction. For example, the threshold force could be of sufficient magnitude that the user could apply it via the delivery system, but could be higher than the forces applied to the arms 120 once implanted. Alternatively, the arms 120 may have teeth, bumps, notches, detents, or other mechanical indexing features that engage a cooperating structure coupled to the support, providing a series of axial positions at which the arm 120 can be maintained.

FIGS. 5A1-5A4 are side views of a prosthetic heart valve (such as apparatus 100) having arms 120 with ringed tips 122 configured in accordance with another embodiment of the present technology. The apparatus 100 is shown having a plurality of arms 120 with pressure reducing tip portions 122PR comprising rings or loops wherein each ring 122 can lie in a vertical plane extending radially from the central longitudinal axis 110A of the support 110, or which is parallel to a tangent of the outer surface 110S of the support 110. In such an arrangement, the tangential orientation of the ring 122 may improve the ease of compressing the arms 120 to form a compact delivery profile. In other embodiments, the ring 122 can be at various other angles relative to the support 110. The support 110 in the delivery configuration 111 may comprise a cross-sectional diameter 111D defined by a first outer boundary 111B1 and a second outer boundary 111B2. The curved portion 126 of the arms 120 may have one or more bends 126B1, 126B2, 126B3 so as to offset the axis 126A (FIG. 5A4) to within the outer boundaries 111B1 and 111B2 of the profile of the support 110.

FIGS. 5A5-5A6A show a further embodiment of a prosthetic heart valve device (apparatus 100), having arms 120 with a first, flattened cross-sectional dimension and a second, elongated cross-sectional dimension such that the arms 120 have a relative resistance to bending in different directions. FIG. 5A6B shows a portion of the arm 120 along line A-A of FIG. 5A5. For example, curved portions 126 of the arms 120 can have a cross-sectional shape 126CSA, as shown in FIG. 5A6A. The cross-sectional shape 126CSA is flattened and wider along a distance 126CSC in the circumferential direction (parallel to a tangent of the outer surface 110S of support 110) and relatively thin along a distance 126CSR in the radial direction. Accordingly, the cross-sectional distance 26CSC extending circumferentially and parallel to the support 110 is greater than the cross-sectional distance 126CSR extending radially. This arrangement can give the arms 120 a lower bending stiffness toward and away from the support 110, but a relatively high bending stiffness in a circumferential direction. Various other cross-sectional dimensions and geometries may be selected to provide a desirable relative bending stiffness in any direction.

FIG. 5A6B shows a portion of the arm along line B-B of FIG. 5A5. As illustrated, the extension portion 127 of each arm 120 can have a different cross-sectional shape than the curved elbow portion 126 of the arm 120 (FIG. 5A6A). For example, while the cross sectional shape 127CSA is flattened and wider along a distance 127CSC in the circumferential direction (parallel to a tangent of the outer surface 110S of support 110) and relatively thin along a distance 127CSR in the radial direction (similar to the cross-sectional shape 126CSA), the radial dimension along distance 127CSR can be larger than the radial dimension along distance 126CSR in the curved elbow portion 126 in order to resist buckling of the extension portions 1127. The flattened and wider dimension 27CSC can provide a wider surface for engagement of the native leaflets.

In other embodiments, the curved elbow portion 126 may have a radial dimension 126CSR that is the same or greater than that of the extension portion 127 so as to have greater resistance to bending. Further, either the curved elbow portion 126 or the extension portion 127 may have a cross-section in which the circumferential dimension is closer to or about the same as the radial dimension, giving it more rigidity and resistance to bending away from the support 110. In one embodiment, the curved elbow portion 126 may have a cross-sectional shape 126CSA which is circular, while the extension portion 127 has a cross-sectional shape 127CSC that has polygonal geometry, e.g. rectangular, trapezoidal, triangular or other shape.

FIGS. 5A7-5A8 are side and front views, respectively, of prosthetic heart valve devices (apparatus 100) with arms 120 including arm tips having a pressure reducing bent tip portion 122 PR for providing a planar subannular interfacing tip. As shown, arm tips portions 122 have an approximately 90° bend 122C1 about a horizontal axis so that the loops of the pressure reducing tip portions 122PR lie in a plane generally parallel to the subannular plane of the native valve. In some embodiments, the pressure reducing tip portions 122PR may be bent outwardly away from the support 110 as shown in FIG. 5A7, inwardly toward the support 110 as shown in FIG. 5A8, or laterally in a circumferential direction (not shown).

FIGS. 5A9-5A10 are partial side views of a prosthetic heart valve device (apparatus 100) having an arm 120 with loop 510 and two support attachment points on a support 110. As shown, the arms 120 can comprise a loop 510 such as a wire loop with both ends of loop 510 coupled to support 110 to provide a pressure reducing tip 122PR at a distal end of the loop 510. The distal looped end of the loop 510 may be formed in various configurations, with the loop lying in a vertical plane as shown in FIG. 5A9, in a horizontal plane, or in various other configurations. A plurality of such loops 510 may be coupled to the support 110 in various arrangements as described elsewhere herein. In some embodiments and as shown in FIG. 5A10, in order to reduce a cross-sectional profile during delivery, wire loops 510 may be configured to wrap helically around of the exterior of the support skeleton 140 in an inward configuration 121 of the arm 120.

As described above, the support 110 and arms 120 can be covered partially or entirely with a coating or covering which promotes tissue in-growth and provides additional sealing within and around the device. In some embodiments, the arms 110 and the support 110 can be covered by or contained within a fabric cover of Dacron™, ePTFE, or other suitable material. Various arrangements of suitable covers are illustrated in FIGS. 5A11-5A15. In some embodiments, more than one arm 120 (e.g., a plurality of arms 120) may be contained together within a single cover member as described below. For example, in the embodiment shown in FIG. 5A11, a first plurality of arms 120 on a first side 110S1 of the support 110 can be contained within a first cover member 320, while a second plurality of arms 120 on a second side 110S2 of the support 110 can be contained within a second cover member 322. Cover members 320, 322 may comprise a single sheet or wall of material extending across and adhered to one surface of the arms 120, or they may be sewn or otherwise made into a hollow sock or mitten which fits over the arms 120 and completely surrounds them. Cover members 320, 322 may be integrally formed with or attached to a tubular cover or sleeve 324 which extends around the exterior and/or interior of support 110. Cover members 320, 322 may each contain all of the arms 120 on the respective sides of support 110, or only a selected portion of the arms 120.

In another embodiment, shown in FIG. 5A12, two or more arms 120 can each be covered by a separate cover member 326, however, the cover members 326 are interconnected at the distal ends of arms 120 by an interconnecting portion 328. The cover members 326 may form a continuous tubular member extending over the two or more arms 120, or, in another embodiment, separate tubular members 326 may cover each arm 120 and an interconnecting piece may be attached to the distal end of each tubular member. In some embodiments, the interconnection of two or more arms 120 by the cover member 326 and portion 328 may distribute forces more broadly across the valve annulus as well as reducing trauma to the annulus tissue.

In yet another embodiment, shown in FIG. 5A13, each arm can be covered by a separate tubular cover member 330. As described with respect to FIG. 5A11, each cover member 330 may be integrally formed with or coupled to a tubular sleeve 332 configured to cover the support 110. A distal cap 334 of each cover member 330 may conform to the shape of the underlying arm 120 and tip portion 122. Alternatively, the distal cap 334 may have a configuration which distributes force, reduces pressure, and/or reduces the trauma exerted by engagement of the arm 120 on the annulus. For example, as shown in FIG. 5A14, the distal cap 334 may comprise a generally spherical projection 336 substantially larger than the area of tip portion 122. Projection 336 may be soft and padded so as to minimize trauma to the annulus tissue, and made of a material which enhances friction against the annulus to minimize movement of the arm 120 against the tissue. Further, each cover member 330 may be movable longitudinally relative to the underlying arm 120 to allow for self-adjustment of position of the projection 336, thus accommodating for varying elevation of the valve annulus. For example projection 336 may have an inner pocket 339 for receiving the arm 120 and/or tip portion 122 which, prior to deployment of the device, extends toward a distal tip 338 further than does arm 120, leaving some vacant room distally of the tip portion 122. When projection 336 is brought into engagement with the annulus, it may be pushed downward relative to the arm 120 due to the flexibility and compressibility of the cover member 330 and/or projection 336, thereby acting as a shock absorber and ensuring engagement of each distal tip 338 with the annulus despite variations in the elevation of the subannular surface.

In a further embodiment, shown in FIG. 5A15, the tip portion 122 of arm 120 is covered by a cover member 340. Cover member 340 may comprise a fabric sock-like covering having a teardrop shape and adapted to surround and adhere to a distal portion of the arm 120 (including the tip portion 122). Alternatively, the tip portion 122 may itself be formed in a teardrop shape, and a separate cover member 340 may be correspondingly shaped so as fit over the tip portion 122. The cover member 340 may cover only the teardrop-shaped end of the arm 120, or may cover a larger portion of the arm 120, or in some embodiments, cover the entire arm 120.

FIGS. 6A1 to 6B4 are bottom, front, side and isometric views of prosthetic heart valve devices (apparatus 100) showing arms 120 that cross from a support attachment site on a first side 110S1 of a support 110 to a leaflet and/or annulus engaging site oriented on a second side 110S2 of the support 110 opposite the first side 110S1. In one embodiment, each of the plurality of arms 120 comprises a curved elbow portion 126 configured to span across a downstream portion 114 the support 110 and extend from the first side 110S1 to the second side 110S2. Accordingly, the base portion 124 of arm 120 can be coupled to a different side (e.g., side 110S1) of the support 110 than that on which the tip portion 122 is positioned (e.g., side 110S2). The arms 120 may be constructed like any of the various other embodiments described herein, including single wires or ribbons with looped tips as shown as in FIGS. 6A1-6A4, or in complete loops as shown in FIGS. 6B1-6B4. Upon expansion of the support 110, the arms 120 pull the native leaflets toward each other and/or toward the outer surface 110S of the support 110, thereby enhancing the sealing of the leaflets against the support 110 to prevent perivalvular leaks.

FIG. 7A is a top view of a prosthetic heart valve device (apparatus 100) having an expanded support 110, with optional sealing members 160 (shown in dotted lines) and with arms 120 and having a prosthetic valve 180 retained and positioned inside the expanded support 110. In one embodiment, the prosthetic valve 180 can be placed inside the expandable support 110 when the expandable support 110 is in the expanded configuration 113 and after it has been implanted at the native valve location. The support 110 can be expanded from the delivery configuration 111 to an expanded configuration 113 at the native valve location without a valve contained within the support (as shown), or with a temporary valve 185 coupled inside the expandable support (as shown in FIG. 7B). The prosthetic valve 180 can be positioned transvascularly into the support 110 and implanted or retained within a lumen of the support 110. Operatively, the prosthetic valve 180 can be delivered by catheter and placed inside the support 110 in a delivery configuration, and expanded radially outward as indicated with arrows 182, for example.

FIG. 7A1 shows a prosthetic valve 180 in an expanded configuration for use with the support 110. The prosthetic valve 180 may comprise a commercially available valve, such as, for example, the Sapien™ transcatheter heart valve from Edwards Lifesciences LLC or the CoreValve™ transcatheter heart valve from Medtronic, Inc. The prosthetic valve 180 may comprise an expandable stent-like frame 184 having a compact configuration positionable within the expanded support 110. The frame 184 can be expanded from the compact configuration to a second expanded configuration so as to attach the prosthetic valve 180 to the support 110. The frame 184 may be either balloon-expandable, as in the case of the Sapien valve, or self-expanding, as in the CoreValve valve.

Referring back to FIG. 7A, the expandable support 110 may comprise an inner wall portion 158 configured to inhibit movement of the prosthetic valve 180 relative to the support 110. The inner wall portion 158 may comprise a covering (not shown), and the covering may have a thickness and material properties selected so as to provide one or more of friction or compression when an expandable frame 184 (FIG. 7A1) of the prosthetic valve 180 is urged against the inner wall portion 158 of the support 110. The covering may be a textile such as Dacron or PTFE, a closed-cell foam, or a layer of a polymer, ceramic, sintered metal or other suitable material. Alternatively or additionally, the inner wall portion 158 may comprise structures (not shown) to enhance friction or to couple with the frame 184 of the prosthetic valve 180 such as, for example, bumps, hooks, detents, ridges, scales, protuberances, or coatings.

In various embodiments, the expandable support 110 will be configured to resist expansion beyond a predetermined diameter even under the expansion force of a balloon (not shown) used to expand the prosthetic valve 180. Following expansion of the prosthetic valve 180 within the support 110, especially where the prosthetic valve 180 is balloon expandable, some recoil (radial contraction) of both the frame 184 of the prosthetic valve 180 and the support 110 may occur. The support 110 may therefore be configured to recoil an amount greater than the recoil of the prosthetic valve 180 so that an adequate radial force is maintained between the two structures. The expandable support 110 may comprise skeleton 140 which exerts a radially inwardly directed recoil force against the expandable frame 184 of valve 180, and the expandable frame 184 may comprise a stent which presses radially outward against the skeleton 140. The expandable skeleton 140 can move radially outward with the stent-like expandable frame 184 when a balloon 190 is placed within a lumen of the expandable frame 184 and inflated. When the balloon is deflated, to the extent either the skeleton 140 or the expandable frame 184 experience inward recoil, the skeleton 140 will be adapted to recoil more than the frame 184. The skeleton 140 may comprise one or more of a first strut arrangement, a first strut dimension, a first strut geometry or a first strut material, and the expandable frame 184 may comprise one or more of a second strut arrangement, a second strut dimension, a second strut arrangement or a second strut material different from the one or more of the first strut arrangement, the first strut dimension, the first strut geometry or the first strut material, such that the skeleton 140 is urged radially inward with a recoil force greater than a recoil force of the frame 184 when a balloon placed within a lumen of the frame 184 is deflated.

FIG. 7B is a top view of a prosthetic heart valve device (such as apparatus 100) having an expanded support 110 with arms 120 and a pre-fitted valve structure 185, and showing a separate prosthetic valve 180 retained and positioned inside the expanded support 110 and within the pre-fitted valve structure 185. The pre-fitted valve 185 can, in some embodiments, be the only valve structure used with the device 100 for replacement of a native valve structure. In other embodiments, and as shown in FIG. 7B, a separate prosthetic valve 180 can be delivered following implantation (either immediately or concurrently during a single operation, or at a later time or second operation) of the device 100 displacing the pre-fitted valve structure 185 when inserted into and expanded within the support 110. In some embodiments, the pre-fitted valve structure 185 can be a temporary valve 185. For example, the leaflets 187 of the pre-fitted valve 185 may be folded downstream against an inner wall 158 of the support 110 and sandwiched or compressed between the prosthetic valve 180 and the support 110. The leaflets 187 of the pre-fitted valve 185 comprising selectable material may assist in sealing space between the inner wall 158 of the support 110 and the prosthetic valve 180 to inhibit perivalvular leaks. In addition, the pre-fitted valve 185 may enhance compression and/or friction against an outer surface of the prosthetic valve 180. The support 110 may comprise retaining structures on the inner wall 158 configured to couple the prosthetic valve 180 to the support 110 when the prosthetic valve 180 has been expanded. The prosthetic valve 180 may comprise an expandable frame 184 (shown in FIG. 7A1) and retaining structures on the inner wall 158 of the support 110 may couple to an outer portion of the expandable frame 184 as described above in connection with FIG. 7A. The retaining structures on the inner wall 158 of the support 110 may also urge the pre-fitted valve 185 components against the expandable frame 184. In some arrangements, the use of the expandable support 110 of the present technology may allow a catheter-delivered replacement valve 180 of a given size to be implanted in a substantially larger native valve annulus with effective fixation and prevention of perivalvular leaks.

FIGS. 7B1 to 7B3 show components and construction of a temporary valve 185 comprising leaflets 187 in accordance with embodiments of the present technology. The temporary valve 185 may comprise a sheet of material 189 such as PTFE, woven or knit polyester, bovine pericardium, porcine valve tissue, or other suitable material. The sheet of material 189 can be folded in half and stitched with ePTFE sutures so as to form a cylinder 159 with 3 inner pockets. The inner walls of the three pockets are folded toward the center of the cylinder 159 so as to appose one another, thus forming the leaflets 187 of the temporary valve 185. The temporary valve 185 can be attached to both ends of the skeleton 140 with polypropylene and ePTFE sutures, for example.

FIG. 7C is a top view of a prosthetic heart valve device having an expandable support with a plurality of arms and a pre-fitted valve 185 mounted within the expandable support 110. In some embodiments, the pre-fitted valve 185 can be a permanent valve structure configured for use with the apparatus 100; however, in other embodiments, the pre-fitted valve 185 can be a temporary valve 185. The outer wall 159 (e.g., cylinder shown in FIGS. 7B1-7B3) of the temporary valve 185 can be configured to couple to the inner wall 158 of the support 110 with the leaflets 187 extending across the interior of the support 110 so as to block blood flow through the valve 185 in the upstream direction. The support 110 may include features such as loops, eyelets, cleats, or openings to which sutures or other suitable fastening means may be coupled to facilitate attachment of temporary valve 185 to the inner wall 158.

The temporary valve 185 can be configured to receive a separate catheter-delivered prosthetic valve 180 such that the prosthetic valve 180 substantially displaces leaflets 187 of the first valve 185 when the prosthetic valve 180 is coupled to the support 110. The temporary valve 185 may comprise one or more leaflets 187 adapted so as to increase one or more of compression or friction with the prosthetic valve 180 when an expandable frame 184 of the prosthetic valve 180 is urged against the one or more leaflets 187. The support 110 may comprises a covering over its inner wall 158, and the covering may have a thickness sufficient so as to provide one or more of friction or compression when an expandable frame 184 of the prosthetic valve 180 is expanded within the support 110. The one or more leaflets 187 of temporary valve 185 can also be adapted to increase compression or the friction with the prosthetic valve 180 when sandwiched between the support 110 and the expandable frame 184 of the prosthetic valve 180.

In alternative embodiments, a temporary valve 185 mounted within the support 110 may be configured to be removed prior to coupling a permanent prosthetic valve 180 to the support 110. The temporary valve 185 may be mounted within support 110 by detachable couplings, for example perforated regions of the leaflets 187 that allow the leaflets 187 to be torn away easily. Alternatively, the leaflets 187 may be coupled to the support by sutures or other fasteners that can be cut with catheter-delivered cutting tools. The temporary valve 185 may also be made of a bioerodable material configured to erode and dissolve into the blood over a period of 2 hours to 2 months following implantation.

Instead of a temporary valve 185, a permanent valve may be attached to support 110 and implanted therewith. The permanent valve may be constructed similarly to temporary valve 185 as described above, or like any of the commercially available percutaneous heart valves. In any case, the permanent valve will be collapsible so as to have a profile suitable for percutaneous delivery, and expandable with support 110 for implantation at the native valve location.

Figures 8A, 8B, 8C:
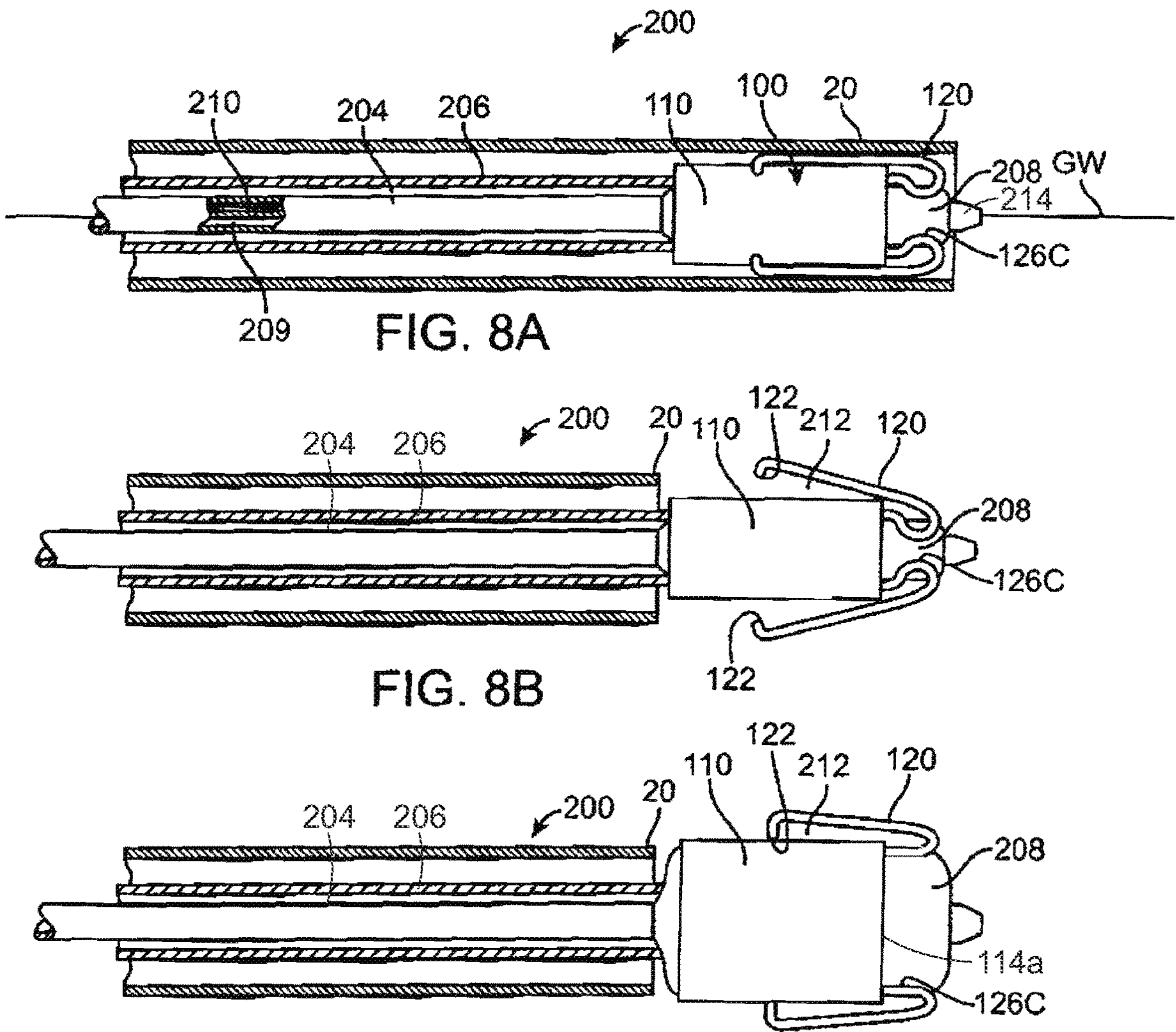
FIGS. 8A-8C are enlarged cross-sectional views of a delivery catheter comprising an inner shaft, a tubular middle shaft slidable over the inner shaft, and a sheath configured to slide over the middle shaft and configured in accordance with embodiments of the present technology.

FIGS. 8A-8C are enlarged cross-sectional views of a delivery catheter 200 comprising an inner shaft 204, a tubular middle shaft 206 slidable over the inner shaft 204 and a sheath 20 configured to slide over the middle shaft 206 in accordance with embodiments of the present technology. An inflatable balloon 208 is mounted to a distal end of the inner shaft 204, and the apparatus 100 is removably mounted over the balloon 208. The inner shaft 204 has an inflation lumen 209 in fluid communication with the interior of balloon 208 to allow the delivery of inflation fluid to the balloon 208 during deployment. The inner shaft 204 optionally has a guidewire lumen 210 which extends through balloon 208 to a tip 214 through which a guidewire GW may be received. In the delivery configuration shown in FIG. 8A, and when sheath 20 is retracted as shown in FIG. 8B, the middle shaft 206 engages the proximal end of the support 110 to maintain its position on the balloon 208. In the expanded configuration shown in FIG. 8C, the middle shaft 206 slides proximally relative to balloon 208 to accommodate the proximal taper of balloon 208 when it is inflated. Optionally, the middle shaft 206 may have one or more longitudinal perforations near its distal end to allow a distal portion of it to split longitudinally as the balloon inflates, thus obviating the need to retract the middle shaft 206 prior to inflation.

In the delivery configuration shown in FIG. 8A, the sheath 20 extends over the arms 120 so as to constrain them in the inward configuration. When the sheath 20 is retracted as shown in FIG. 8B, the arms 120 resiliently move into their unbiased outward configuration, creating a gap 212 between the arms 120 and the support 110 into which the native valve leaflets may be received by retracting the entire delivery catheter 200 in the proximal direction (e.g., upstream direction based on delivery catheter system shown in FIGS. 8A-8C). In operation, once the apparatus 100 is located in the desired position (not shown) relative to the native leaflets, preferably with arms 120 engaging the native annulus in the subannular space, the balloon 208 may be inflated as shown in FIG. 8C. Inflation of the balloon 208 expands the support 110 to a larger diameter, urging the outer surface of support 110 against the annulus. The outer surface 110S of the support 110 expands toward arms 120, closing or narrowing the gap 212 at least partially. By narrowing the gap 212, the arms 120 compresses the native leaflets between the support 110 and the arms 120. In addition, it may be noted that the balloon 208 extends distally beyond the downstream end **114*a* of the support 110 such that the balloon engages the inwardly curved cam regions 126C of arms 120 as it inflates. As the cam regions 126C are pushed outwardly, the tip portions 122 move inwardly toward the support 110**, further compressing the leaflets.

FIGS. 9A-9D are enlarged cross-sectional views of additional embodiments of a delivery catheter 200 having an inner shaft 204 and a middle shaft 208 similar to those described above in connection with FIGS. 8A-C. In FIGS. 9A-9B, however, the balloon 208 is axially shorter than balloon described in the embodiment shown in FIGS. 8A-C. The balloon 208 shown in FIGS. 9A-9D is sized to inflate and expand the support 110 without extending substantially beyond the upstream or downstream ends 112*a*, 114*a* of the support 110. Intermediate elbow portions 126 of the arms 120 may extend distally of the balloon 208 and need not have the inwardly curved cam regions 126C. In this embodiment, the sheath 20 can have a flange 220 around its distal end. Both the distal and proximal surfaces of flange 220 can be tapered or rounded inwardly and can be constructed of or coated with a low-friction lubricious material.

Operatively, in the delivery configuration as shown in FIG. 9A, the arms 120 are constrained by the sheath 20 in the inward configuration with the distal tips 122 against the outer surface of support 110. When the sheath 20 is retracted as shown in FIG. 9B, the arms 120 can resiliently move outwardly a small amount to an unbiased configuration in which a small gap 222 is created between the arms 120 and the support 110. In this configuration, the arms 120 can be angled outwardly substantially less than in the embodiment shown in FIGS. 8A-C, and, for example, the gap 222 can be less than the gap 212 shown in FIG. 8B. The gap 222 need not be large enough to receive the native leaflets, needing only to be large enough to allow flange 220 to be inserted between arms 120 and the support 110. As shown in FIG. 9C, the sheath 20 may then be advanced distally relative to the inner shaft 204 and the apparatus 100 such that the flange 220, facilitated by its tapered distal surface, slides between arms 120 and support 110. As the sheath 20 continues to moves distally, the flange 220 is wedged against the inner surfaces of the arms 120, deflecting the arms further outwardly. Preferably, the sheath 20 is advanced until the flange 220 is disposed within or near the curved elbow portions 126 distal to the downstream end 114*a* of the support 110 so as to provide the maximum area (e.g., gap 222 shown in FIG. 9C) between the arms 120 and the support 110 to receive the native leaflets.

The delivery catheter 200 may then be moved proximally (upstream in the illustrated FIGS. 9A-9D) relative to the native valve such that the native leaflets are received in the now enlarged gap 222 and distal tip portions 122 of the arms 120 engage the annulus. The sheath 20 can then be retracted relative to the apparatus 100 and the lubricious, tapered proximal surface of the flange 220 can slide easily over the native leaflets without drawing the leaflets out of the gap 222. The arms 120 then return to their unbiased configuration of FIG. 9B, closer to the outer surface of support 110. The sheath can then be fully retracted to expose the full length of the support 110, and the balloon 208 can be inflated to expand the support 110 into its expanded configuration, as shown in FIG. 9D. In this step, the gap 222 has closed substantially, with arm tip portions 122 close to or against the outer surface of support 110, thus compressing the native leaflets between the arms 120 and the outer surface of the support 110.

FIG. 10 is an enlarged cross-sectional view of a delivery catheter 200 that includes a second sheath 226 slidably disposed within a first sheath 20, in which the second sheath 226 is configured to slide between the outer surface of a support 110 and a plurality of arms 120 of a prosthetic heart valve device (such as apparatus 100) in accordance with a further embodiment of the present technology. In operation, the distal end of the second sheath 226 can engage the inner surfaces of the arms 120 in a manner similar to the flange 220 described above with respect to FIGS. 9A-9D. Accordingly, the second sheath 226 can force the arms 120, when unconstrained (e.g., with first sheath 20 is retracted proximally), into an outward configuration adapted to receive the native valve leaflets. Optionally, the distal end of the second sheath 226 may have an enlarged flange similar to flange 220 described with respect to FIGS. 9A-9D, and/or a tapered distal end to facilitate insertion under the arms 120. In the delivery configuration, sheath 20 covers the apparatus 100 and constrains the arms 120 in an inward configuration near the outer surface of support 110. In this configuration, the second sheath 226 may be either retracted within sheath 20 proximal to the apparatus 100 or may be positioned between the support 110 and the arms 120. When the sheath 20 is retracted, the second sheath 226 may be advanced distally until it engages the inner surfaces of the arms 120 in the area of the curved elbow portions 126. The arms 120 are thereby forced outwardly (not shown) so that the native leaflets can be received between the arms 120 and the support 110. When the apparatus 100 is positioned in the desired location (not shown), the second sheath 226 can be retracted, allowing the arms 120 to resiliently return to an unbiased configuration closer to the support 110, thereby compressing or retaining the leaflets between the arms 120 and the outside surface of the support 110. The balloon 208 can then be inflated to expand the support 110 within the native annulus, further compressing the leaflets between arms 120 and the outer surface of support 110.

Figure 11A:
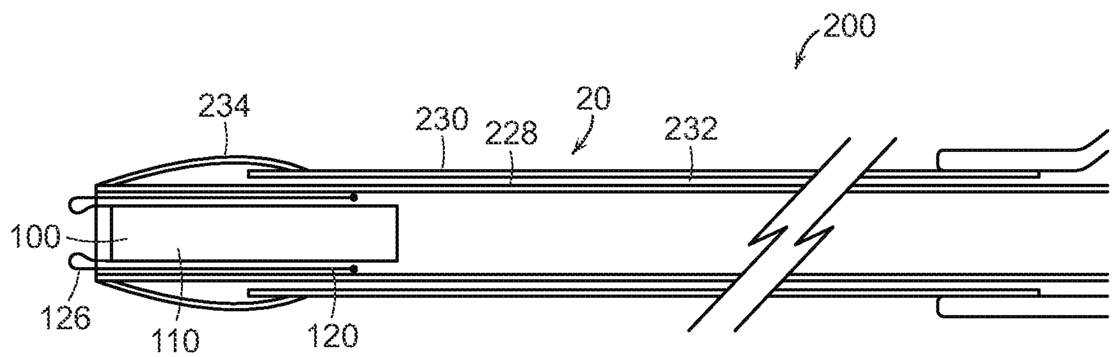
FIGS. 11A-11C are side cross-sectional views of a distal portion of a delivery system for a prosthetic heart valve device configured in accordance with another embodiment of the present technology.
Figure 11B:
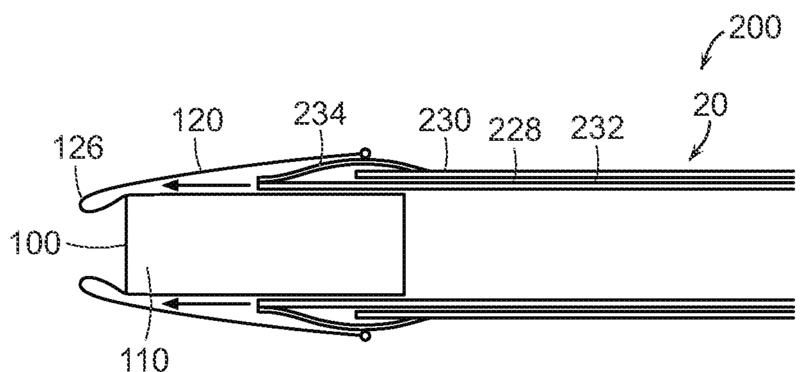
Figure 11C:
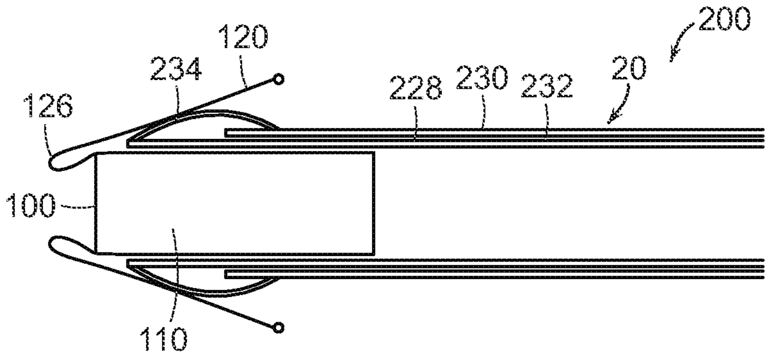

FIGS. 11A-11C are side cross-sectional views of a distal portion of a delivery system for a prosthetic heart valve device (such as apparatus 100) configured in accordance with another embodiment of the present technology. As shown in FIGS. 11A-11C, the sheath 20 may have a coaxial construction including an inner shaft 228, a coaxial outer shaft 230 defining an inflation lumen 232, and a balloon 234 mounted to a distal end of the outer shaft 230. Delivery of an inflation fluid such as saline or contrast fluid through inflation lumen 232 inflates the balloon 234. The apparatus 100 may be positioned within the inner shaft 228. In an unbiased condition, the arms 120 are positioned inwardly near the outer surface of support 110. Operatively, when the sheath 20 is retracted, the arms 120 can spring slightly outwardly from the support 110 a sufficient distance to allow the balloon 234 to be inserted between the arms 120 and the support 110 (e.g., by moving the sheath 20 distally), as shown in FIG. 11B. The sheath 20 can be advanced distally until the balloon 234 is positioned near the U-shaped elbow portion 126. The balloon 234 may then be inflated and urge arms 120 outwardly as shown in FIG. 11C. The delivery catheter 200 is then retracted proximally relative to the native valve in order to capture the leaflets between the arms 120 and the support 110. When the desired location is reached, the balloon 234 may be deflated and the sheath 20 retracted to withdraw the balloon 234 from its position between the support 110 and the arms 120. The arms 120 may then return to their unbiased configuration closer to the outer surface of support 110, trapping or retaining the native leaflets between the arms 120 and the support 110. In some embodiments, the balloon 234 may be coated with a lubricious material in order to facilitate withdrawal of the balloon 134 from between the arms 120 and the support 110 without disturbing the engagement of the leaflets. The support 110 can then be expanded as described above and the apparatus 100 deployed at the native valve site.

Figure 12E:
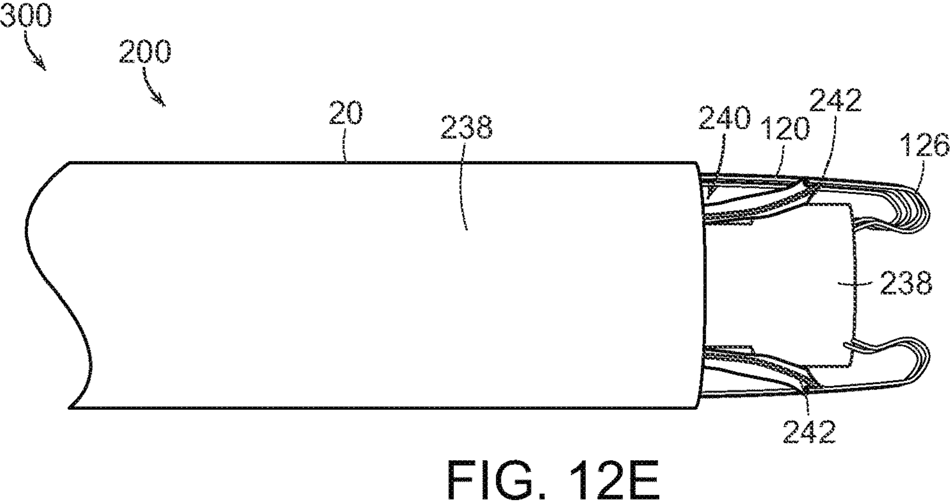

FIGS. 12A-12C are side elevational views of various components of a delivery system 300 for a prosthetic heart valve device (such as apparatus 100) configured in accordance with additional embodiments of the present technology, and FIGS. 12D-12G are side views of a distal portion of the delivery system of FIGS. 12A-12C. The system 300 can include a delivery catheter 200 including a tubular inner sheath 238 having a pair of windows 240 on opposing lateral sides near a distal end 241. Within the inner sheath 238 a pair of scoops 242, optionally interconnected by a ring 243 (shown in FIGS. 12B and 12C) large enough to slide over support (not shown), are received and axially slidable through windows 240 as shown in FIG. 12B. Elongate extensions 244 extend proximally from the ring 243 to facilitate axial movement of the scoops 242. The scoops 242 are preformed to be curved positioned with concave portions facing outward, and with the distal ends 246 spaced further apart than the proximal ends 247, as shown in FIG. 12B. The scoops 242 may also be curved about a longitudinal axis so as to form a concave spoon-like or trough-like shape, with concavity facing outward. The scoops 242 may also have a notch 245 cut in their distal ends 246 as shown in FIG. 12C. In some embodiments, the notch 145 can retain the arms 120 together as the scoops 242 slide forward (further described below).

Referring to FIG. 12D, the support 110 can be positioned within the inner sheath 238 with arms 120 disposed outside of the inner sheath 238 and projecting proximally across the windows 240. In an unbiased condition, the arms 120 are configured to naturally reside in a position close to the outer surface of support 110. Referring to FIG. 12D, in an initial configuration for delivery to the target site, the outer sheath 20 is slidably disposed over the inner sheath 238 and the arms 120, holding the arms 120 against the exterior of the inner sheath 238.

Figure 12F:
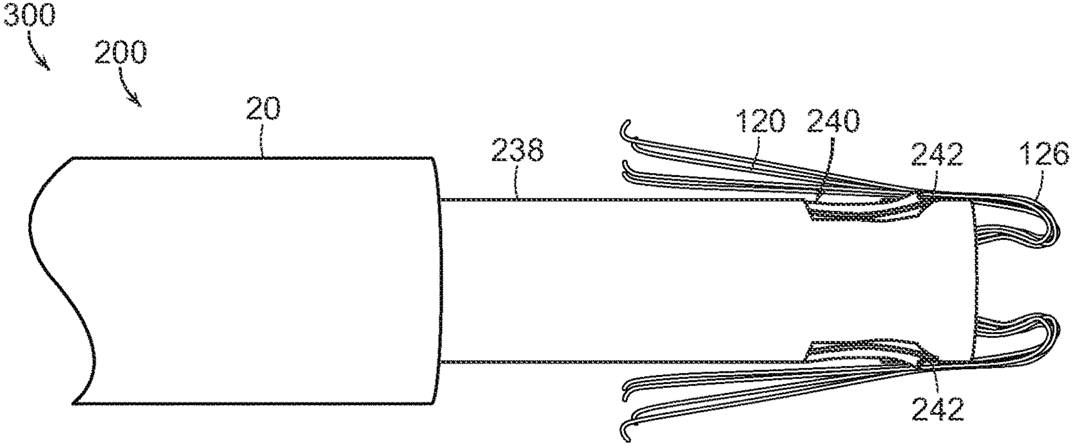
Figure 12G:
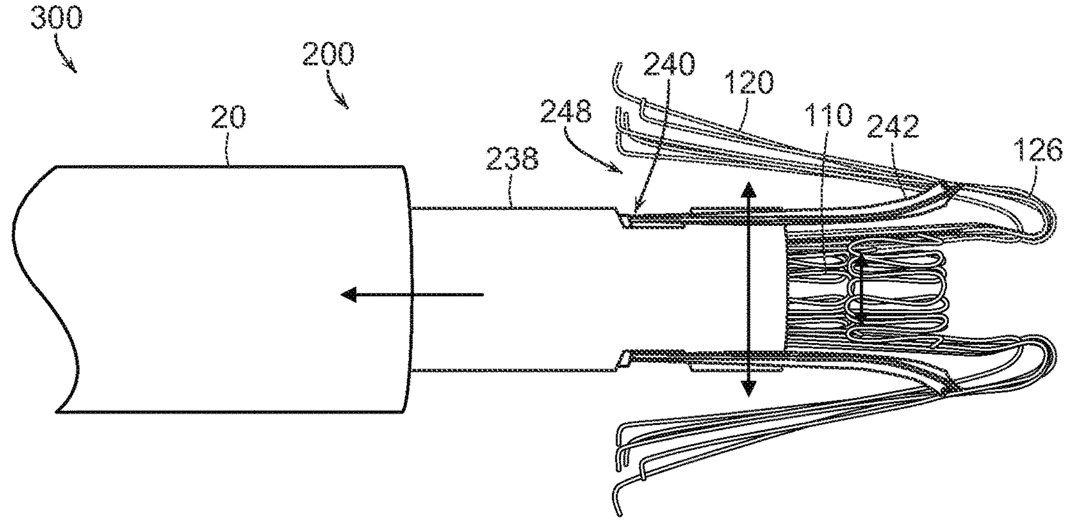

Once the delivery catheter 200 is at the target site, the outer sheath 20 can be retracted as shown in FIG. 12E to expose the arms 120, allowing the arms 120 to spring outwardly from the support 110 and/or inner sheath 238 to their unbiased configuration, shown in FIG. 12F. The scoops 242 are then pushed forward relative to the inner sheath 238 and support 110, and/or the inner sheath 238 and support 110 are retracted relative to the scoops 242, such that the scoops 242 move toward the U-shaped elbow portion 126 of the arms 120. Due to their outwardly-curved configuration, the scoops 242 urge the arms 120 further outward to create a larger gap 248 between the arms 120 and the inner sheath 238, as shown in FIG. 12G. The delivery catheter 200 may then be retracted relative to the native valve, capturing the leaflets between the arms 120 and the inner sheath 238 (not shown). The scoops 242 can then be retracted back through windows 240 (not shown), exiting the space between the native leaflets and the inner sheath 238. This allows the arms 120 to return to an inward configuration closer to the outer surface of support 110, thereby trapping the leaflets between the arms 120 and the support 110. The apparatus 100 may then be expanded and deployed from the delivery catheter 200 as described in connection with other embodiments.

In some embodiments, the apparatus 100 may have an active mechanism for urging the arms 120 inwardly toward support 110 to more forcefully compress the leaflets between the arms 120 and the support 110. FIGS. 13A-13B are elevated side and oblique views, respectively, of a prosthetic heart valve device (apparatus 100) having a belt 250 coupled between an expandable support 110 and a plurality of arms 120 in accordance with an embodiment of the present technology. FIGS. 13C and 13D are top views of the device 100 shown in FIGS. 13A-13B showing the arms 120 in an outward configuration 123 (FIG. 13C) and in an inward configuration 121 (FIG. 13D). In one embodiment, the belt 250 can be coupled to the support 110 and pass slidably through an eyelet 252 in each arm 120. The belt 250 may comprise a suture, wire, band, cable, or other flexible element known in the art. Ultra-high molecular weight polyethylene or stainless steel wire rope can be used in some embodiments because of their strength and creep resistance, which are qualities useful to withstand pulsatile loading and to maintain clamping of the leaflets between the arms 120 and the support 110. In one embodiment, the belt 250 can be coupled to the support 110 at anchor points 254, for example, on opposite sides of the support 110 in the space between the rows (if present) of arms 120, which, in some embodiments can correspond to locations of the native valve commissures. In some arrangements, anchor points 254 can be located near the downstream end **114*a* of the support 110 so that the belt 250 will not interfere with the positioning of the native leaflets between the arms 120 and the support 110. In some embodiments the eyelets 252 can be mounted to an upstream portion of the arms 120, closer to tip portions 122 than to elbow portions 126, so as to maximize leverage on the arms 120. Initially, with the support 110 in the radially collapsed delivery configuration, the belt 250 is loose enough to allow arms 120 to reside or rest in their outward configuration 123, shown in FIGS. 13A-C. As the support 110 is expanded, the distance D between the opposing anchor points 254 is increased, which can cause the belt 250 to tighten, thereby drawing arms 120 inwardly toward the outer surface of the support 110, as shown in FIG. 13D**.

In an alternative configuration, shown in FIG. 14, a pair of belts (shown individually as 250A and 250B) can be used to actively engage the arms 120. For example, rather than a single continuous belt 250 extending around the entire circumference of the support 110 and coupled to all of arms 120 as shown in FIGS. 13A-D, one belt 250A can pass through a first set of arms 120 on one side of the support 110, and a second belt 250B can pass through a second set of arms 120 on the opposing side of support 110. Each belt 250A, 250B is coupled at its ends to an anchor point 254 on the support 110. In some embodiments, belt 250A can be different than belt 250B such that the first set of arms 120 can be arranged differently during implantation of the apparatus 100 and/or once implanted in the native valve region than the second set of arms 120. For example, for devices suitable for implantation at the native mitral valve region, it can, in some embodiments, be desirable for the arms 120 engaging the anterior leaflet AL to be pulled closer to the support 110 to ensure they do not protrude into the left ventricular outflow tract. Accordingly, the belt 250A may have a different length or tension than the belt 250B.

Figure 15A:
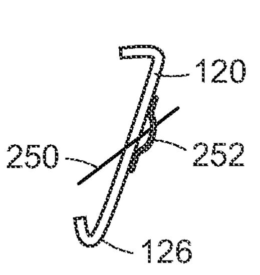
FIGS. 15A-15C are side views of a portion of an individual arm associated with a prosthetic heart valve device and showing mechanisms for coupling a belt to the arm in accordance with various embodiments of the present technology.
Figure 15B:
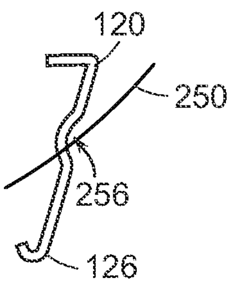
Figure 15C:
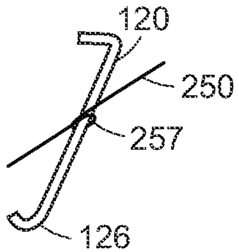

Belt 250 may be coupled to the arms 120 in various ways. FIGS. 15A-15C are side views of a portion of an individual arm 120 associated with a prosthetic heart valve device (such as apparatus 100) and showing mechanisms for coupling a belt 250 to the arm 120 in accordance with various embodiments of the present technology. As shown in FIG. 15A, the arm 120 has a loop or eyelet 252 mounted to the arm 120 and through which the belt 250 can slidably pass. As shown in FIG. 15B, the arm 120 can have a dent, trough, or groove 256 adapted to receive the belt 250 and prevent it from slipping down the arm 120 in the downstream direction when the belt 250 is tensioned. Alternatively, and as shown in FIG. 15C, the belt 250 can be wrapped around the arm 120 to form a complete turn or loop 257 such that the belt 250 can slide relative to the arm 120 while exerting sufficient friction with the arm 120 to inhibit it from sliding along the arm 120. In other embodiments, eyelets 252 or other belt-retaining features may be incorporated into the tip portions 122 of the arms 120. For example, the tip portions 122 may form a loop as described elsewhere herein, and the belt 250 may pass through the loops.

Figure 16A:
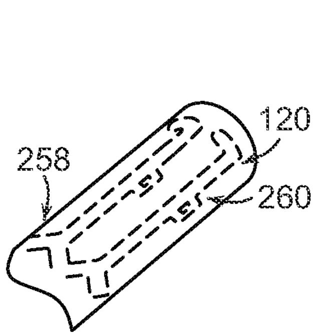
FIGS. 16A-16C are oblique views showing the making of an arm for a prosthetic heart valve device wherein the arm has an eyelet to receive a belt and configured in accordance with further embodiments of the present technology.
Figure 16B:
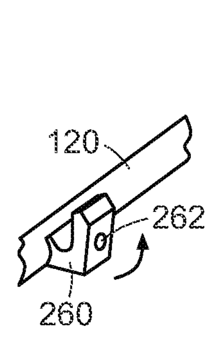
Figure 16C:
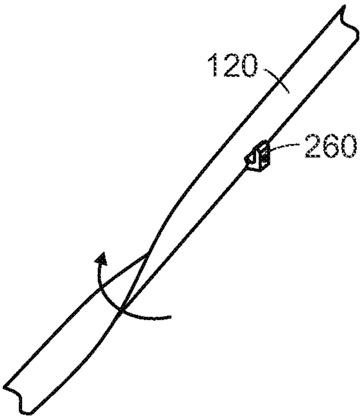

In a further embodiment, the arm 120 may have a hole, eyelet or other feature integrally formed in the arm itself through which the belt 250 may pass. FIGS. 16A-16C are oblique views showing the making of an arm 120 for a prosthetic heart valve device (such as apparatus 100) wherein the arm 120 has an eyelet to receive a belt 250 and configured in accordance with further embodiments of the present technology. For example, as shown in FIG. 16A, the arms 120 may each be laser cut from a metal tube 258 so as to have a tab 260 extending from the side of the arm 120. Referring to FIG. 16B, the tab 260 may have a hole 262 through which the belt 250 (not shown) may pass. After laser cutting, the tabs 260 may optionally be formed or bent so as to protrude radially outward from the arm 120 such that the hole 262 extends in the circumferential or tangential direction and is radially outward from the outer surface of arm 120, thereby allowing the belt 250 to slide easily (shown in FIG. 16B). Alternatively, the arm 120 may be twisted, as shown in FIG. 16C, to position the tab 260 and the hole 262 in the desired orientation.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A prosthetic treatment apparatus for treating a native valve having a native annulus and native leaflets, the prosthetic treatment apparatus comprising:

a support having a downstream portion and an upstream portion, wherein the support is expandable from a low-profile configuration for delivery to an expanded configuration for implantation at the native valve;

a prosthetic valve mounted to the support and adapted to allow blood flow in a downstream direction and to block blood flow in an upstream direction;

an arm coupled to the downstream portion of the support, wherein the arm extends in an upstream direction and is wrapped helically around an exterior of the support.

2. The prosthetic treatment apparatus of claim 1, wherein the arm comprises a plurality of arms, and each arm of the plurality of arms comprises a wire loop wrapped helically around the exterior of the support.

3. The prosthetic treatment apparatus of claim 1, further comprising a covering disposed on the arm.

4. The prosthetic treatment apparatus of claim 3, wherein the covering is configured to promote tissue ingrowth.

5. The prosthetic treatment apparatus of claim 1, wherein the arm comprises a wire having a first portion extending in an upstream and first circumferential direction, a loop at an upstream end of the first portion, and a second portion extending from the loop in a downstream and second circumferential direction.

6. The prosthetic treatment apparatus of claim 5, wherein the second circumferential direction is opposite the first circumferential direction.

7. The prosthetic treatment apparatus of claim 1, further comprising a flange extending outwardly from the upstream portion of the support.

8. The prosthetic treatment apparatus of claim 7, wherein the flange is integrally formed with the support.

9. The prosthetic treatment apparatus of claim 7, wherein the flange is a separate component coupled to the support.

10. The prosthetic treatment apparatus of claim 1, wherein the arm is a separate component coupled to the support.

11. The prosthetic treatment apparatus of claim 1, wherein the support is substantially cylindrical.

12. A prosthetic treatment apparatus for treating a native atrioventricular valve having a native annulus and native leaflets, the prosthetic treatment apparatus comprising:

a prosthetic valve; and a support configured to support the prosthetic valve within the native atrioventricular valve, the support comprising:

an atrial part configured to be deployed on an atrial side of the native valve annulus;

a cylindrical part to which the prosthetic valve is coupled, the cylindrical part configured to be deployed such that a ventricular end of the cylindrical part is disposed within the ventricle; and a plurality of arms coupled to the ventricular end of the cylindrical part, wherein with the prosthetic treatment apparatus in a radially expanded configuration, the arms extend in an upstream direction and circumferential direction such that each arm is wrapped helically around an exterior of the support.

13. The prosthetic treatment apparatus of claim 12, wherein each arm of the plurality of arms comprises a wire loop wrapped helically around the exterior of the support.

14. The prosthetic treatment apparatus of claim 12, wherein each arm comprises a wire having a first portion extending in an upstream and first circumferential direction, a loop at an upstream end of the first portion, and a second portion extending from the loop in a downstream and second circumferential direction.

15. The prosthetic treatment apparatus of claim 14, wherein the second circumferential direction is opposite the first circumferential direction.

16. The prosthetic treatment apparatus of claim 12, further comprising a covering disposed on the plurality of arms.

17. The prosthetic treatment apparatus of claim 12, wherein the atrial part comprises a flange extending outwardly from an atrial end of the cylindrical portion.

18. The prosthetic treatment apparatus of claim 17, wherein the flange is a separate component coupled to the support.

19. The prosthetic treatment apparatus of claim 12, wherein the plurality of arms are separate components coupled to the support.

* * * * *